United States Patent [19]
Ewing et al.

[11] Patent Number: 6,034,093
[45] Date of Patent: Mar. 7, 2000

[54] SUBSTITUTED SULFONIC ACID N-[(AMINOIMINOMETHYL)PHENYLALKYL]-AZAHETEROCYCLYLAMIDE COMPOUNDS

[75] Inventors: William R. Ewing, Downingtown; Michael R. Becker, Norristown; Yong Mi Choi-Sledeski; Heinz W. Pauls, both of Collegeville; Daniel G. McGarry, King of Prussia; Roderick S. Davis, West Chester; Alfred P. Spada, Lansdale, all of Pa.

[73] Assignee: Rhone-Poulenc Rorer Pharmaceuticals Inc., Collegeville, Pa.

[21] Appl. No.: 09/130,336

[22] Filed: Aug. 6, 1998

Related U.S. Application Data

[63] Continuation-in-part of application No. PCT/US97/22414, Dec. 1, 1997, which is a continuation-in-part of application No. 08/761,414, Dec. 6, 1996, Pat. No. 5,731,315, which is a continuation-in-part of application No. PCT/US96/09816, Jun. 7, 1996, which is a continuation-in-part of application No. 08/481,024, Jun. 7, 1995, Pat. No. 5,612,353, and a continuation-in-part of application No. PCT/US97/22414, which is a continuation-in-part of application No. 08/976,034, Nov. 21, 1997, which is a continuation of application No. PCT/US96/09816, which is a continuation-in-part of application No. 08/481,024.

[51] Int. Cl.$^7$ .................. C07D 401/02; A61K 31/40; A61K 31/435

[52] U.S. Cl. .................. 514/301; 514/343; 514/422; 514/426; 546/114; 546/276.4; 548/557

[58] Field of Search .................. 544/335; 546/114, 546/139, 176, 276.4; 548/557; 514/269, 301, 307, 314, 343, 422, 426

[56] References Cited

U.S. PATENT DOCUMENTS

| | | | |
|---|---|---|---|
| 5,612,353 | 3/1997 | Ewing et al. | 514/309 |
| 5,731,315 | 3/1998 | Ewing et al. | 514/269 |

*Primary Examiner*—Zinna Northington Davis
*Attorney, Agent, or Firm*—Rose J. Oehler

[57] ABSTRACT

The compounds of formula I exhibit useful pharmacological activity and accordingly are incorporated into pharmaceutical compositions and used in the treatment of patients suffering from certain medical disorders. More specifically, they are inhibitors of the activity of Factor Xa. The present invention is directed to compounds of formula I, compositions containing compounds of formula I, and their use, which are for treating a patient suffering from, or subject to, physiological condition which can be ameliorated by the administration of an inhibitor of the activity of Factor Xa.

30 Claims, No Drawings

SUBSTITUTED SULFONIC ACID N-[(AMINOIMINOMETHYL)PHENYLALKYL]-AZAHETEROCYCLYLAMIDE COMPOUNDS

This application is a continuation-in-part application of copending PCT US97/22414, filed Dec. 1, 1997, which desingates the United States, which, in turn, is a continuation-in-part application of U.S. patent application Ser. No. 08/761,414, filed Dec. 6, 1996, now U.S. Pat. No. 5,731,315, issued Mar. 24, 1998, which, in turn, is a continuation-in-part application of PCT US96/09816, filed Jun. 7, 1996, which designates the United States, which, in turn, is a continuation-in-part application of U.S. patent application Ser. No. 08/481,024, filed Jun. 7, 1995, now U.S. Pat. No. 5,612,353, issued Mar. 18, 1997. This application is also a continuation-in-part application of copending PCT US97/22414, filed Dec. 1, 1997, which designates the United States, which, in turn, is a continuation-in-part of copending U.S. patent application Ser. No. 08/976,034, filed Nov. 21, 1997, which, in turn, is a continuation application of PCT US96/09816, filed Jun. 7, 1996, which designates the United States, which, in turn, is a continuation-in-part application of U.S. patent application Ser. No. 08/481,024, filed Jun. 7, 1995, now U.S. Pat. No. 5,612,353, issued Mar. 18, 1997.

FIELD OF THE INVENTION

The compounds of formula I exhibit useful pharmacological activity and accordingly are incorporated into pharmaceutical compositions and used in the treatment of patients suffering from certain medical disorders. More specifically, they are Factor Xa inhibitors. The present invention is directed to compounds of formula I, compositions containing compounds of formula I, and their use, which are for treating a patient suffereing from, or subject to, conditions which can be ameliorated by the administration of an inhibitor of Factor Xa.

Factor Xa is the penultimate enzyme in the coagulation cascade. Both free factor Xa and factor Xa assembled in the prothrombinase complex (Factor Xa, Factor Va, calcium and phospholipid) are inhibited by compounds of formula I. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (retenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening clots throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

SUMMARY OF THE INVENTION

This invention is directed to the pharmaceutical use of a compound of formula I below for treating a patient suffereing from a physiological disorder capable of being modulated by inhibiting the activity of Factor Xa, where formula I is as follows:

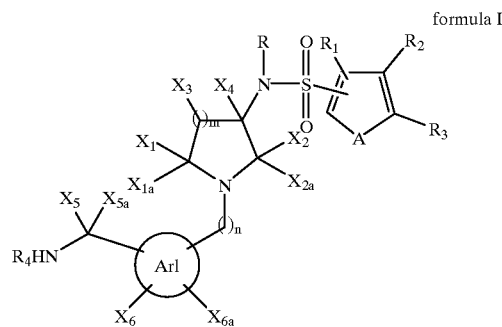

Arl is phenyl or monocyclic heteroaryl;

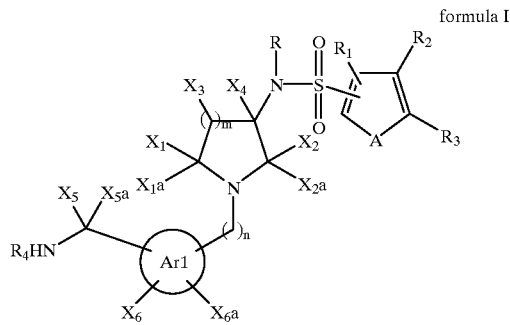

Arl is phenyl or monocyclic heteroaryl;

R is hydrogen, optionally substituted alkyl, optionally substituted aralkyl, optionally substituted heteroaralkyl, $R_6O(CH_2)_x-$, $R_6O_2C(CH_2)_x-$, $Y^1Y^2NC(O)(CH_2)_x-$, or $Y^1Y^2N(CH_2)_x-$;

$R_1$ is hydrogen, alkyl, hydroxy, alkoxy, $Y^1Y^2N-$, halogen, $-CO_2R_6$, $-C(O)NY^1Y^2$, $-(CH_2)_xOR_6$, $-(CH_2)_x NY^1Y^2$, or $-CN$;

$R_2$ and $R_3$ are independently selected from hydrogen, hydroxy, alkoxy, $Y^1Y^2N-$, halogen, $-CO_2R_6$, $-C(O)$ $NY^1Y^2$, —$(CH_2)_xOR_6$, —$(CH_2)_xNY^1Y^2$, —CN, optionally substituted alkyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl or optionally substituted heteroaralkenyl, or $R_2$ and $R_3$ taken together with the carbon atoms through which they are linked form an optionally substituted 5 to 7 membered fused cycloalkyl, optionally substituted 5 to 7 membered fused heterocyclyl ring or an optionally substituted 6 membered fused aryl, or an optionally substituted 5 to 7 membered fused heteroaryl ring;

$R_4$ is hydrogen or optionally substituted lower alkyl, optionally substituted aralkyl or optionally substituted heteroaralkyl;

$X_1$ and $X_{1a}$ are independently selected from hydrogen, optionally substituted alkyl, optionally substituted aryl, optionally substituted aralkyl, optionally substituted heteroaryl or optionally substituted heteroaralkyl, or $X_1$ and $X_{1a}$ taken together form oxo;

$X_2$ and $X_{2a}$ are hydrogen, or taken together form oxo;

$X_3$ is hydrogen, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1a}$ taken together with the carbon atoms through which $X_3$ and one of $X_1$ and $X_{1a}$ are linked form a 4 to 7 membered cycloalkyl or heterocyclyl ring;

$X_4$ is hydrogen, optionally substituted alkyl or an optionally substituted aralkyl;

$X_5$ and $X_{5a}$ are hydrogen or taken together are =$NR_5$;

$R_5$ is hydrogen, $R_6O_2C$—, $R_6O$—, cyano, $R_6CO$—, optionally substituted lower alkyl, nitro or $Y^1Y^2N$—;

$Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl;

$X_6$ and $X_{6a}$ are independently hydrogen, $R_7R_8N$—, $R_9O$—, $R_7R_8NCO$—, $R_7R_8NSO_2$—, $R_7R_8NSO_2N$—, $R_7R_8SO_2O$—, $R_9CO$—, —$CO_2R_6$, —$C(O)NY^1Y^2$, —$(CH_2)_xCO_2R_6$, —$(CH_2)_xC(O)NY^1Y^2$, —$(CH_2)_xOR_6$, —$(CH_2)_xNY^1Y^2$, halo, cyano or nitro;

$R_6$ is hydrogen, optionally substituted alkyl, optionally substituted aralkyl or optionally substituted heteroaralkyl;

$R_7$ and $R_8$ are independently hydrogen or optionally substituted lower alkyl, or one of $R_7$ and $R_8$ is hydrogen and the other of $R_7$ and $R_8$ is $R_{10}(O)CCH_2$—or lower acyl;

$R_9$ is hydrogen, optionally substituted lower alkyl, optionally substituted lower acyl or $R_{10}(O)CCH_2$—;

$R_{10}$ is hydrogen, optionally substituted lower alkyl, optionally substituted alkoxy or hydroxy;

A is S or —CH=CH—;

m is 0,1,2 or 3;

n is 0,1,2 or 3; and x is 1,2,3,4, or 5, or a pharmaceutically acceptable salt thereof, an N-oxide thereof, a hydrate thereof or a solvate thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, hydroxy, alkoxy, amino, acylamino, aroylamino, carboxy, alkoxycarbonyl, aralkyloxycarbonyl, heteroaralkyloxycarbonyl or $Y^1Y^2NCO$—, where $Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl. Exemplary alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, pyridylmethyloxycarbonylmethyl.

"Cycloalkyl" means a non-aromatic mono- or multicyclic ring system of about 3 to about 10 carbon atoms. Exemplary monocyclic cycloaklyl rings include cyclopentyl, cyclohexyl and cycloheptyl. The cycloalklyl group is optionally partially unsaturated or optionally substituted with one or more cycloalkyl group substituents which may be the same or different, where "cycloalkyl group substituent" includes hydrogen, alkyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroarylsulfonyl, fused cycloalkyl, fused heterocyclyl, arylazo, heteroarylazo, $Y^1Y^2N$—, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl. Exemplary multicyclic cycloaklyl rings include 1-decalin, nobornyl, adamant-(1- or 2-)yl.

"Heterocyclyl" means a non-aromatic monocyclic or multicyclic ring system of about 3 to about 10 ring atoms. Preferred rings include about 5 to about 6 ring atoms wherein one of the ring atoms is oxygen, nitrogen or sulfur. The heterocyclyl is optionally partially unsaturated or optionally substituted with one or more heterocyclyl group substituents which may be the same or different, where "heterocyclyl group substituent" includes hydrogen, alkyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused heterocyclyl, arylazo, heteroarylazo, $Y^1Y^2N$—, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl. The heterocyclyl group substituents are as defined herein. Exemplary monocyclic rings include pyrrolidyl, piperidyl, tetrahydrofuranyl, tetrahydrothienyl and tetrahydrothiopyranyl. The thio or nitrogen moiety of the heterocyclyl may also be optionally oxidized to the corresponding N-oxide, S-oxide or S,S-dioxide.

"Aryl" means a 6 to 10 membered aromatic monocyclic or multicyclic hydrocarbon ring system. Exemplary aryl include phenyl or naphthyl, or phenyl substituted or naphthyl substituted with one or more aryl group substituents which may be the same or different, where "aryl group substituent" includes hydrogen, alkyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused heterocyclyl, arylazo, heteroarylazo, $Y^1Y^2N-$, $Y^1Y^2NCO-$ or $Y^1Y^2NSO_2-$, wherein $Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl. The aryl group substituents are as defined herein. Preferred aryl groups are optionally substituted phenyl or optionally substituted naphthyl. Preferred aryl group substituents include hydrogen, alkyl, hydroxy, acyl, aryl aroyl, aryloxy, halo, nitro, alkoxy, cyano, alkoxycarbonyl, acylamino, alkylthio, $Y^1Y^2N-$, $Y^1Y^2NCO-$ or $Y^1Y^2NSO_2-$, where $Y^1$ and $Y^2$ are independently optionally substituted alkyl, aryl, aralkyl or heteroaralkyl; preferred phenyl group substituents are hydroxy, halogen, alkyl, amino.

"Heteroaryl" means about a 5- to about a 10- membered aromatic monocyclic or multicyclic hydrocarbon ring system in which one or more of the carbon atoms in the ring system is/are element(s) other than carbon, for example nitrogen, oxygen or sulfur. The "heteroaryl" may also be substituted by one or more of the above-mentioned "aryl group substituents". Exemplary heteroaryl groups include substituted pyrazinyl, furanyl, thienyl, pyridyl, pyrimidinyl, isoxazolyl, isothiazolyl, oxazolyl, thiazolyl, pyrazolyl, furazanyl, pyrrolyl, imidazo[2,1-b]thiazolyl, benzofurazanyl, indolyl, azaindolyl, benzimidazolyl, benzothienyl, quinolinyl, imidazolyl and isoquinolinyl. Where (Ar1)

is a monocyclic heteroaryl, then preferred heteroaryls include thienyl or pyridyl.

"Aralkyl" means an aryl-alkyl- group in which the aryl and alkyl are as previously described. Preferred aralkyls contain a lower alkyl moiety. Exemplary aralkyl groups include benzyl, 2-phenethyl and naphthlenemethyl.

"Heteroaralkyl" means a heteroaryl-alkyl- group in which the heteroaryl and alkyl are as previously described. Preferred heteroaralkyls contain a lower alkyl moiety. Exemplary heteroaralkyl groups may contain thienylmethyl, pyridylmethyl, imidazolylmethyl and pyrazinylmethyl.

"Aralkenyl" means an aryl-alkenyl- group in which the aryl and alkenyl are as previously described. Preferred aralkenyls contain a lower alkenyl moiety. An exemplary aralkenyl group is 2-phenethenyl.

"Heteroaralkenyl" means a heteroaryl-alkenyl- group in which the heteroaryl and alkenyl are as previously described. Preferred heteroaralkenyls contain a lower alkenyl moiety. Exemplary heteroaralkenyl groups may contain thienylethenyl, pyridylethenyl, imidazolylethenyl and pyrazinylethenyl.

"Hydroxyalkyl" means a HO-alkyl- group in which alkyl is as previously defined. Preferred hydroxyalkyls contain lower alkyl. Exemplary hydroxyalkyl groups include hydroxymethyl and 2-hydroxyethyl.

"Acyl" means an H—CO— or alkyl —CO— group in which the alkyl group is as previously described. Preferred acyls contain a lower alkyl. Exemplary acyl groups include formyl, acetyl, propanoyl, 2-methylpropanoyl, butanoyl and palmitoyl.

"Aroyl" means an aryl—CO— group in which the aryl group is as previously described. Exemplary groups include benzoyl and 1- and 2-naphthoyl.

"Heteroaroyl" means an means an heteroaryl—CO— group in which the heteroaryl group is as previously described. Exemplary groups include thiophenoyl and pyridinoyl.

"Alkoxy" means an alkyl—O— group in which the alkyl group is as previously described. Exemplary alkoxy groups include methoxy, ethoxy, n-propoxy, i-propoxy, n-butoxy and heptoxy.

"Aryloxy" means an aryl—O— group in which the aryl group is as previously described. Exemplary aryloxy groups include phenoxy and naphthoxy.

"Aralkyloxy" means an aralkyl—O— group in which the aralkyl groups is as previously described. Exemplary aralkyloxy groups include benzyloxy and 1- or 2-naphthalenemethoxy.

"Alkylthio" means an alkyl—S— group in which the alkyl group is as previously described. Exemplary alkylthio groups include methylthio, erthylthio, i-propylthio and heptythio.

"Arylthio" means an aryl—S— group in which the aryl group is as previously described. Exemplary arylthio groups include phenylthio and naphthylthio.

"Aralkylthio" means an aralkyl—S— group in which the aralkyl group is as previously described. An exemplary aralkylthio group is benzylthio.

"$Y^1Y^2N-$" means a substituted or unsubstituted amino group, wherein $Y^1$ and $Y^2$ are as previously described. Exemplary groups include amion($H_2N-$), methylamino, dimethylamino, diethylamino, pyrrolidine, piperidine, benzylamino, or phenethylamino.

"Alkoxycarbonyl" means an alkyl—O—CO— group. Exemplary alkoxycarbonyl groups include methoxycarbonyl, ethoxycarbonyl, or t-butyloxycarbonyl.

"Aryloxycarbonyl" means an aryl—O—CO— group. Exemplary aryloxycarbonyl groups include phenoxycarbonyl and naphthoxycarbonyl.

"Aralkoxycarbonyl" means an aralkyl—O—CO— group. An exemplary aralkoxycarbonyl group is benzyloxycarbonyl.

"$Y^1Y^2NCO-$" means a substituted or unsubstituted carbamoyl group, wherein $Y^1$ and $Y^2$ are as previously described. Exemplary groups are carbamoyl ($H_2NCO-$) and dimethylaminocarbamoyl ($Me_2NCO-$).

"$Y^1Y^2NSO_2-$" means a substituted or unsubstituted sulfamoyl group, wherein $Y^1$ and $Y^2$ are as previously described. Exemplary groups are aminosulfamoyl ($H_2NSO_2$—) and dimethylaminosulfamoyl ($Me_2NSO_2$—).

"Acylamino" is an acyl—NH— group wherein acyl is as defined herein.

"Aroylamino" is an aroyl—NH— group wherein aroyl is as defined herein.

"Alkylsulfonyl" means an alkyl—$SO_2$— group. Preferred groups are those in whicht he alkyl group is lower alkyl.

"Alkylsulfinyl" means an alkyl-SO— group. Preferred groups are those in whicht he alkyl group is lower alkyl.

"Arylsulfonyl" means an aryl-$SO_2$— group.

"Arylsulfinyl" means an aryl-SO— group.

"Halo" means fluoro, chloro, bromo, or iodo. Preferred are fluoro, chloro or bromo, and more preferred are fluoro or chloro.

PREFERRED EMBODIMENTS

A preferred embodiment of the invention is a method for treating a patient suffering from a physiological disorder capable of being modulated by inhibiting an activity of Factor Xa by administering a therapeutically effective amount of a compound of formula I.

Another preferred compound aspect of the invention is the compound of formula I wherein n is 1, and m is 1.

Another preferred compound aspect of the invention is the compound of formula I wherein $X_2$ and $X_{2a}$ taken together are oxo.

Another preferred compound aspect of the invention is the compound of formula I wherein $X_1$, $X_{1a}$, $X_4$ are hydrogen, and $X_3$ is hydrogen or alkyl.

Another preferred compound aspect of the invention is the compound of formula I wherein $X_5$ and $X_{5a}$ taken together are =$NR_5$ wherein $R_5$ is $R_6O_2C$—.

Another preferred compound aspect of the invention is the compound of formula I wherein $X_5$ and $X_{5a}$ taken together are =$NR_5$ wherein $R_5$ is —OH.

Another preferred compound aspect of the invention is the compound of formula I wherein $X_5$ and $X_{5a}$ taken together are =$NR_5$ wherein $R_5$ is H.

Another preferred compound aspect of the invention is the compound of formula I wherein

is phenyl and the carbon substituted with $X_5X_{5a}$ and $R_4HN$— is attached meta relative to the attachment of the —$(CH)_nN$— moiety to the phenyl.

Another preferred compound aspect of the invention is the compound of formula I wherein

is thienyl and the carbon substituted with $X_5$, $X_{5a}$ and $R_4HN$— is attached in the 2 position relative to the sulfur of the thienyl and the attachment of the —$(CH)_nN$— moiety is to the 4 position of the thienyl.

Another preferred compound aspect of the invention is the compound of formula I wherein R is hydrogen, methyl, aralkyl, heteroaralkyl, $HO_2CCH_2$—, $H_2NC(O)CH_2$—, or $R_6HNC(O)CH_2$—.

Another preferred compound aspect of the invention is the compound of formula I wherein $R_1$ is hydrogen, alkyl, or halogen.

Another preferred compound aspect of the invention is the compound of formula I wherein $R_2$ and $R_3$ are independently hydrogen, halogen, alkoxy, amino, aryl, or heteroaryl.

Another preferred compound aspect of the invention is the compound of formula I wherein $R_2$ and $R_3$ form an optionally substituted fused aryl or an optionally substituted fused heteroaryl ring wherein the substituent is halogen, alkyl, amino, hydroxy, or alkoxy.

Another preferred compound aspect of the invention is the compound of formula I wherein $R_2$ and $R_3$ form an optionally substituted fused cycloalkyl or an optionally substituted fused heterocyclyl in which the heteroatom is nitrogen wherein the substituent is hydrogen, $Y^1Y^2N$, or alkyl.

Another preferred compound aspect of the invention is the compound of claim 1 wherein

is phenyl and one of $X_6$ and $X_{6a}$ is amino or hydroxy in a para position relative to the

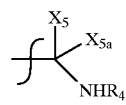

moiety.

Another preferred compound aspect of the invention is the compound of claim 1 wherein $X_6$ $X_{6a}$ are hydrogen.

Another preferred compound aspect of the invention is the compound of claim 1 wherein A is —CH=CH—; $R_2$ and $R_3$ taken together with the carbon atoms through which $R_2$ and $R_3$ are linked form an optionally substituted 5 or 6 membered heteroaryl ring, preferably containing at least one hetero atom which is N, or an optionally substituted 6 membered aryl ring, and wherein said substituents are preferably chloro, hydroxy or amino.

Another preferred compound aspect of the invention is the compound of claim 1 wherein A is —CH=CH—; $R_2$ is hydrogen; and $R_3$ is an optionally substituted heteroaryl ring, preferably 5 or 6 membered heteroaryl ring, preferably containing at least one hetero atom which is N or S, or an optionally substituted 6 membered aryl ring, and wherein said substituents are preferably chloro, hydroxy or amino.

Another preferred compound aspect of the invention is the compound of claim 1 wherein A is S (sulfur).

Another preferred compound aspect of the invention is the compound of claim 1 wherein A is S (sulfur); and $R_2$ and $R_3$ taken together with the carbon atoms through which $R_2$ and $R_3$ are linked form an optionally substituted 5 or 6 membered heteroaryl ring, preferably containing at least one hetero atom which is N, or an optionally substituted 6 membered aryl ring, and wherein said substituents are preferably chloro, hydroxy or amino.

Another preferred compound aspect of the invention is the compound of claim 1 wherein A is S (sulfur); $R_2$ is hydrogen; and $R_3$ is an optionally substituted heteroaryl ring, preferably 5 or 6 membered heteroaryl ring, preferably containing at least one hetero atom which is N or S, or an optionally substituted 6 membered aryl ring, and wherein said substituents are preferably chloro, hydroxy or amino.

Species according to the invention are selected from the group consisting of:

3-[3-(S)-(Benzo[b]thiophene-2-sulfonylamino)-2-oxo-pyrrolidin-1-ylmethyl]-benzamidine trifluoroacetate;
3-[3-(S)-[(Benzo[b]thiophene-2-sulfonyl)-methylamino]-2-oxo-pyrrolidin-1-ylmethyl]-benzamidine trifluoroacetate;
4-[3-(S)-(Benzo[b]thiophene-2-sulfonylamino)-2-oxo-pyrrolidin-1-ylmethyl]-thiophene-2-carboxamidine trifluoroacetate;
4-[3-(S)-[(Benzo[b]thiophene-2-sulfonyl)-methylamino]-2-oxo-pyrrolidin-1-ylmethyl]-thiophene-2-carboxamidine trifluoroacetate;
3-[3-(S)-(4-Chlorobenzo[b]thiophene-2-sulfonylamino)-2-oxo-pyrrolidin-1-ylmethyl]-benzamidine trifluoroacetate;
3-[3-(S)-(6-Chlorobenzo[b]thiophene-2-sulfonylamino)-2-oxo-pyrrolidin-1-ylmethyl]-benzamidine trifluoroacetate;
3-[3-(S)-(4-Chlorobenzo[b]thiophene-2-sulfonyl)-methylamino)-2-oxo-pyrrolidin-1-ylmethyl]-benzamidine trifluoroacetate;
3-[3-(S)-(6-Chlorobenzo[b]thiophene-2-sulfonyl)-methylamino)-2-oxo-pyrrolidin-1-ylmethyl]-benzamidine trifluoroacetate;
3-[3-(S)-(5-Chlorobenzo[b]thiophene-2-sulfonylamino)-2-oxo-pyrrolidin-1-ylmethyl]-benzamidine trifluoroacetate;
3-[3-(S)-[(5-Chlorobenzo[b]thiophene-2-sulfonyl)-methylamino]-2-oxo-pyrrolidin-1-ylmethyl]-benzamidine trifluoroacetate;
3-[3-(S)-(4-Methylbenzo[b]thiophene-2-sulfonylamino)-2-oxo-pyrrolidin-1-ylmethyl]-benzamidine trifluoroacetate;
3-[3-(S)-(6-Methylbenzo[b]thiophene-2-sulfonylamino)-2-oxo-pyrrolidin-1-ylmethyl]-benzamidine trifluoroacetate;
3-[3-(S)-(5-Methylbenzo[b]thiophene-2-sulfonylamino)-2-oxo-pyrrolidin-1-ylmethyl]-benzamidine trifluoroacetate;
3-[3-(S)-(4,6-Dichlorobenzo[b]thiophene-2-sulfonylamino)-2-oxo-pyrrolidin-1-ylmethyl]-benzamidine trifluoroacetate;
([3-[3-(S)-(4,6-Dichlorobenzo[b]thiophene-2-sulfonylamino)-2-oxo-pyrrolidin-1-ylmethyl]-phenyl]-iminomethyl)-carbamic acid 2,2,2-trichloroethyl ester;
4-Amino-3-[3-(S)-(4,6-dichlorobenzo[b]thiophene-2-sulfonylamino)-2-oxo-pyrrolidin-1-ylmethyl]-benzamidine trifluoroacetate;
4-Hydroxy-3-[3-(S)-(4,6-dichlorobenzo[b]thiophene-2-sulfonylamino)-2-oxo-pyrrolidin-1-ylmethyl]-benzamidine trifluoroacetate;
3-[3-(S)-(6-Fluorobenzo[b]thiophene-2-sulfonylamino)-2-oxo-pyrrolidin-1-ylmethyl]-benzamidine trifluoroacetate;
4-Amino-3-[3-(S)-(6-fluorobenzo[b]thiophene-2-sulfonylamino)-2-oxo-pyrrolidin-1-ylmethyl]-benzamidine trifluoroacetate;
4-Hydroxy-3-[3-(S)-(6-fluorobenzo[b]thiophene-2-sulfonylamino)-2-oxo-pyrrolidin-1-ylmethyl]-benzamidine trifluoroacetate;
4-Amino-3-[3-(S)-(4-chlorobenzo[b]thiophene-2-sulfonylamino)-2-oxo-pyrrolidin-1-ylmethyl]-benzamidine trifluoroacetate;
4-Hydroxy-3-[3-(S)-(4-chlorobenzo[b]thiophene-2-sulfonylamino)-2-oxo-pyrrolidin-1-ylmethyl]-benzamidine trifluoroacetate;
3[-3-(S)-(4-Chloro-thieno[3,2-c]pyridine-2-sulfonylamino)-2-oxo-pyrrolidin-1-ylmethyl]-benzamidine trifluoroacetate;
4-Hydroxy-3-[3-(S)-(4-chloro-thieno[3,2-c]pyridine-2-sulfonylamino)-2-oxo-pyrrolidin-1-ylmethyl]-benzamidine trifluoroacetate;
3-[3-(S)-(5-Chlorothieno[3,2-b]pyridine-2-sulfonylamino)-2-oxo-pyrrolidin-1-ylmethyl]-benzamidine trifluoroacetate;
3-[3-(S)-(Thieno[3,2-b]pyridine-2-sulfonylamino)-2-oxo-pyrrolidin-1-ylmethyl]-benzamidine bistrifluoroacetate;
3-[3-(S)-(5-Chlorothieno[3,2-b]pyridine-2-sulfonylamino)-2-oxo-pyrrolidin-1-ylmethyl]-hydroxybenzamidine trifluoroacetate;
3-{3-(S)-[(5-Chlorothieno[3,2-b]pyridine-2-sulfonyl)-methylamino]-2-oxo-pyrrolidin-1-ylmethyl}-benzamidine trifluoroacetate;
3-[3-(S)-(6-Chlorothieno[3,2-b]pyridine-2-sulfonylamino)-2-oxo-pyrrolidin-1-ylmethyl]-benzamidine trifluoroacetate;
3-[3-(S)-(Thieno[3,2-b]pyridine-2-sulfonylamino)-2-oxo-pyrrolidin-1-ylmethyl]-benzamidine bistrifluoroacetate;
3-{3-(S)-(6-Chlorothieno[3,2-b]pyridine-2-sulfonyl)-methylamino)-2-oxo-pyrrolidin-1-ylmethyl}-benzamidine trifluoroacetate;
4-Hydroxy-3-[2-oxo-3-(S)-(S)-(5-Chlorothieno[3,2-b]pyridine-2-sulfonylamino)-2-oxo-pyrrolidin-1-ylmethyl}-benzamidine trifluoroacetate;
4-Hydroxy-3-[2-oxo-3-(S)-thieno[3,2-b]pyridine-2-sulfonylamino)-2-oxo-pyrrolidin-1-ylmethyl]-benzamidine trifluoroacetate;
4-Hydroxy-3-[2-oxo-3-(S)-(5-chlorothieno[3,2-b]pyridine-2-sulfonylamino)-2-oxo-pyrrolidin-1-ylmethyl]-hydroxybenzamidine trifluoroacetate;
4-Amino-3-[2-oxo-3-(S)-(5-chlorothieno[3,2-b]pyridine-2-sulfonylamino)-2-oxo-pyrrolidin-1-ylmethyl]-benzamidine trifluoroacetate;
4-Amino-3-[2-oxo-3-(S)-(thieno[3,2-b]pyridine-2-sulfonylamino)-2-oxo-pyrrolidin-1-ylmethyl]-benzamidine bistrifluoroacetate;
4-[3-(S)-(5-Chlorothieno[3,2-b]pyridine-2-sulfonylamino)-2-oxo-pyrrolidin-1-ylmethyl]-thiophene-2-carboxamidine trifluoroacetate;
4-[3-(S)-(5-Chlorothieno[3,2-b]pyridine-2-sulfonylamino)-2-oxo-pyrrolidin-1-ylmethyl]-thiophene-2-hydroxycarboxamidine trifluoroacetate;
4-{3-(S)-(5-Chlorothieno[3,2-b]pyridine-2-sulfonyl)-methylamino]-2-oxo-pyrrolidin-1-ylmethyl}-thiophene-2-carboxamidine trifluoroacetate;
3-{3-(S)-[5-(2-Methylsulfanyl-pyrimidin-4-yl)-thiophene-2-sulfonylamino]-2-oxo-pyrrolidin-1-ylmethyl}-benzamidine trifluoroacetate;
3-{3-(S)-[5-(2-Methoxy-pyrimidin-4-yl)-thiophene-2-sulfonylamino]-2-oxo-pyrrolidin-1-ylmethyl}-benzamidine trifluoroacetate;
3-{3-(S)-[5-(2-Amino-pyrimidin-4-yl)-thiophene-2-sulfonyl]-methylamino)-2-oxo-pyrrolidin-1-ylmethyl}-benzamidine trifluoroacetate;
3-{3-(S)-([5-(2-Amino-pyrimidin-4-yl)-thiophene-2-sulfonyl]-methylamino)-2-oxo-pyrrolidin-1-ylmethyl}-benzamidine bistrifluoroacetate;
3-[3-(S)-(5'-Chloro-[2,2'-bithiophenyl-5-sulfonylamino)-2-oxo-pyrimidin-1-ylmethyl])-benzamidine trifluoroacetate;
4-Amino-3-[3-(S)-benzo[b]thiophene-2-sulfonylamino)-2-oxopyrrolidin-1-ylmethyl]benzamidine trifluoroacetate;
4-Amino-3-[6chlorobenzo[b]thiophene-2-sulfonylamino)-2-oxopyrrolidin-1-ylmethyl]-benzamidine trifluoroacetate;
4-Amino-3-[6-chlorobenzo[b]thiophene-2-sulfonylamino)-2-oxopyrrolidin-1-ylmethyl]-hydroxybenzamidine trifluoroacetate;
3-[2-Oxo-3-(S)-(5-pyridin-3-yl-thiophene-2-sulfonylamino)-pyrrolidin-1-ylmethyl]-benzamidine trifluoroacetate;
4-Amino-3-[2-oxo-3-(S)-(5-pyridin-3-yl-thiophene-2-sulfonylamino)-pyrrolidin-1-ylmethyl]-benzamidine trifluoroacetate;

4-Hydroxy-3-[2-oxo-3-(S)-(5-pyridin-3-yl-thiophene-2-sulfonylamino)-pyrrolidin-1-ylmethyl]-benzamidine trifluoroacetate;

4-Hydroxy-3-[2-oxo-3-(S)-(5-pyridin-N-oxide-3yl-thiophene-2-sulfonylamino)-pyrrolidin-1-ylmethyl]-benzamidine trifluoroacetate;

3-[2-Oxo-3-(S)-(5-pyridin-4-yl-thiophene-2-sulfonylamino)-pyrimidin-1-ylmethyl])-benzamidine trifluoroacetate;

3-[3-(S)-(4-Chloro-thiophene-2-sulfonylamino)-2-oxopyrrolidin-1-ylmethyl])-benzamidine trifluoroacetate;

3-{3-(S)-[(5-(5-Chloropyridin-3-yl)-thiophene-2-sulfonylamino]-2-oxopyrrolidin-1-ylmethyl}-benzamidine trifluoroacetate;

3-[3-(S)-(4-Chloro-5-pyridin-3-ylthiophene-2-sulfonylamino)-2-oxopyrrolidin-1-ylmethyl]-benzamidine trifluoroacetate;

4-Hydroxy-3-[3-(S)-(6-chlorobenzo[b]-thiophene-2-sulfonylamino)-2-oxo-pyrrolidin-1-ylmethyl]-benzamidine trifluoroacetate;

3-[3-(S)-(1-Aminoisoquinoline-6-sulfonylamino)-2-oxopyrrolidin-1-ylmethyl]-benzamidine trifluoroacetate;

4-Fluoro-3-[3-(S)-(5-pyridin-3-yl-thiophene-2-sulfonylamino)-2-oxo-pyrrolidin-1-ylmethyl]-benzamidine trifluoroacetate;

2-Chloroquinoline-6-sulfonic acid {1-[3-(aminoiminomethyl)-benzyl]-2-oxo-pyrrolidin-3-(S)-yl}-amide trifluoroacetate;

2-Aminoquinoline-6-sulfonic acid {1-[3-(aminoiminomethyl)-benzyl]-2-oxo-pyrrolidin-3-(S)-yl}-amide bistrifluoroacetate;

4-Hydroxy-3-[3-(S)-(7-chloro-thieno[2,3-c]-pyridine-2-sulfonylamino)-2-oxo-pyrrolidin-1-ylmethyl]-benzamidine trifluoroacetate;

4-Hydroxy-3-[3-(S)-(thieno[2,3-c]pyridine-2-sulfonylamino)-2-oxo-pyrrolidin-1-ylmethyl]-benzamidine bistrifluoroacetate;

4-Hydroxy-3-[3-(S)-(thieno[3,2-c]pyridine-2-sulfonylamino)-2-oxo-pyrrolidin-1-ylmethyl]-benzamidine trifluoroacetate;

4-[3-(6-Fluorobenzo[b]-thiophene-2-sulfonylamino)-2-oxo-pyrrolidin-1-ylmethyl]-thiophene-2-carboxamidine hydrochloride;

4-{3-(S)-[3-Aminopropyl)-(6-fluorobenzo[b]thiophene-2-sulfonylamino)-2-oxo-pyrrolidin-1-ylmethyl}-thiophene-2-carboxamidine bistrifluoroacetate;

[[1-(5-Carbamimidoyl-thiophen-3-ylmethyl-2-oxo-pyrrolidin-3-yl]-(6-fluorobenzo[b]thiophen-2-sulfonyl)-amino]-acetic acid trifluoroacetate;

[Imino-(4-{3-[(7-methoxynaphthalene-2-sulfonyl)-pyridin-2-ylmethyl-amino]-2-oxo-pyrrolidin-1-ylmethyl}-thiophen-2-yl)-methyl]-carbamic acid ethyl ester;

4-Amino-3-{3-(S)-[(7-methoxy-naphthalene-2-sulfonyl)-pyridine-2-ylmethyl-amino]-2-oxo-pyrrolidin-1-ylmethyl}-benzamidine trifluoroacetate;

2-[[1-(2-Amimo-5-carbamimidoyl-benzyl)-2-oxo-pyrrolidin-3-(S)-yl}-(7-methoxy-naphthalene-2-sulfonyl)-amino]-acetamide trifluoroacetate;

[Imino-(3-{3-[(7-methoxy-naphthalene-2-sulfonyl)-methylamino]-2-oxo-3-(S)-pyrrolidin-1-ylmethyl}-4-amino-phenyl)-methyl]carbamic acid ethyl ester;

4-Hydroxy-3-{3)(S)-[5-(1-Hydroxy-pyridin-4yl)-thiophene-2-sulfonyl amino]-2-oxo-pyrrolidin-1-ylmethyl}-benzamidine trifluoroacetate;

4-Amino-3-[3-(S)-(5-chloro-thieno[3,2-b]pyridine-2-sulfonylamino)-2-oxo-pyrrolidin-1-ylmethyl]-hydroxybenzamidine trifluoroacetate;

4-Amino-3-[3-(S)-(5-methoxy-thieno[3,2-b]pyridine-2-sulfonylamino)-2-oxo-pyrrolidin-1-ylmethyl]-benzamidine bistrifluoroacetate;

3-[3-(S)-(5-Isoxazol-3-yl-thiophene-2-sulfonylamino)-2-oxo-pyrrolidin-1-ylmethyl]-benzamidine trifluoroacetate;

4-Amino-3-[3-(S)-(5-isoxazol-3yl-thiophene-2-sulfonylamino)-2-oxo-pyrrolidin-1-ylmethyl]-benzamidine trifluoroacetate;

4-Hydroxy-3-[3-(S)-(5-isoxazol-3yl-thiophene-2-sulfonylamino)-2-oxo-pyrrolidin-1-ylmethyl}-benzamidine trifluoroacetate;

3-(S)-[3-([2,2']-Bithiophenyl-5-sulfonylamino)-2-oxo-pyrrolidin-1-ylmethyl]-benzamidine trifluoroacetate;

4-Amino-3-[3-(S)-([2,2']-bithiophenyl-5-sulfonylamino)-2-oxo-pyrrolidin-1-ylmethyl]-benzamidine trifluoroacetate;

4-Amino-3-[3-(S)-(5'-chloro-[2,2']-bithiophenyl-5-sulfonylamino)-2-oxo-pyrrolidin-1-ylmethyl]-benzamidine trifluoroacetate;

4-Hydroxy-3-[3-(S)-(5'-chloro-2,2']bithiophenyl-5-sulfonylamino)-2-oxo-pyrrolidin-1-ylmethyl}-benzamidine trifluoroacetate;

4-Hydroxy-3-[3-(S)-(5'-chloro-2,2']-bithiophenyl-5-sulfonylamino)-2-oxo-pyrrolidin-1-ylmethyl]-hydroxybenzamidine; and 4-[3-(S)-(6-Fluoro-benzo[b]thiophene-2-sulfonylamino)-2-oxo-pyrrolidin-1-ylmethyl]-pyridine-2-carboxamidine hydrochloride.

More preferred species according to the invention are selected from the group consisting of 3-[3-(S)-[(Benzo[b]thiophene-2-sulfonyl)-methylamino]-2-oxo-pyrrolidin-1-ylmethyl]-benzamidine trifluoroacetate;

4-[3-(Benzo[b]thiophene-2-sulfonylamino)-2-oxo-pyrrolidin-1-ylmethyl]-thiophene-2-carboxamidine trifluoroacetate;

3-[3-(S)-(6-Chlorobenzo[b]thiophene-2-sulfonylamino)-2-oxo-pyrrolidin-1-ylmethyl]-benzamidine trifluoroacetate;

3-[3-(S)-(6-Chlorobenzo[b]thiophene-2-sulfonylamino)-2-oxo-pyrrolidin-1-ylmethyl]-benzamidine trifluoroacetate;

3-3-(4,6-Dichlorobenzo[b]thiophene-2-sulfonylamino)-2-oxo-pyrrolidin-1-ylmethyl]-benzamidine trifluoroacetate;

([3-[3-(S)-(4,6-Dichlorobenzo[b]thiophene-2-sulfonylamino)-2-oxo-pyrrolidin-1-ylmethyl]-phenyl]-iminomethyl)-carbamic acid 2,2,2-trichloroethyl ester;

3-[3-(6-Fluorobenzo[b]thiophene-2-sulfonylamino)-2-oxo-pyrrolidin-1-ylmethyl]-benzamidine trifluoroacetate;

4-Amino-3-2-oxo-3-(S)-(6-fluorobenzo[b]thiophene-2-sulfamylamino)-pyrrolidin-1-ylmethyl]-benzamidine trifluoroacetate;

4-Hydroxy-3-2-oxo-3-(S)-(6-fluorobenzo[b]thiophene-2-sulfamylamino)-pyrrolidin-1-ylmethyl]-benzamidine trifluoroacetate;

4-Hydroxy-3-[2-oxo-3-(S)-(4-chloro-thieno[3,2-c]pyridine-2-sulfamylamino)-pyrrolidin-1-ylmethyl]-benzamidine trifluoroacetate;

3-[3-(S)-(Thieno[3,2-b]pyridine-2-sulfonylamino)-2-oxo-pyrrolidin-1-ylmethyl]-benzamidine bistrifluoroacetate;

3-[3-(S)-(Thieno[2,3-b]pyridine-2-sulfonylamino)-2-oxo-pyrrolidin-1-ylmethyl]-benzamidine bistrifluoroacetate;

4-Amino-3-[2-oxo-3-(S)-(thieno[3,2-b]pyridine-2-sulfonylamino)-pyrrolidin-1-ylmethyl]-benzamidine bistrifluoroacetate;

3-{3-(S)-[5-(2-Methylsulfanyl-pyrimidin-4-yl)-thiophene-2-sulfonylamino]-2-oxo-pyrrolidin-1-ylmethyl}-benzamidine trifluoroacetate;

4-Amino-3-[6-Chlorobenzo[b]thiophene-2-sulfonylamino)-2-oxopyrrolidin-1-ylmethyl]-benzamidine trifluoroacetate;

4-Amino-3-[6-Chlorobenzo[b]thiophene-2-sulfonylamino)-2-oxopyrrolidin-1-ylmethyl]hydroxybenzamidine trifluoroacetate;

3-[2-Oxo-3-(S)-(5-pyridin-3-yl-thiophene-2-sulfonylamino)-pyrrolidin-1-ylmethyl]-benzamidine trifluoroacetate;

4-Hydroxy-3-[2-oxo-3-(S)-(5-pyridin-3-yl-thiophene-2-sulfonylamino)-pyrrolidin-1-ylmethyl]-benzamidine trifluoroacetate;

4-Hydroxy-3-[2-oxo-3-(S)-(5-pyridin-N-oxide-3-yl-thiophene-2-sulfonylamino)-pyrrolidin-1-ylmethyl]-benzamidine trifluoroacetate;

4-Hydroxy-3-[3-(S)-(6-chloro-benzo[b]thiophene-2-sulfonylamino)-2-oxo-pyrrolidin-1-ylmethyl]-benzamidine trifluoroacetate;

4-Hydroxy-3-[3-(S)-(7-chloro-thieno[2,3-c]pyridine-2-sulfonylamino)-2-oxo-pyrrolidin-1-ylmethyl]-benzamidine trifluoroacetate;

4-Hydroxy-3-[3-(S)-(thieno[2,3-c]pyridine-2-sulfonylamino)-2-oxo-pyrrolidin-1-ylmethyl]-benzamidine bistrifluoroacetate;

4-Hydroxy-3-[3-(S)-(thieno[3,2-c]pyridine-2-sulfonylamino)-2-oxo-pyrrolidin-1-ylmethyl]-benzamidine trifluoroacetate;

4-Hydroxy-3-{3-(S)-[5-(1-Hydroxy-pyridin-4yl)-thiophene-2-sulfonylamino]-2-oxo-pyrrolidin-1-ylmethyl}-benzamidine trifluoroacetate;

4-Amino-3-[3-(S)-(5-methoxy-thieno[3,2-b]pyridine-2-sulfonylamino)-2-oxo-pyrrolidin-1-ylmethyl]-benzamidine bistrifluoroacetate;

4-Amino-3-[3-(S)-(5-isoxazol-3-yl-thiophene-2-sulfonylamino)-2-oxo-pyrrolidin-1-ylmethyl]-benzamidine trifluoroacetate;

4-Hydroxy-3-[3-(S)-(5-isoxazol-3yl-thiophene-2-sulfonylamino)-2-oxo-pyrrolidin-1-ylmethyl]-benzamidine trifluoroacetate;

4-Amino-3-[3-(S)-([2,2']-bithiophenyl-5-sulfonylamino)-2-oxo-pyrrolidin-1-ylmethyl]-benzamidine trifluoroacetate;

4-Amino-3-[3-(S)-(5'-chloro-[2,2']-bithiophenyl-5-sulfonylamino)-2-oxo-pyrrolidin-1-ylmethyl]-benzamidine trifluoroacetate; and 4-Hydroxy-3-[3-(S)-(5'-chloro-[2,2']-bithiophenyl-5-sulfonylamino)-2-oxo-pyrrolidin-1-ylmethyl}-benzamidine hydrochloride.

This invention also encompasses all combinations of preferred aspects of the invention noted herein.

Compounds of formula I may be prepared by the application or adaptation of known methods, by which is meant methods used heretofore described in the literature.

Compounds of formula I can be prepared by treatment of compounds of formula II

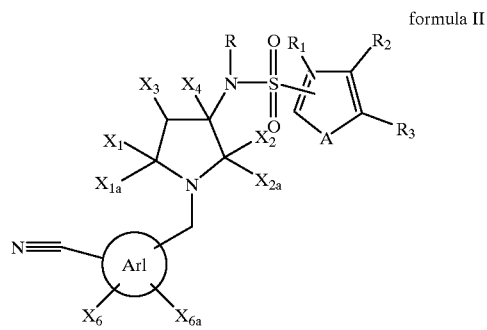

formula II in an alcoholic solvent such as ethanol with or without a co-solvent such as $CH_2Cl_2$ with a hydrogen halide gas such as HCl at about −40° C. to about 100° C. The resulting imidate is then treated in an alcoholic solvent (such as MeOH) with ammonia gas to give compounds of formula I in which $R_4$=H and $X_5$ and $X_{5a}$ taken together are =$NR_5$ where $R_5$ is H(amidine). For those compounds in which $R_5$=OH, the imidate is treated with hydroxylamine in an alcoholic solvent. For compounds in which $R_5$=C(O)OR$_6$, the amidine is dissolved in a DMF/$CH_2Cl_2$ solution followed by treatment with a teritiary amine base such as triethylamine, diisopropylethylamine or N-methylpiperidine and an alkyl carbonate or an alkyl chloroformate at about −20° C. to about 100° C. Compounds of formula II in which R does not equal H can be produced by treatment of compounds of formula III

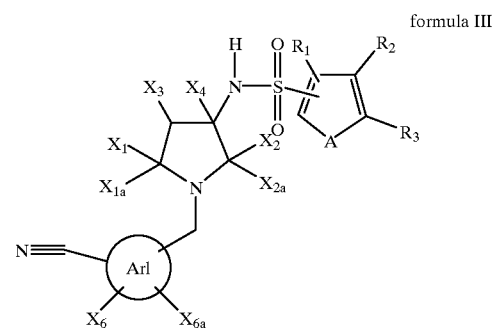

formula III in an inert organic solvent, such as THF, DMF, or $Et_2O$, with a strong base such as sodium hydride or potassium carbonate, followed by the addition of an optionally substituted alkyl halide, optionally substituted aralkyl halide, or an optionally substituted heteroaralkyl halide at temperatures about −78° C. to about 100° C. Compounds of formula III can be prepared from amines of formula IV

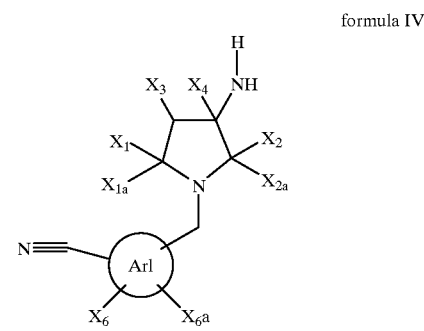

formula IV by either dissolving the amine hydrochloride in an organic solvent such as $CH_2Cl_2$, THF or DMF containing an appropriate base such as triethylamine or potassium carbonate or by dissolving the amine hydrochloride in an organic base such as pyridine followed by addition of a sulfonyl chloride represented by formula V.

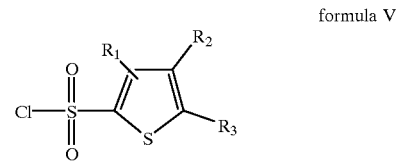

formula V

Sulfonyl chlorides represented by formula V can be produced by treatment of compounds represented by formula VI

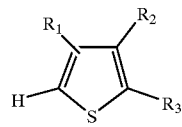

formula VI with a strong base such as n-BuLi at −78° C. followed by the addition of SO$_2$ gas and treatment of the lithium heteroaryl sulfonate with a chlorinating agent such as NCS or SO$_2$Cl$_2$. Compounds of formula IV in which

is a phenyl group substituted as follows:

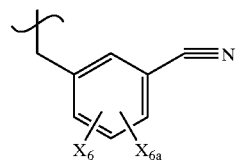

can be prepared by the treatment of compounds of formula VII in which P is a standard protecting moiety such as benzyl, t-butyl, allyl, silylethyl, or trichloroethyl, formula VII

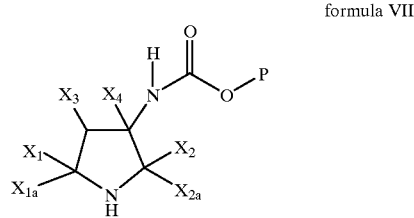

with a methyl halide represented by compounds of formula VIII formula VIII

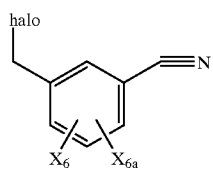

in an inert organic solvent such as THF, ET$_2$O or DMF in the presence of a strong base such as NaH, lithium hexamethyldisilylazide or lithium diisopropylamine. The carbonate protecting groups is then removed by one of the following appropriate deprotection methods such as acidic, basic, hydrogenolysis, palladium mediated deprotection, zinc promoted deprotection or fluoride anion mediated deprotection. Compounds of formula VIII can be prepared by treating compounds of formula IX

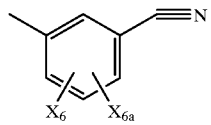

formula IX with a chlorinating or brominating agent such as NCS or NBS. When $X_6$=NH$_2$ and $X_{6a}$ is H, the corresponding nitro compound is reduced using SnCl$_2$ and protected as a disubstituted alkyl or aryl or aralkyl imine. The resulting protected material is brominated using NBS to give a compound represented by formula VIII. When $X_6$=OH and $X_{6a}$ is H, the hydroxyl group is protected as silyl, MOM- or MEM-group. The resulting compound is then brominated using NBS. Compounds of formula IV in which

is thienyl group substituted as shown below;

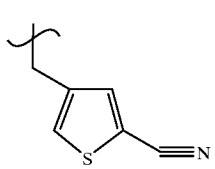

can be prepared by reaction of a bromine or iodine containing thiophene carboxaldehyde with a reducing reagent such as sodium borohydride or lithium borohydride. The resulting bromine or iodine containing thiophene methanol is then converted to the nitrile using a palladium mediated coupling reaction with a cyanide source such as Zn(CN)$_2$. The resulting cyano-thiophene-methanol is then converted to the corresponding methylchloride or methylbromide using PPh$_3$ with CCl$_4$ or CBr$_4$.

Compounds of formula IV in which X$_3$=H can be obtained by commercial sourced or literature sources or by the treatment of a protected optionally substituted diamino alkyl carboxylic acid, in which the protection is at the amino attached to the carbon bearing the carboxylic acid, with peptide coupling reagents such as EDC (1-3-Dimethylaminopropyl)-3-ethylcarbodiimide hydrochloride), DCC (1,3-Dicyclohexylacarbodiimide) or BOP (Benzotriazol-1-yloxytris(dimethylamino) phosphonium hexafluorophosphate) in an inert solvent such as CH$_2$Cl$_2$, THF or DMF. Compounds in which X$_3$=alkyl can be prepared using methods similar to those described by J. E. Baldwin et al, Tetrahedron 46 (13), p 4733, 1990.

A compound of formula I including an heteroaryl group containing one or more nitrogen ring atoms, preferably imine (=N—), may be converted to the corresponding compound wherein one or more nitrogen ring atom of the heteroaryl moiety is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, trifluoroacetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, trifluoroacetate, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compound of this invention are prepared either by dissolving the free base in aqueous or aqueous-alcohol solution or other suitable solvents containing the appropriate acid and isolating the slat by evaporating the solution, or by reacting the free base and acid in an organic solvent, in which case the salt separates directly or an be obtained by concentration of the solution.

The compounds of this invention may be regenerated from the acid addition salts by the application or adaptation of known methods. For example, parent compound of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on the activity of Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, diethylamine, N-benzylphenethylamine, piperazine, tris(hydroxymethyl) aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic either such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Salt forms according to invention also include compounds having a quarternarized nitrogen. The quarternarized salts are formed by methods such as by alkylation of a $sp^3$ and $sp^2$ hybridized nitrogen in the compounds.

As will be self-evident to those skilled in the art, some of the compounds of this invention do not form stable salts. However, acid addition salts are most likely to be formed by compounds of this invention having a nitrogen containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds of the present invention may contain asymmetric centers. These asymmetric centers may independently be in either the R or S configuration. It will also be apparent to those skilled in the art that certain compounds of formula I may exhibit geometrical isomerism. Geometrical isomers include the cis and trans forms of compounds of the invention having alkenyl or diazenyl (azo) moieties. The present invention comprises the individual geometrical isomers and stereoisomers and mixtures thereof. Compounds of the present invention may also contain tautomeric structures, e.g.,

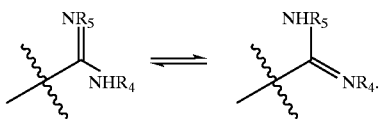

The present invention comprises the various tautomeric structures and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents.

The present invention is further exemplified but not limited by the following examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad, bs=broad singlet, q=quartet, AB=AB pattern.

EXAMPLE 1

3-[3-(S)-(Benzol[b]thiophene-2-sulfonylamino)-2-oxo-pyrrolidin-1-ylmethyl]-benzamidine trifluoroacetate A. (2-Oxo-pyrrolidin-3-(S)-yl)-carbamic acid tert-butyl ester.

(S)-Boc-Diaminobutyric acid (25 g, 115 mmol), triethylamine (35 g, 344 mmol), and 1-hydroxybenzotriazole hydrate (19.3 g, 143 mmol) are dissolved in 300 mL of THF. 1-(3-Dimethylaminopropyl)-3-ethylcarbodiimide hydrochloride (27.4 g, 143 mmol) is added to the solution. The solution is heated at 60° C. over 15 minutes. A white precipitate forms and the solution is kept at 60° C. for 4 hours. After this time, the solution is filtered and the collected liquid is concentrated. The crude product is purified by column chromatography eluting with a gradient of 1% MeOH/$CH_2Cl_2$ to 3% MeOH/$CH_2Cl_2$ to afford the title compound (19.6 g, 98 mmol) as a white solid.

$^1$H NMR (CDCl$_3$, 300 MHz)δ 6.17 (bs, 1H), 5.08 (bs, 1H), 4.12 (m, 1H), 3.33 (m, 2H), 2.65 (m, 1H), 2.00 (m, 1H), 1.42 (s, 9H).

B. [1-(3-Cyanobenzyl)-2-oxo-pyrrolidin-3-(S)-yl]-carbamic acid tert-butyl ester.

To a solution of 2-oxo-pyrrolidin-3-(S)-yl)-carbamic acid tert-butyl ester (9.0 g, 45 mmol) and α-bromo-m-toluoyl nitrile (9.3 g, 47 mmol) in 225 mL of THF/DMF (10:1) at 0° C. is added a 60% mineral oil dispersion of sodium hydride (1.8 g, 46 mmol). The reaction mixture is stirred at 0° C. for 0.5 hour and then allowed to warm to ambient temperatures. After 3 hours, the reaction mixture is quenched by the addition of saturated NH$_4$Cl. The resulting solution is diluted with EtOAc. The layers are separated. The organic layer is washed with 1N HCl, H$_2$O and saturated NaCl. The organic layer is dried over MgSO$_4$, filtered and concentrated. The crude product is purified by column chromatography eluting with a gradient of 20% EtOAc/hexanes to 40% EtOAc/hexanes to afford the title compound (12.7 g, 40 mmol) as a white solid.

$^1$H NMR (CDCl$_3$, 300 MHz)δ 7.55 (m, 4H), 5.18 (bs, 1H), 4.47 (AB, 2H), 4.18 (dd, 1H), 3.21 (m, 2H), 2.60 (m, 1H), 1.42 (s, 9H).

C. 3-(3-(S)-Amino-2-oxo-pyrrolidin-1-ylmethyl)-benzonitrile hydrochloride.

To a solution of [1-(3-cyanobenzyl)-2-oxo-pyrrolidin-3-(S)-yl]-carbamic acid tert-butyl ester (9.1 g, 29 mmol) in 150 mL of EtOAc at 0° C. is bubbled HCl gas for 10 minutes. After this time, the solution is stirred for 4 hours. The solution is then concentrated to afford the title compound (7.3 g, 29 mmol) as a white solid. $^1$H NMR (DMSO-d$_6$, 300 MHz)δ 8.71 (bs, 3H), 7.85 (m, 2H), 7.70 (m, 2H), 4.58 (AB, 2H), 4.13 (M, 1H), 3.32 (m, 2H), 2.44 (m, 1H), 2.18 (m, 1H).

D. Benzo[b]thiophene-2-sulfonyl chloride.

To a solution of thianaphthalene (11.8 g, 88.1 mmol), in 400 mL of THF at −78° C. is added n-BuLi (55 mL of a 1.6M solution in hexanes, 88.1 mmol). After 15 minutes, the solution is added by cannula to a precooled (−78° C.) solution of SO$_2$(200 g) in 100 mL of THF. After addition, the solution is allowed to warm to ambient temperatures. After 0.5 hour, the solution is concentrated. The residue is suspended in hexanes (400 mL) and is cooled to 0° C. To the solution is added SO$_2$Cl$_2$ (12.5 g, 92.5 mmol). After stirring for 15 minutes, the solution is concentrated. The residue is dissolved in EtOAc. The organic solution is washed with saturated NH$_4$Cl (aq.), H$_2$O and saturated NaCl (aq.). The organic layer is dried over MgSO$_4$, filtered and concentrated. The crude product is dissolved in CH$_2$Cl$_2$ and filtered through a plug of silica gel. The organic solution is then concentrated. The resulting solid is triturated with hexanes to give the title compound (12.1 g, 38 mmol) as a white solid.

$^1$H NMR (CDCl$_3$, 300 MHz)δ 8.16 (s, 1H), 7.97 (m, 2H), 7.57 (m, 2H),

E. Benzo[b]thiophene-2-sulfonic acid 1-(3-cyanobenzyl)-2-oxo-pyrrolidin-3-(S)-yl]-amide.

To a solution of 3-(3-(S)-amino-2-oxo-pyrrolidin-1-ylmethyl)-benzonitrile hydrochloride (0.36 g, 1.43 mmol) in 15 mL of CH$_2$Cl$_2$ is added benzo[b]thiophene-2-sulfonyl chloride (0.32 g, 1.38 mmol). To the resulting solution is added triethylamine (0.29 g, 2.88 mmol). After 16 hours, the solution is diluted with EtOAc. The solution is washed with 1N HCl, saturated NaHCO$_3$, and saturated NaCl. The organic layer is dried over MgSO$_4$, filtered and concentrated. The title compound (0.45 g, 1.09 mmol) is obtained as white solid.

$^1$H NMR (CDCl$_3$, 300 MHz)7.95 (m, 2H), 7.62 (m, 1H), 7.42 (m, 6H), 5.49 (bs, 1H), 4.47 (AB, 2H), 3.90 (m, 1H), 3.24 (m, 2H), 2.63 (m, 1H), 2.10 (m, 1H).

F. 3-[3-(S)-(Benzo[b]thiophene-2-sulfonylamino)-2-oxo-pyrrolidin-1-ylmethyl]-benzamidine trifluoracetate.

To a solution of benzo[b]thiophene-2-sulfonic acid [1-(3-cyano-benzyl)-2-oxo-pyrrolidin-3-yl]-amide (0.20 g, 0.49 mmol) in 20 mL of EtOH:CH$_2$Cl$_2$(1:1) at 0° C. is bubbled HCl gas for 5 minutes. The solution is then allowed to warm to ambient temperatures. After 16 hours, the solution is concentrated. The residue is dissolved in 20 mL of MeOH and NH$_3$ gas is bubbled through the solution for 5 minutes. After this time, the solution is heated at 60° C. After 2 hours, the solution is concentrated. The residue is purified by RP-HPLC eluting with a gradient of 10% CH$_3$CN/H$_2$O (0.1% TFA) to 80% CH$_3$CN/H$_2$O (0.1% TFA). The appropriate fractions are lyophilized to provide the title compound as a solid.

¹H NMR (DMSO, 300 MHz) δ 9.28 (bs, 2H), 9.02 (bs, 2H), 8.62 (m, 2H), 8.04 (s, 1H), 8.02 (m, 3H), 7.65 (m, 1H), 7.51 (m, 5H), 4.40 (AB, 2H), 4.22 (m, 1H), 3.09 (m, 2H), 2.14 (m, 1H), 1.68 (m, 1H). FAB MS, [M+H]⁺=4.79. Elemental analysis calculated with 1.5 mole of TFA: C=46.07%, H=3.62%, N=9.35%; found: C=46.35%, H=3.83%, N=9.46%.

EXAMPLE 2

3-[3-(S)-[(Benzo[b]thiophene-2-sulfonyl)-methylamino]-2-oxo-pyrrolidin-1-ylmethyl]-benzamidine trifluoroacetate A. Benzo[b]thiophene-2-sulfonic acid [1-(3-cyanobenzyl)-2-oxo-pyrrolidin-3-(S)-yl]-methylamide.

To a solution of benzo[b]thiophene-2-sulfonic acid [1-(3-cyano-benzyl)-2-oxo-pyrrolidin-3-(S)-yl]-amide (0.25 g, 0.61 mmol) in 3mL of DMF is added methyl iodide (0.13 g, 0.91 mmol) followed by $K_2CO_3$ (0.13 g, 0.91 mmol). The solution is stirred at ambient temperatures for 6 hours. After this time, the solution is diluted with $H_2O$ and EtOAc. The layers are separated. The organic layer is washed with $H_2O$ and saturated NaCl. The organic layer is dried over $MgSO_4$, filtered and concentrated. The residue is triturated with $Et_2O$ to give the title compound (0.25 g, 0.59 mmol) as a white solid.

¹H NMR (CDCl₃, 300 MHz) 7.99 (s, 1H), 7.82 (m, 2H), 7.54 (m, 1H), 7.38 (m, 5H), 4.89 (m, 1H), 4.40 (AB, 2H), 3.18 (m, 2H), 2.89 (s, 3H), 2.32 (m, 1H), 1.98 (m, 1H).

B. 3-[3-(S)-[(Benzo[b]thiophene-2-sulfonyl)-methylamino]-2-oxo-pyrrolidin-1-ylmethyl]-benzamidine trifluoroacetate.

The title compound is prepared as described in EXAMPLE 1, Part F using benzo[b]thiophene-2-sulfonic acid [1-(3-cyanobenzyl)-2-oxo-pyrrolidin-3-(S)-yl]-methylamide as the starting material. The crude product is purified by RP-HPLC eluting with a gradient of 10% $CH_3CN/H_2O$ (0.1% TFA) to 80% $CH_3CN/H_2O$ (0.1% TFA). The appropriate fractions are lyophilized to provide the title compound as a white solid.

¹H NMR (DMSO-d₆, 300 MHz) δ 9.30 (bs, 2H), 9.05 (bs, 2H), 8.07 (m, 2H), 8.00 (m, 1H), 7.65 (m, 1H), 7.53 (m, 5H), 4.93 (m, 1H), 4.42 (AB, 2H), 3.16 (m, 2H), 2.81 (s, 3H), 2.08 (m, 1H), 1.89 (m, 1H). FAB MS, [M+H]⁺=443. Elemental analysis calculated with 1.5 mole of $H_2O$: C=47.34%, H=4.15%, N=9.35%; found: C=47.26%, H=4.15%, N=9.35%.

EXAMPLE 3

4-[3-(S)-(Benzo[b]thiophene-2-sulfonylamino)-2-oxo-pyrrolidin-1-ylmethyl]-thiophene-2-carboxamidine trifluoroacetate A. 5-Iodo-thiophene-3-carboxaldehyde.

To a solution of thiophene-3-carboxaldehyde (36 g, 321 mmol) in 80 mL of $CCl_4$ and 60 mL of $H_2O$ is added 2.5 mL of conc. $H_2SO_4$ in 160 mL of acetic acid. To the resulting solution is added $HIO_3$ (14 g, 80 mmol) and $I_2$ (38 g, 150 mmol). The solution is refluxed for 6 hours. After this time, the reaction is cooled to ambient temperatures and 200 mL of $CHCl_3$ is added. The layers are separated. The aqueous layer is extracted with $CHCl_3$. The organic layers are combined and washed with 0.5M $Na_2S_2O_3$, saturated $NaHCO_3$ and saturated NaCl. The organic layer is dried over $MgSO_4$, filtered and concentrated. The crude product is purified by column chromatography eluting with gradient of 2% EtOAc/hexanes to 5% EtOAc/hexanes to afford the title compound (20 g, 84 mmol) as a white solid.

¹H NMR (CDCl₃, 300 MHz) δ 9.78 (s, 1H), 8.10 (s, 1H), 7.69 (s, 1H).

B. (5-Iodo-thiophen-3yl)methanol.

To a solution of 5-iodo-thiophen-3-carboxaldehyde (42 g, 176 mmol) in 800 mL of THF is added NaBH₄ (7.0 g, 1.85 mmol). After 1 hour, the reaction is quenched by the addition of 100 mL of sat. NH₄Cl. The resulting solution is diluted with 1 L of EtOAc. The layers are separated. The organic layer is washed with $H_2O$ and saturated NaCl. The organic layer is dried over $MgSO_4$, filtered and concentrated. The title compound (42 g, 175 mmol) is obtained as an oil.

¹H NMR (CDCl₃, 300 MHz) δ 7.18 (s, 2H), 4.63 (s, 2H), 1.92 (bs, 1H).

C. 4-Hydroxymethyl-thiophene-2-carbonitrile.

To a solution of (5-iodo-thiophen-3yl)methanol (42 g, 176 mmol) in 150 mL of DMF is added zinc cyanide (12.4 g, 106 mmol) and tetrakis(triphenylphospine)palladium (0) (8.13 g, 7.04 mmol). The solution is heated to 80° C. After 6 hours, the solution is diluted with 3 L of EtOAc. The resulting solution is washed with 1N NH₄OH, $H_2O$ and sat. NaCl. The organic layer is dried over $MgSO_4$, filtered and concentrated. The crude product is purified by column chromatography eluting with gradient of 20% EtOAc/hexanes to 30% EtOAc/hexanes to afford the title compound (10 g, 72 mmol) as a clear oil.

¹H NMR (CDCl₃, 300 MHz) δ 7.59 (s, 1H), 7.46 (s, 1H), 4.67 (s, 2H), 2.42 (bs, 1H).

D. 4-Bromomethyl-thiophene-2carbonitrile.

To a solution of 4-hydroxymethyl-thiophene-2-carbonitrile (10 g, 72 mmol), in 360 mL of THF is added triphenyl phosphine (18.3 g, 76 mmol) and carbon tetrabromide (25 g, 76 mmol). After 3 hours, the solution is filtered and concentrated. The crude product is purified by column chromatography eluting with gradient of 5% EtOAc/hexanes to 10% EtOAc/hexanes to afford the title compound (14 g, 69 mmol) as a white solid.

¹H NMR (CDCl₃, 300 MHz) δ 7.62 (s, 1H), 7.49 (s, 1H), 4.42 (s, 2H).

E. [1-(5-Cyanothiophen-3-ylmethyl)-2-oxo-pyrrolidin-3-(S)-yl]-carbamic acid tert-butyl ester.

To a solution if (2-oxo-pyrrolidin-3-(S)-yl)-carbamic acid tert-butyl ester (3.2 g, 16 mmol), prepared as described in EXAMPLE 1, Part A in 80 mL of THF:DMF (10:1) at 0° C. is added 4-bromomethyl-thiophene-2-carbonitrile (3.23 g, 16 mmol) and sodium hydride (60% dispersion in oil, 0.67 g, 16.8 mmol). After addition, the solution was allowed to warm to ambient temperatures. After 2 hours, the solution is quenched by the addition of sat. NH₄Cl. The solution is diluted with $H_2O$ and EtOAc. The layers are separated. The organic layer is washed with $H_2O$ and sat. NaCl. The organic layer is dried over $MgSO_4$, filtered and concentrated. The crude product is purified by column chromatography eluting with gradient of 20% EtOAc/$CH_2Cl_2$ to 30% EtOAc/$CH_2Cl_2$ to afford the title compound (4.0 g, 13.8 mmol) as a white solid.

¹H NMR (CDCl₃, 300 MHz) δ 7.51 (s, 1H), 7.45 (s, 1H), 5.12 (bs, 1H), 4.42 (AB, 2H), 4.12 (m, 1H), 3.27 (m, 2H), 2.58 (m, 1H), 1.93 (m, 1H), 1.42 (s, 9H).

F. 4-(3-(S)-Amino-2-oxo-pyrrolidin-1-ylmethyl)-thiophene-2-carbonitrile hydrochloride

[1-(5-Cyanothiophen-3-ylmethyl)-2-oxo-pyrrolidin-3-(S)-yl]-carbamic acid tert-butyl ester (4.0 g, 13.8 mmol) is added to a solution of 100 mL of EtOAc saturated with HCl gas at 0° C. After 3 hours, the solution is concentrated. The title compound (3.3 g, 13.5 mmol) is obtained as a white solid.

¹H NMR (DMSO-d₆, 300 MHz)δ 8.61 (bs, 3H), 7.96 (s, 1H), 7.82 (s, 1H), 5.12 (bs, 1H), 4.42 (AB, 2H), 4.00 (m, 1H), 3.27 (m, 2H), 2.31 (m, 1H), 2.03 (m, 1H).

G. Benzo[b]thiophene-2-sulfonic acid [1-(5-cyanothiophen-3-ylmethyl)-2-oxo-pyrrolidin-3-(S)-yl]-amide.

The title compound is prepared as described in EXAMPLE 1, Part E, substituting 4-(3-(S)-amino-2-oxo-pyrrolidin- 1-ylmethyl)benzonitrile hydrochloride. The crude product is triturated from Et₂O to give the product as a white solid.

¹H NMR (CDCl₃, 300 MHz)δ 7.91 (m, 3H), 7.42 (m, 3H), 7.38 (s, 1H), 5.50 (bs,1H), 4.42 (AB, 2H), 3.89 (m, 1H), 3.27 (m, 2H), 2.66 (m, 1H), 2.13 (m, 1H).

H. 4-[3-(S)-(Benzo[b]thiophene-2-sulfonylamino)-2-oxo-pyrrolidin-1-ylmethyl]-thiophene-2-carboxamidine trifluoroacetate.

The title compound is prepared as described in EXAMPLE 1, Part F using benzo[b]thiophene-2-sulfonic acid [1-(5-cyanothiophen-3-ylmethyl)-2-oxo-pyrrolidin-3-(S)-yl]-amide as the starting material. The crude product is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz)δ 9.20 (bs, 2H), 8.80 (bs, 2H), 8.55 (m, 1H), 8.00 (m, 3H), 7.86 (s, 1H), 7.78 (s, 1H), 7.46 (m, 2H), 4.37 (AB, 2H), 4.16 (m, 1H), 3.12 (m, 2H), 2.11 (m, 1H), 1.64 (m, 1H). FAB MS, [M+H]⁺=435.

EXAMPLE 4

4-[3-(S)-[(Benzo[b]thiophene-2-sulfonyl]-methylamino]-2-oxo-pyrrolidin-1ylmethyl]-thiophene-2-carboxamidine trifluoroacetate A. Benzo[b]thiophene-2-sulfonic acid [1-(5-cyanothiophen-3-ylmethyl)-2-oxo-pyrrolidin-3-(S)-yl]-methylamide.

The title compound is prepared as descried in EXAMPLE 2, Part A substituting benzo[b]thiophene-2-sulfonic acid [1-(5-cyanothiophen-3-ylmethyl)-2-oxo-pyrrolidin-3-(S)-yl]-amide for benzo[b]thiophene-2-sulfonic acid [1-(3-cyanobenzyl)-2-oxo-pyrrolidin-3-(S)-yl]-amide. The crude product is triturated with Et₂O to give the product as a white solid.

¹H NMR (CDCl₃, 300 MHz)δ 7.98 (s, 1H), 7.87 (m, 2H), 7.42 (m, 4H), 7.38 (s, 1H), 4.86 (dd, 1H), 4.38 (AB, 2H), 3.22 (m, 2H), 2.89 (m, 3H), 2.36 (m, 1H), 2.03 (m, 1H).

B. 4-[3-(S)-[(Benzo[b]thiophene-2-sulfonyl]-methylamino]-2-oxo-pyrrolidin-1ylmethyl]-thiophene-2-carboxamidine trifluoroacetate.

The title compound is prepared as described in EXAMPLE 1, Part F using benzo[b]thiophene-2-sulfonic acid [1-(5-cyanothiophen-3ylmethyl)-2-oxo-pyrrolidin-3-(S)-yl]-methylamide as the starting material. The crude product is purified by RP-HPLC eluting with a gradient of 10% CH₃CN/H₂O (0.1% TFA) to 70% CH₃CN/H₂O (0.1% TFA). The appropriate fractions are lyophilized to provide the title compound as a white solid.

¹H NMR (DMSO-d₆, 300 MHz)δ 9.30 (bs, 2H), 9.05 (bs, 2H), 8.07 (m, 2H), 8.00 (m, 1H), 7.65 (m, 1H), 7.53 (m, 5H), 4.93 (m, 1H), 4.42 (AB, 2H), 3.16 (m, 2H), 2.78 (s, 3H), 2.08 (m, 1H), 1.89 (m, 1H). FAB MS, [M+H]⁺=449. Elemental analysis calculated with 1.5 mole of H₂O: C=42.78%, H=4.10%, N=9.50%; found: C=42.83%, H=3.71%, N=9.27%.

EXAMPLE 5

3-[3-(S)-(4-Cholorobenzo[b]thiophene-2-sulfonylamino)-2-oxo-pyrrolidin-1-ylmethyl]-benzamidine trifluoroacetate A. 1-Chloro-3-(2,2-dimethoxy-ethyl-sulfanyl)-benzene.

To a solution of 3-chlorothiophenol (2.4 g, 16.6 mmol) in THF (200 mL) at 0° C. is added bromoacetaldehyde dimethyl acetal (2.8 g, 16.6 mmol). To the solution is added sodium hydride (60% mineral oil dispersion, 0.70 g, 17.4 mmol). The reaction is stirred for 16 hours, and then quenched by the addition of saturated NH₄Cl (aq.). The solution is diluted with EtOAc. The organic layer is washed with saturated NaCl (aq.). The organic layer is dried over MgSO₄, filtered and concentrated. The crude product is purified by column chromatography eluting with hexanes. The title compound (3.7 g, 15.9 mmol) is obtained as an oil.

¹H NMR (CDCl₃, 300 MHz)δ 7.32 (m, 1H), 7.25 (m, 1H), 7.12 (m, 1H), 4.47 (m, 1H), 3.07 (s, 3H), 3.02 (s, 3H).

B. 4-Chloro-benzo[b]-thiophene and 6-Chloro-benzo[b]-thiophene.

A solution containing polyphosphoric acid (8 g) and chlorobenzene (50 mL) is heated at reflux. A solution containing 1-chloro-3-(2,2-dimethoxy-ethyl-sulfanyl)-benzene (2.7 g, 11.6 mmol) in chlorobenzene (5 mL) is added dropwise to the refluxing polyphosphoric acid solution. After 6 hours, the solution is cooled to ambient temperatures. The solution is diluted with CH₂Cl₂ and washed with water and saturated NaCl (aq.). The organic layer is dried over MgSO₄, filtered and concentrated. The crude product is purified by column chromatography eluting with hexanes to yield the title compounds (2.4 g, 9.0 mmol) as a 1:1 isomeric mixture.

¹H NMR (CDCl₃, 300 MHz)δ 7.88 (m, 1H), 7.75 (m, 2H), 7.42 (m, 2H). EI MS, [M]⁺=168, 170, Cl pattern.

C. 4-Chlorobenzo[b]-thiophene-2-sulfonyl chloride and 6-Chlorobenzo[b]-thiophene-2-sulfonyl chloride The title compound is prepared as described in EXAMPLE 1, Part D substituting the 4-chloro-benzo[b]-thiophene and 6-chlorobenzo[b]-thiophene mixture for thianaphthalene. The crude product is purified by column chromatography eluting with hexanes to yield the title compound as well as 4-chlorobenzo[b]thiophene-2-sulfonyl chloride as white solids.

4-Chlorobenzo[b]thiophene-2-sulfonyl chloride

¹H NMR (CDCl₃,300 MHz) δ 8.32 (m, 1H), 7.81 (m, 1H), 7.53 (m, 2H).

6-Chlorobenzo[b]thiophene-2-sulfonyl chloride

¹H NMR (CDCl₃, 300 MHz) δ 8.11 (s, 1H), 7.88 (m, 2H), 7.50 (m, 1H).

D. 4-Chlorobenzo[b]thiophene-2-sulfonic acid [1-(3-cyano-benzyl)-2-oxo-pyrrolidin-3-(S)-yl]-amide.

The title compound is prepared as described in EXAMPLE 1, Part E, substituting 4-chlorobenzo[b]thiophene-2-sulfonyl chloride for benzo[b]thiophene-2-sulfonyl chloride. The crude product is triturated from Et₂O to give the product as a white solid.

¹H NMR (CDCl₃, 300 MHz)δ 8.09 (s, 1H), 7.73 (m, 1H), 7.58 (m, 1H), 7.46 (m, 5H), 5.76 (bs, 1H), 4.48 (AB, 2H), 3.96 (m, 1H), 3.24 (m, 2H), 2.66 (m, 1H), 2.18 (m, 1H).

E. 3-(3-(S)-Chlorobenzo[b]thiophene-2-sulfonylamino)-2-oxo-pyrrolidin-1-ylmethyl)-benzonitrile trifluoroacetate.

The title compound is prepared as described in EXAMPLE 1, Part F using 4-chlorobenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10%

CH$_3$CN/H$_2$O (0.1% TFA) to 70% CH$_3$CN/H$_2$O (0.1% TFA). The appropriate fractions are lyophilized to provide the title compound as a white solid.

$^1$H NMR (DMSO-d$_6$, 300 MHz) δ 9.28 (bs, 2H), 9.07 (bs, 2H), 8.78 (d, 1H), 8.08 (d, 1H), 8.01 (s, 1H), 7.66 (m, 1H), 7.54 (m, 5H), 4.41 (AB, 2H), 4.29 (m, 1H), 3.13 (m, 2H), 2.18 (m, 1H), 1.70 (m, 1H). FAB MS, [M+H]$^+$=463, 465, Cl pattern. Elemental analysis calculated with 1.5 mole of H$_2$O:C=43.75%, H=3.84%, N=9.28%; found: C=43.85%, H=3.50%, N=9.03%.

EXAMPLE 6

3-[3-(S)-(6-Cholorobenzo[b]thiophene-2-sulfonylamino)-2-oxo-pyrrolidin-1-ylmethyl-benzamidine trifluoroacetate A. 6-Chlorobenzo[b]thiophene-2-sulfonic acid [1-(3-cyano-benzyl)-2-oxo-pyrrolidin-3-(S)-yl]-amide.

The title compound is prepared as described in EXAMPLE 1, Part E, substituting 6-chlorobenzo[b]thiophene-2-sulfonyl chloride, prepared as described in EXAMPLE 5, Part C, for benzo[b]thiophene-2-sulfonyl chloride. The crude product is triturated from Et$_2$O to give the product as a white solid.

$^1$H NMR (CDCl$_3$, 300 MHz) δ 7.90 (s, 1H), 7.81 (m, 2H), 7.58 (m, 1H), 7.46 (m, 5H), 5.58 (bs, 1H), 4.46 (AB, 2H), 3.93 (m, 1H), 3.22 (m, 1H), 2.64 (m, 1H), 2.12 (m, 1H).

B. 3-[3-(6-Cholorobenzo[b]thiophene-2-sulfonylamino)-2-oxo-pyrrolidin-1-ylmethyl-benzamidine trifluoroacetate.

The title compound is prepared as described in EXAMPLE 1, Part F using 6-chlorobenzo[b]thiophene-2-sulfonic acid [1-(3-cyano-benzyl)-2-oxo-pyrrolidin-3yl]-amide as the starting material. The crude produce is purified by RP-HPLC eluting with a gradient of 10% CH$_3$CN/H$_2$O (0.1% TFA) to 70% CH$_3$CN/H$_2$O (0.1% TFA). The appropriate fractions are lyophilized to provide the title compound as a white solid.

$^1$H NMR (DMSO-d$_6$, 300 MHz) δ 9.28 (bs, 2H), 9.16 (bs, 2H), 8.68 (d, 1H), 8.27 (s, 1H), 8.01 (s, 1H), 7.98 (d, 1H), 7.68 (m, 1H), 7.55 (m, 5H), 4.42 (AB, 2H), 4.21 (m, 1H), 3.10 (m, 2H), 2.14 (m, 1H), 1.68 (m, 1H). FAB MS, [M+]$^+$=463, 465, Cl pattern. Elemental analysis calculated with 1.5 mole of H$_2$O: C=43.75%, H=3.84%, N=9.28%; found: C=43.85%, H=3.50%, N=9.03%.

EXAMPLE 7

3-[3-(S)-(4-Cholorobenzo[b]thiophene-2-sulfonyl)-methylamino)-2-oxo-pyrrolidin-1-ylmethyl]-benzamidine trifluoroacetate A. 4-Chlorobenzo[b]thiophene-2-sulfonic acid [1-(3-cyanobenzyl)-2-oxo-pyrrolidin-3-(S)-yl]-methylamide.

The title compound is prepared as described in EXAMPLE 2, Part A substituting 4-chlorobenzo[b]thiophene-2-sulfonic acid [1-(3-cyanobenzyl)-2-oxo-pyrrolidin-3-(S)-yl]-amide for benzo[b]thiophene-2-sulfonic acid [1-(3-cyanobenzyl)-2-oxo-pyrrolidin-3-(S)-yl]-amide. The crude product is triturated with Et$_2$O to give the product as a white solid.

$^1$H NMR (CDCl$_3$, 300 MHz) δ 8.12 (s, 1H), 7.73 (d, 1H), 7.58 (m, 1H), 7.42 (m, 5H), 4.90 (t, 1H), 4.41 (AB, 2H), 3.20 (m, 2H), 2.91 (s, 3H), 2.40 (m, 1H), 2.04 (m, 1H).

B. 3-[3-(S)-(4-Cholorobenzo[b]thiophene-2-sulfonyl)-methylamino)-2-oxo-pyrrolidin-1-ylmethyl]-benzamidine trifluoroacetate.

The title compound is prepared as described in EXAMPLE 1, Part F using 4-chlorobenzo[b]thiophene-2-sulfonic acid [1-(3-cyanobenzyl)-2-oxo-pyrrolidin-3-(S)-yl]-methylamide as the starting material. The crude product is purified by RP-HPLC eluting with a gradient of 10% CH$_3$CN/H$_2$O (0.1% TFA) to 70% CH$_3$CN/H$_2$O (0.1% TFA). The appropriate fractions are lyophilized to provide the title compound as a white solid.

$^1$H NMR (DMSO-d$_6$, 300 MHz) δ 9.28 (bs, 2H), 9.10 (bs, 2H), 8.10 (d, 1H), 8.03 (s, 1H), 7.58 (m, 1H), 7.52 (m, 5H), 4.97 (t, 1H), 4.40 (AB, 2H), 3.15 (m, 2H), 2.77 (s, 3H), 2.15 (m, 1H), 1.94 (m, 1H). FAB MS, [M+H]$^+$=477, 479, Cl pattern. Elemental analysis calculated with 1.5 mole of H$_2$O: C=44.70%, H=4.08%, N=9.06%; found: C=44.67%, H=3.66%, N=8.91%.

EXAMPLE 8

3-[3-(S)-(6-Cholorobenzo[b]thiophene-2-sulfonyl)-methylamino)-2-oxo-pyrrolidin-1-ylmethyl]-benzamidine trifluoroacetate A. 6-Chlorobenzo[b]thiophene-2-sulfonic acid [1-(3-cyanobenzyl)-2-oxo-pyrrolidin-3-(S)-yl]-methylamide.

The title compound is prepared as described in EXAMPLE 2, Part A substituting 6-chlorobenzo[b]thiophene-2-sulfonic acid [1-(3-cyano-benzyl)-2-oxo-pyrrolidin-3-(S)-yl]-amide for benzo[b]thiophene-2-sulfonic acid [1-(3-cyano-benzyl)-2-oxo-pyrrolidin-3-yl]-amide. The crude product is triturated with Et$_2$O to give the product as a white solid.

$^1$H NMR (CDCl$_3$, 300 MHz) δ 7.95 (s, 1H), 7.84 (m, 2H), 7.58 (m, 1H), 7.43 (m, 4H), 4.90 (dd, 1H), 4.41 (AB, 2H), 3.20 (m, 2H), 2.89 (s, 3H), 2.38 (m, 1H), 2.04 (m, 1H).

B. 3-[3-(S)-(6-Cholorobenzo[b]thiophene-2-sulfonyl)-methylamino)-2-oxo-pyrrolidin-1-ylmethyl]-benzamidine trifluoroacetate.

The title compound is prepared as described in EXAMPLE 1, Part F using 6-chlorobenzo[b]thiophene-2-sulfonic acid [1-(3-cyano-benzyl)-2-oxo-pyrrolidin-3-(S)-yl]-methylamide as the starting material. The crude product is purified by RP-HPLC eluting with a gradient of 10% CH$_3$CN/H$_2$O (0.1% TFA) to 70% CH$_3$CN/H$_2$O (0.1% TFA). The appropriate fractions are lyophilized to provide the title compound as a white solid.

$^1$H NMR (DMSO-d$_6$, 300 MHz) δ 9.28 (bs, 2H), 8.98 (bs, 2H), 8.29 (d, 1H), 8.12 (s, 1H), 7.99 (d, 1H), 7.65 (m, 1H), 7.52 (m, 4H), 4.89 (t, 1H), 4.40 (AB, 2H), 3.13 (m, 2H), 2.74 (s, 3H), 2.08 (m, 1H), 1.90 (m, 1H). FAB MS, [M+H]$^+$=477, 479, Cl pattern. Elemental analysis calculated with 2.0 mole of H$_2$O: C=44.05%, H=4.18%, N=8.93%; found: C=44.13%, H=3.55%, N=8.61%.

EXAMPLE 9

3-[3-(S)-(5-Cholorobenzo[b]thiophene-2-sulfonyl)-methylamino)-2-oxo-pyrrolidin-1-ylmethyl]-benzamidine trifluoroacetate A. 1-Chloro-4-(2,2-dimethoxy-ethyl-sulfanyl)-benzene.

The title compound is prepared as described in EXAMPLE 5, Part A substituting 4-chlorothiophenol for 3-chlorothiophenol. The crude product is purified by column chromatography eluting with a gradient of 4% Et$_2$O/hexanes to 10% Et$_2$O/hexanes to afford the title compound as an oil.

$^1$H NMR (CDCl$_3$, 300 MHz) δ 7.28 (m, 2H), 7.20 (m, 2H), 4.50 (t, 1H), 3.06 (s, 3H), 3.03 (s, 3H), EI MS, [M]$^+$=232, 234, Cl pattern.

B. 5-Chlorobenzo[b]thiophene.

The title compound is prepared as described in EXAMPLE 5, Part B substituting 1-chloro-4-(2,2- dimethoxy-ethyl-sulfanyl)-benzene for 1-chloro-3-(2,2-dimethoxy-ethyl-sulfanyl)benzene. The crude product is purified by column chromatography eluting with hexanes to afford the title compound as a white solid.

$^1$H NMR (CDCl$_3$, 300 MHz) δ 7.78 (m, 2H), 7.50 (d, 1H), 7.28 (m, 2H), EI MS, [M]$^+$=168, 170, Cl pattern.

C. 5-Chlorobenzo[b]thiophene-2-sulfonyl chloride.

The title compound is prepared as described in EXAMPLE 1, Part D substituting 5-chlorobenzo[b]thiophene for thianaphthalene. The crude product is purified by column chromatography eluting with hexanes to yield the title compound as white solid.

$^1$H NMR (CDCl$_3$, 300 MHz) δ 8.05 (s, 1H), 7.98 (s, 1H), 782 (d, 1H), 7.53 (d, 2H).

D. 5-Chlorobenzo[b]thiophene-2-sulfonic acid [1-(3-cyano-benzyl)-2-oxo-pyrrolidin-3-yl]-amide.

The title compound is prepared as described in EXAMPLE 1, Part E substituting 5-chlorobenzo[b]thiophene-2-sulfonyl chloride for benzo[b]thiophene-2-sulfonyl chloride. The crude product is purified by column chromatography eluting with gradient of 10% EtOAc/CH$_2$Cl$_2$ to 20% EtOAc/CH$_2$Cl$_2$ to give the product as white solid.

$^1$H NMR (DMSO-d$_6$, 300 MHz)δ 8.70 (d, 1H), 8.08 (m, 2H), 7.98 (s, 1H), 7.70 (m, 1H), 7.60 (m, 5H), 7.51 (m, 5H), 4.36 (AB, 2H), 4.24 (m, 1H), 3.08 (m, 2H), 2.12 (m, 1H), 1.61 (m, 1H). FAB MS, [M+H]$^+$=446, 448, Cl pattern.

E. 3-[3-(S)-(5-Chlorobenzo[b]thiophene-2-sulfonylamino)-2-oxo-pyrrolidin-1-ylmethyl]-benzamidine trifluoroacetate.

The title compound is prepared as described in EXAMPLE 1, Part F using 5-chlorobenzo[b]thiophene-2-sulfonic acid [1-(3-cyano-benzyl)-2-oxo-pyrrolidin-3-(S)-yl]-methylamide as the starting material. The crude product is purified by RP-HPLC eluting with a gradient of 10% CH$_3$CN/H$_2$O (0.1% TFA) to 80% CH$_3$CN/H$_2$O (0.1% TFA). The appropriate fractions are lyophilized to provide the title compound as a white solid.

$^1$H NMR (DMSO-d$_6$, 300 MHz)δ 9.28 (bs, 2H), 8.69 (d, 1H), 8.10 (m, 2H), 7.99 (s, 1H), 7.68 (m, 1H), 7.48 (m, 4H), 4.40 (AB, 2H), 4.21 (m, 1H), 3.10 (m, 2H), 2.13 (m, 1H), 1.68 (m, 1H), FAB MS, [M+H]$^+$=463, 465, Cl pattern. Elemental analysis calculated with 2.0 mole of H$_2$O C=43.10%, H=3.95%, N=9.14%; found: C=43.33%, H=3.45%, N=8.90%.

EXAMPLE 10

3-[3-(S)-(5-Cholorobenzo[b]thiophene-2-sulfonylamino)-2-oxo-pyrrolidin-1-ylmethyl]-benzamidine trifluoroacetate A. 5-Chlorobenzo[b]thiophene-2-sulfonic acid [1-(3-cyano-benzyl)-2-oxo-pyrrolidin-3-(S)- yl]-methylamide.

The title compound is prepared as described in EXAMPLE 2, Part A substituting 5-chlorobenzo[b] thiophene-2-sulfonic acid [1-(3-cyano-benzyl)-2-oxo-pyrrolidin-3-(S)-yl]-amide for benzo[b]thiophene-2-sulfonic acid [1-(3-cyano-benzyl)-2-oxo-pyrrolidin-3-yl]-amide. The crude product is triturated with Et$_2$O to give the product as a white solid.

$^1$H NMR (DMSO-d$_6$, 300 MHz)δ 8.12 (s, 1H), 8.04 (m, 1H), 7.72 (m, 1H), 7.64 (s, 1H), 7.50 (m, 4H), 4.91 (m, 1H), 4.37 (AB, 2H), 3.14 (m, 2H), 2.76 (s, 3H), 2.06 (m, 1H), 1.88 (m, 1H). FAB MS, [M+H]$^+$=460, 462, Cl pattern.

B. 3-[3-(S)-(5-Cholorobenzo[b]thiophene-2-sulfonyl)-methyl-amino]-2-oxo-pyrrolidin-1-ylmethyl]-benzamidine trifluoroacetate.

The title compound is prepared as described in EXAMPLE 1, Part F using 5-chlorobenzo[b]thiophene-2-sulfonic acid [1-(3-cyano-benzyl)-2-oxo-pyrrolidin-3-(S)-yl]-methylamide as the starting material. The crude product is purified by RP-HPLC eluting with a gradient of 10% CH$_3$CN/H$_2$O (0.1% TFA) to 70% CH$_3$CN/H$_2$O (0.1% TFA). The appropriate fractions are lyophilized to provide the title compound as a white solid.

$^1$H NMR (DMSO-d$_6$, 300 MHz)δ 9.26 (bs, 2H), 8.95 (bs, 2H), 8.05 (m, 3H), 7.62 (m, 1H), 7.48 (m, 4H), 4.90 (t, 1H), 4.39 (AB, 2H), 3.14 (m, 2H), 2.77 (s, 3H), 2.08 (m, 1H), 1.89 (m, 1H). FAB MS, [M+H]$^+$=477, 479, Cl pattern. Elemental analysis calculated with 1.25 mole of H$_2$O; C=45.10%, H=4.03%, N=9.15%; found: C=44.97%, H=3.94%, N=8.91%.

EXAMPLE 11

3-[3-(S)-(4-Methylbenzo[b]thiophene-2-sulfonylamino]-2-oxo-pyrrolidin-1-ylmethyl]-benzamidine trifluoroacetate A. 3-Methyl-1-(2,2-dimethoxy-ethyl-sulfanyl)-benzene.

The title compound is prepared as described in EXAMPLE 5, Part A substituting 3-methylthiophenol for 3chlorothiophenol. The crude product is purified by column chromatography eluting with a gradient of hexanes to 10% Et$_2$O/hexanes to afford the title compound as an oil.

$^1$H NMR (CDCl$_3$, 300 MHz) δ 7.20 (m, 3H), 7.02 (m, 1H), 4.50 (m, 1H), 3.07 (s, 3H), 3.02 (s, 3H), 2.32 (s, 3H). EI MS, [M]$^+$=212.

B. 4-Methylbenzo[b]thiophene and 6-Methylbenzo[b] thiophene.

The title compound is prepared as described in EXAMPLE 5, Part B substituting 3-methyl-1-(2,2-dimethoxy-ethyl-sulfanyl)benzene for 1-chloro-3-(2,2-dimethoxy-ethyl-sulfanyl)-benzene. The crude product is purified by column chromatography eluting with hexanes to afford the title compounds as an inseparable (2:1) mixture as an oil. EI MS, [M]$^+$=148.

C. 4-Methylbenzo[b]thiophene-2-sulfonyl chloride and 6-Methylbenzo[b]thiophene-2-sulfonyl chloride.

The title compound is prepared as described in EXAMPLE 1, Part D substituting 4-methylbenzo[b]thiophene and 6-methylbenzo[b]-thiophene mixture for thianaphthalene. The crude product is purified by column chromatography eluting with hexanes to yield 4-methylbenzo[b]thiophene-2-sulfonyl chloride as well as 6-methylbenzo[b]thiophene-2-sulfonyl chloride as white solids.

4-Methylbenzo[b]thiophene-2-sulfonyl chloride
$^1$H NMR (CDCl$_3$, 300 MHz) δ 8.22 (s, 1H), 7.78 (d, 1H), 7.49 (t, 2H), 7.32 (d, 1H, 2.65 (s, 3H).

6-Methylbenzo[b]thiophene-2-sulfonyl chloride
$^1$H NMR (CDCl$_3$, 300 MHz) δ 8.09 (s, 1H), 7.83 (d, 2H), 7.70 (s, 1H), 7.35 (d, 1H, 2.50 (s, 3H).

D. 4-Methylbenzo[b]thiophene-2-sulfonic acid [1-(3-cyano-benzyl)-2-oxo-pyrrolidin-3-(S)-yl]-amide The title compound is prepared as described in EXAMPLE 1, Part E, substituting 4-methylbenzo[b] thiophene-2-sulfonyl chloride for benzo[b]thiophene-2-sulfonyl chloride. The crude product is triturated with Et$_2$O to give the product as a white solid.

¹H NMR (CDCl₃, 300 MHz) δ 8.02 (s, 1H), 7.68 (d, 1H), 7.57 (m, 1H), 7.42 (m, 4H), 7.23 (m, 1H), 5.49 (bs, 1H), 4.46 (AB, 2H), 3.90 (m, 1H), 3.23 (m, 2H), 2.68 (m, 1H), 2.62 (s, 3H), 2.16 (m, 1H).

E. 3-[3-(S)-(4-Methylbenzo[b]thiophene-2-sulfonylamino)-2-oxo-pyrrolidin-1-ylmethyl]-benzamidine trifluroacetate The title compound is prepared as described in EXAMPLE 1, Part F using 4-methylbenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz) δ 9.26 (bs, 2H), 9.00 (bs, 2H), 8.58 (m, 1H), 7.97 (m, 2H), 7.79 (s, 1H), 7.60 (m, 1H), 7.49 (m, 3H), 7.31 (m, 1H), 4.40 (AB, 2H), 4.22 (m, 1H), 3.12 (m, 2H) 2.40 (s, 3H), 2.10 (m, 1H), 1.66 (m, 1H). FAB MS, [M+H]⁺=443. Elemental analysis calculated with 2.0 mole of H₂O; C=46.61%, H=4.59%, N=9.45%; found: C=46.75%, H=4.14%, N=9.38%.

EXAMPLE 12

3-[3-(S)-(6-Methylbenzo[b]thiophene-2-sulfonylamino)-2-oxo-pyrrolidin-1-ylmethyl]-benzamidine trifluroacetate

A. 6-Methylbenzo[b]thiophene-2-sulfonic acid [1-(3-cyano-benzyl)-2-oxo-pyrrolidin-3-(S)-yl]-amide The title compound is prepared as described in EXAMPLE 1, Part E, substituting 6-methylbenzo[b]thiophene-2-sulfonyl chloride, prepared as described in EXAMPLE 11, Part C, for benzo[b]thiophene-2-sulfonyl chloride. The crude product is purified by column chromatography eluting with a gradient of 10% EtOAc/CH₂Cl₂ to 15% EtOAc/CH₂Cl₂ to afford the title compound as a white solid.

¹H NMR (CDCl₃, 300 MHz) δ 7.89 (s, 1H), 7.79 (d, 1H), 7.67 (s, 1H), 7.58 (m, 1H), 7.43 (m, 3H), 7.30 (m, 1H), 5.50 (bs, 1H), 4.2 (AB, 2H), 3.88 (m, 1H), 3.21 (m, 2H), 2.64 (m, 1H), 2.49 (s, 3H), 2.12 (m, 1H).

B. 3-[3-(S)-(6-Methylbenzo[b]thiophene-2-sulfonylamino)-2-oxo-pyrrolidin-1-ylmethyl]-benzamidine trifluroacetate The title compound is prepared as described in EXAMPLE 1, Part F using 5-methylbenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz) δ 9.23 (bs, 2H), 9.00 (bs, 2H), 8.56 (d, 1H, 7.96 (s, 1H), 7.84 (m, 2H), 7.67 (m, 1H), 7.53 (m, 3H), 7.28 (d, 1H), 4.42 (AB, 2H), 4.19 (m, 1H, 3.12 (m, 2H), 2.40 (s, 3H), 2.12 (m, 1H), 1.64 (m, 1H), FAB MS, [M+H]⁺=443. Elemental analysis calculated with 0.50 mole of H₂O: C=48.84%, H=4.28%, N=9.91%; found: C=48.89%, H=4.05%, N=9.73%.

EXAMPLE 13

3-[3-(S)-(5-Methylbenzo[b]thiophene-2-sulfonylamino)-2-oxo-pyrrolidin-1-ylmethyl]-benzamidine trifluroacetate

A. 4-Methyl-1-(2,2-dimethoxy-ethyl-sulfanyl)-benzene

The title compound is prepared as described in EXAMPLE 5, Part A substituting 4-methylthiophenol for 3-chlorothiophenol. The crude product is purified by column chromatography eluting with hexanes to afford the title compound as an oil.

¹H NMR (CDCl₃, 300 MHz) δ 7.28 (m, 2H), 7.10 (m, 2H), 4.49 (t, 1H, 3.06 (s, 3H), 3.03 (s, 3H), 2.28 (s, 3H).

B. 5-Methylbenzo[b]thiophene

The title compound is prepared as described in EXAMPLE 5, Part B substituting 4-methyl-1-(2,2-dimethoxy-ethyl-sulfanyl)-benzene for 1-chloro-3-(2,2-dimethoxy-ethyl-sulfanyl)-benzene. The crude product is purified by column chromatography eluting with hexanes to afford the title compound as a white solid.

¹H NMR (CDCl₃, 300 MHz) δ 7.78 (d, 1H), 7.62 (s, 1H), 7.39 (d, 1H), 7.23 (d, 1H), 7.17 (d, 1H), 2.50 (s, 3H).

C. 5-Methylbenzo[b]thiophene-2-sulfonyl chloride

The title compound is prepared as described in EXAMPLE 1, Part D substituting 5-chlorobenzo[b]thiophene for thianaphthalene. The crude product is purified by column chromatography eluting with hexanes to yield the title compound as a white solid.

¹H NMR (CDCl₃, 300 MHz) δ 8.08 (s, 1H), 7.78 (m, 2H), 7.39 (d, 1H), 2.51 (s, 3H).

D. 5-Methylbenzo[b]thiophene-2-sulfonic acid [1-(3-cyano-benzyl)-2-oxo-pyrrolidin-3-(S)-yl]-amide The title compound is prepared as described in EXAMPLE 1, Part E, substituting 5-methylbenzo[b]thiophene-2sulfonyl chloride for benzo[b]thiophene-2-sulfonyl chloride. The crude product is triturated with Et₂O to give the product as a white solid.

¹H NMR (CDCl₃, 300 MHz) δ 7.86 (s, 1H), 7.73 (m, 2H), 7.69 (s, 1H), 7.60 m, 1H), 7.42 (m, 2H), 7.30 (s, 1H), 5.52 (bs, 1H), 4.43 (AB, 2H), 3.91 (m, 1H), 3.20 (m, 2H, 2.64 (m, 1H), 2.48 (s, 3H), 1.61 (m, 1H).

E. 3-[3-(S)-(5-Methylbenzo[b]thiophene-2-sulfonylamino)-2-oxo-pyrrolidin-1-ylmethyl]-benzamidine trifluoroacetate The title compound is prepared as described in EXAMPLE 1, Part F using 5-methylbenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz) δ 9.26 (bs, 2H), 9.00 (bs, 2H), 8.58 (m, 1H), 7.97 (m, 2H), 7.79 (s, 1H), 7.60 (m, 1H), 7.49 (m, 3H, 7.31 (m, 1H), 4.40 (AB, 2H), 4.22 (m, 1H), 3.12 (m, 2H, 2.40 (s, 3H), 2.10 (m, 1H), 1.66 (m, 1H), FAB MS, [M+H]⁺=443. Elemental analysis calculated with 0.75 mole of H₂O c=48.46%, H=4.33%, N=9.83%; found: C=48.41%, H=3.98%, N=9.43%.

EXAMPLE 14

3-[3-(4,6-Dichlorobenzo[b]thiophene-2-sulfonylamino)-2-oxo-pyrrolidin-1-ylmethyl]-benzamidine trifluroacetate

A. 1,3-Dichloro-5-(2,2-dimethoxy-ethyl-sulfanyl)-benzene

The title compound is prepared as described in EXAMPLE 5, Part A substituting 3,5-dichlorothiophenol for 3-chlorothiophenol. The crude product is purified by column chromatography eluting with hexanes to afford the title compound as an oil.

$^1$H NMR (CDCl$_3$, 300 MHz) δ 7.19 (s, 2H), 7.12 (s, 1H), 4.51 (m, 1H), 3.13 (s, 3H), 3.09 (s, 3H).

B. 4,6-Dichlorobenzo[b]thiophene

The title compound is prepared as described in EXAMPLE 5, Part B substituting 1,3-dichloro-5-(2,2-dimethoxy-ethyl-sulfanyl)-benzene for 1-chloro-3-(2,2-dimethoxy-ethyl-sulfanyl)-benzene. The crude product is purified by column chromatography eluting with hexanes to afford the title compound as a white solid.

EI MS, [M]$^+$=202.

C. 4,6-Dichlorobenzo[b]thiophene-2-sulfonyl chloride

The title compound is prepared as described in EXAMPLE 1, Part D substituting the 4,6-dichlorobenzo[b]thiophene for thianaphthalene. The crude product is purified by column chromatography eluting with hexanes to yield the title compound as a white solid.

$^1$H NMR (CDCl$_3$, 300 MHz) δ 8.27 (s, 1H), 7.79 (s, 1H), 7.24 (s, 1H).

D. 4,6-Dichlorobenzo[b]thiophene-2-sulfonic acid [1-(3-cyano-benzyl)-2-oxo-pyrrolidin-3-(S)-yl]-amide The title compound is prepared as described in EXAMPLE 1, Part E, substituting 4,6-dichlorobenzo[b]thiophene-2-sulfonyl chloride for benzo[b]thiophene-2-sulfonyl chloride. The crude product is triturated with Et$_2$O to give the product as a white solid.

$^1$H NMR (CDCl$_3$, 300 MHz) δ 8.01 (s, 1H), 7.70 (s, 1H), 7.58 (m, 1H), 7.42 (m, 4H), 5.66 (bs, 1H), 4.41 (AB, 2H), 3.95 (m, 1H), 3.22 (m, 2H), 2.62 (m, 1H), 2.12 (m, 1H).

E. 3-[3-(S)-(4,6-Dichlorobenzo[b]thiophene-2-sulfonylamino)-2-oxo-pyrrolidin-1-ylmethyl]-benzamidine trifluroacetate The title compound is prepared as described in EXAMPLE 1, Part F using 4,6-dichlorobenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% CH$_3$CN/H$_2$O (0.1% TFA) to 80% CH$_3$CN/H$_2$O (0.1% TFA). The appropriate fractions are lyophilized to provide the title compound as a white solid.

$^1$NMR (DMSO-d$_6$, 300 MHz) δ 9.27 (bs, 2H), 9.18 (bs, 2H), 8.82 (m, 1H), 8.24 (d, 1H), 7.98 (d, 1H), 7.72 (m, 1H), 7.63 (m, 1H), 7.52 (m, 3H, 4.39 (AB, 2H), 4.28 (m, 1H), 3.12 (m, 2H), 2.13 (m, 1H), 1.68 (m, 1H). FAB MS, [M+H]$^+$=497, 499, Cl pattern. Elemental analysis calculated with 1.33 mole of H$_2$O: C=43.22%, H=3.44%, N=8.82%; found: C=43.10%, H=3.18%, N=8.47%.

EXAMPLE 15

([3-[3-(s)-(4,6-Dichlorobenzo[b]thiophene-2-sulfonylamino)-2-oxo-pyrrolidin-1-ylmethyl]-phenyl]-iminomethyl)-carbamic acid 2,2,2-trichloroethyl ester

A. ([3-[3-(S)-4,6-Dichlorbenzo[b]thiophene-2-sulfonylamino)-2-oxo-pyrrolidin-1-ylmethyl]-phenyl]-iminomethyl)-carbamic acid 2,2,2-trichloroethyl ester To a solution of 3-[3-(S)-(4,6-dichlorobenzo[b]thiophene-2-sulfonylamino)-2-oxo-pyrrolidin-1-ylmethyl]-benzamidine trifluroacetate (0.25 g, 0.40 mmol), prepared as in EXAMPLE 14, Part E, in 4 mL of CH$_2$Cl$_2$:DMF (10:1) is added N-methyl piperidine (0.12 g, 1.2 mmol) followed by trichloroethyl chloroformate (0.93 g, 0.44 mmol). The solution is stirred for 16 hours. After this time, the solution is diluted with EtOAc. The organic layer is washed with 1N HCl, H$_2$O, saturated NaCl. The organic layer is dried over MgSO$_4$, filtered and concentrated. The residue is purified by column chromatography eluting with a gradient of 1% MeOH/CH$_2$Cl$_2$ to 3% MeOH/CH$_2$Cl$_2$ to afford the title compound (0.20 g, 0.30 mmol) as a white solid.

$^1$H NMR (DMSO-d$_6$, 300 MHz) δ 9.23 (bs, 2H), 8.82 (d, 1H), 8.28 (s, 1H), 8.00 (s, 1H), 7.84 (d, 1H), 7.76 (s, 1H), 7.72 (s, 1H), 7.40 (m, 2H), 4.83 (s, 2H), 4.38 (AB, 2H), 4.27 (m, 1H), 3.09 (m, 2H), 2.13 (m, 1H), 1.65 (m, 1H). FAB MS, [M+H]$^+$=671, 673, 675, 5-Cl pattern.

EXAMPLE 16

4-Amino-3-[3-(S)-4,6-dichlorobenzo[b]thiophene-2-sulfonylamino)-2-oxo-pyrrolidin-1-ylmethyl]-benzamidine trifluroacetate

A. 4-Amino-3-methyl benzonitrile

To a solution of 3-methyl-4-nitrobenzonitrile (2.0 g, 12.3 mmol) in 100 mL of EtOH is added SnCl$_2$ (13.9 g, 61.7 mmol). The resulting solution is heated at reflux. After 2 hours, the solution is cooled to ambient temperatures. The solution is poured into 150 mL of ice water. The pH of the solution is adjusted to >7 with a solution of saturated NaHCO$_3$. The solution is diluted with EtOAc and the resulting mixture is filtered through Celite. The filtered solution is separated. The organic layer is dried over MgSO$_4$, filtered and concentrated to give the title compound (1.57 g, 8.7 mmol) as an off-white solid.

$^1$H NMR (CDCl$_3$, 300 MHz) δ 7.30 (m, 2H), 6.63 (d, 1H), 4.10 (bs, 2H), 2.15 (m, 2H). EI MS, [M]$^+$=132.

B. 4-Benzhydrylidene-amino)-3-methyl-benzontrile

To a solution of 4-amino-3-methyl benzonitrile (1.20 g, 9.08 mmol) in 75 mL of toluene is added benzophenone (1.74 g, 9.53 mmol) and p-toluenesulfonic acid (0.43 g, 2.1 mmol). The reaction vessel is fitted with a Dean-Stark trap and the solution is heated at reflux. After 24 hours, the solution is cooled to ambient temperatures. The solution is concentrated. The crude material is purified by column chromatography eluting with a gradient of 3% EtOAc/hexanes to 10% EtOAc/hexanes. The title compound (2.43 g, 8.2 mmol) is obtained as an oil.

$^1$H NMR (CDCl$_3$, 300 MHz) δ 7.80 (m, 2H), 7.40 (m, 6H), 7.30 (s, 1H), 7.15 (d, 1H), 7.05 (bs, 2H), 6.05 (d, 1H), 2.20 (s, 3H). EI MS, [M]$^+$=296.

C. 4-Benzhydrylidene-amino)-3-bromoethyl-benzonitrile

To a solution of 4-(benzhydrylidene-amino)-3-methyl-benzonitrile (1.36 g, 4.27 mmol) in 40 mL of CCl$_4$ is added N-bromosuccinimide (0.84 g, 4.7 mmol) and benzoyl peroxide (0.22 g, 0.64 mmol). The solution is heated to reflux for 16 hours. The solution is cooled to ambient temperatures. The solution is diluted with CH$_2$Cl$_2$. The solution is washed with 1N NaOH and saturated NaCl. The organic layer is dried over MgSO$_4$, filtered and concentrated. The crude material is purified by column chromatography eluting with a gradient of 5% EtOAc/hexanes to 10% EtOAc/hexanes. The title compound (0.91 g, 2.43 mmol) is obtained as an oil.

D. {1-[2-Benzhydrylidene-amino)-5-cyano-benzyl]-2-oxo-pyrrolidin-3-(S)-yl}-carbamic acid tert-butyl ester The title compound is prepared as described in EXAMPLE 1, Part B substituting 4-(benzhydrylidene-amino)-3-bromomethyl-benzonitrile for α-bromo-m-toluyl nitrile. The crude material is purified by column chromatography eluting with a gradient of 30% EtOAc/hexanes to 40% EtOAc/hexanes. The title compound is obtained as a yellow solid.

$^1$H NMR (CDCl$_3$, 300 MHz) δ 7.70 (bs, 2H), 7.40 (s, 1H), 7.38 (bs, 6H), 7.30 (d, 1H), 7.15 (bs, 2H), 6.48 (d, 1H), 5.00 (d, 1H, 4.45 (AB, 2H), 4.15 (m, 1H, 3.30 (m, 2H), 2.61 (m, 1H), 1.90 (m, 1H), 1.45 (s, 9H).

E. 4-Amino-[3-(3-(S)-amino-2-oxo-pyrrolidin-1-ylmethyl)]-benzonitrile dihydrochloride The title compound is prepared as described in EXAMPLE 1, Part C. The title compound is obtained as white solid.

$^1$H NMR (CDCl$_3$, 300 MHz) δ 8.68 (bs, 3H), 7.38 (s, 1H), 6.76 (d, 1H), 5.68 (bs, 3H, 4.25 (AB, 2H), 4.07 (m, 1H), 3.29 (m, 2H), 2.38 (m, 1H, 1.98 (m, 1H).

F. 4,6-Dichlorobenzo[b]thiophene-2-sulfonic acid [1-(2-amino-5-cyano-benzyl)-2-oxo-pyrrolidin-3-(S)-yl]-amide The title compound is prepared as described in EXAMPLE 1, Part E, substituting 4,6-dichlorobenzo[b]thiophene-2-sulfonyl chloride for benzo[b]thiophene-2-sulfonyl chloride and substituting 4-amino-[3-(3-(S)-amino-2-oxo-pyrrolidin-1-ylmethyl)]-benzonitrile dihydrochloride for 3-(3-(S)-amino-2-oxo-pyrrolidin-1-ylmethyl)-benzonitrile hydrochloride. The crude product is triturated with Et$_2$O to give the product as a white solid.

$^1$H NMR (CDCl$_3$+CD$_3$OD, 300 MHz) δ 7.97 (s, 1H), 7.68 (s, 1H), 7.40 (s, 1H), 7.27 (d, 1H), 7.21 (d, 1H), 6.55 (bs, 1H), 4.20 (AB, 2H), 4.00 (t, 1H), 3.14 (m, 2H), 2.45 (m, 1H), 1.90 (m, 1H).

G. 4-Amino-3-[3-(S)-(4,6-dichlorobenzo[b]thiophene-2-sulfonylamino)-2-oxo-pyrrolidin-1-ylmethyl]-benzamidine trifluoroacetate The title compound is prepared as described in EXAMPLE 1, Part F using 4,6-dichlorobenzo[b]thiophene-2-sulfonic acid [1-(3-cyano-benzyl)-2-oxo-pyrrolidin-3-yl]-amide as the starting material. The crude product is purified by RP-HPLC eluting with a gradient of 10% CH$_3$CN/H$_2$O (0.1% TFA) to 80% CH$_3$CN/H$_2$O (0.1% TFA). The appropriate fractions are lyophilized to provide the title compound as a white solid.

$^1$H NMR (DMSO-d$_6$, 300 MHz) δ 9.27 (bs, 2H), 9.18 (bs, 2H), 8.82 (m, 1H), 8.24 (d, 1H), 7.98 (d, 1H), 7.72 (m, 1H), 7.63 (m, 1H), 7.52 (m, 3H), 4.39 (AB, 2H), 4.28 (M, 1H), 3.12 (m, 2H), 2.13 (m, 1H), 1.68 (m, 1H). FAB MS, [M+H]$^+$=497, 499, Cl pattern. Elemental analysis calculated with 1.33 mole of H$_2$O: C=43.22%, H=3.44%, N=8.82%; found: C=43.10%, H=3.18%, N=8.47%.

EXAMPLE 17

4-Hydroxy-3-[3-(S)-(4,6-dichlorobenzo[b]thiophene-2-sulfonylamino)-2-oxo-pyrrolidin-1-ylmethyl]-benzamidine trifluoroacetate

A. 2-Hydroxy-5-iodo-benzaldehyde

To a solution of salicylaldehyde (10 g, 82 mmol) in 50 mL of CH$_2$Cl$_2$ is added 22 mL of a 1 M ICl solution in CH$_2$Cl$_2$. The solution is stirred for 14 hours. After this time, a saturated solution of sodium sulfite is added until the color is discharged. The solution is diluted with CH$_2$Cl$_2$. The layers are separated. The organic layer is washed with water. The organic layer is dried over MgSO$_4$, filtered and concentrated. The resulting crude material is recrystallized from cyclohexane to give the title compound (7.2 g, 32 mmol) as white solid.

$^1$H NMR (CDCl$_3$, 300 MHz) δ 10.91 (s, 1H), 9.82 (s, 1H), 7.84 (d, 1H), 7.75 (dd, 1H), 6.75 (d, 1H). EI MS, [M]$^+$=248.

B. 5-Iodo-2-(2-methoxy-ethoxymethoxy)-benzyl alcohol

To a solution of sodium hydride (1.2 g of a 60% mineral oil dispersion, 52 mmol) in 25 mL of THF at 0° C., is added 2-hydroxy-5-iodo-benzaldehyde (7.0 g, 28 mmol). To the resulting solution is added 2-methoxy-ethoxymethoxy chloride (3.4 mL, 30 mmol) and 4 mL of 1,3-dimethyl-3,4,5,6-tetrahydro-2(1H)-pyrimidinone. The solution is allowed to warm to ambient temperatures. After 45 minutes, the solution is cooled to −15° C. and 6 mL of a 2 M solution of sodium borohydride in THF is added. The solution is stirred for 10 minutes. After this time, 24 mL of a 2M HCl solution in water is added. The resulting solution is diluted with ether, washed with water and saturated NaCl. The organic layer is dried over MgSO$_4$, filtered and concentrated. The resulting crude material is purified by column chromatography eluting with 40% EtOAc/hexanes to give the title compound (7.6 g, 22.5 mmol) as a white solid.

$^1$H NMR (CDCl$_3$, 300 MHz) δ 7.64 (d, 1H), 7.52 (dd, 1H), 6.90 (d, 1H), 5.30 (s, 2H), 4.62 (d, 2H), 3.82 (m, 2H), 3.54 (m, 2H), 3.35 (s, 3H), 2.53 (t, 1H). EI MS, [M]$^+$=338.

C. 5-Iodo-2-(2-methoxy-ethoxymethoxy)-benzyl bromide

To a solution of 5-iodo-2-(2-methoxy-ethoxymethoxy)-benzyl alcohol (7.5 g, 22 mmol) in 60 mL of THF at 15° C. is added triphenylphosphine (6.35 g, 24 mmol) followed by N-bromosuccinimide (4.3 g, 24 mmol). The solution is stirred for 5 minutes. The solution is allowed to warm to ambient temperature. After 20 minutes, the solution is concentrated. The crude product is purified by column chromatography eluting with EtOAc:CH$_2$Cl$_2$:hexane (3:1:6).

$^1$H NMR (CDCl$_3$, 300 MHz) δ 7.60 (d, 1H), 7.50 (dd, 1H), 6.91 (s, 1H), 5.30 (s, 2H), 4.43 (dd, 1h), 3.84 (m, 2H), 3.53 (m, 2H), 3.35 (s, 3H), EI MS, [M]$^+$=400.

D. 3-(S)-(tert-Butoxy-carbonyl-amino)-1-(5-iodo-2-(2-methoxy-ethoxymethoxy)-benzyl)-pyrrolidin-2-one The title compound is prepared as described in EXAMPLE 1, Part B substituting 5-iodo-2-(2-methoxy-ethoxymethoxy)-benzyl bromide for α-bromo-m-toluoyl nitrile. The crude material is purified by column chromatography eluting with EtOAc:CH$_2$Cl$_2$:hexane (3:1:1).

$^1$H NMR (CDCl$_3$, 300 MHz) δ 7.53 (dd, 1H), 7.45 (d, 1H), 6.93 (d, 1H), 5.26 (s, 2H), 5.20 (bs, 1H), 4.50 (d, 1H), 4.45 (d, 1H), 4.19 (m, 1H), 3.80 (m, 2H), 3.53 (m, 2H), 3.37 (s, 3H), 3.22 (m, 2H), 2.62 (m, 1H), 1.84 (m, 1H), 1.46 (s, 9H). Ion spray MS, [M+H]$^+$=521.

E. 3-(S)-(tert-Butoxy-carbonyl-amino)-1-(5-cyano-2-(2-methoxy-ethoxymethoxy)-benzyl)-pyrrolidin-2-one The title compound is prepared as described in EXAMPLE 3, Part C, substituting 3-(S)-(tert-butoxycarbonyl-amino)-1-(5-iodo-2-(2-methoxy-ethoxymethoxy)-benzyl)-pyrrolidin-2-one for (5-iodo-thiophen-3-yl) methanol. The crude material is purified by column chromatography eluting with EtOAc:$CH_2Cl_2$:hexane (3:1:1).

$^1$H NMR ($CDCl_3$, 300 MHz) δ 7.54 (dd, 1H), 7.45 (d, 1H), 7.20 (d, 1H), 5.35 (s, 2H), 5.20 (bs, 1H), 4.50 (d, 1H), 1.45 (s, 9H), 4.45 (d, 1H), 4.15 (m, 1H), 3.77 (m, 2H), 3.51 (m, 2H), 3.35 (s, 3H), 3.24 (m, 2H), 2.60 (m, 1H), 1.90 (m, 1H. EI MS, [M]$^+$=420.

F. 3-(S)-[(3-Amino-2-oxo-pyrrolidin-1-yl)-methyl]-4-hydroxy-benzonitrile hydrochloride The title compound is prepared as described in Example 1, Part C, substituting 3-(S)-(tert-butoxy-carbonyl-amino)-1-(5-cyano-2-(2-methoxy-ethoxymethoxy)-benzyl)-pyrrolidin-2-one for [1-(3-cyanobenzyl)-2-oxo-pyrrolidin-3-(S)-yl]-carbamic acid tert-butyl ester. The title compound is obtained as a white solid.

$^1$H NMR (DMSO-$d_6$, 300 MHz) δ 8.50 (bs, 3H), 7.50 (dd, 1H), 7.40 (d, 1H), 7.00 (d, 1H), 4.26 (d, 2H), 4.00 (m, 1H), 3.25 (m, 2H), 2.30 (m, 1H), 1.90 (m, 1H). EI MS, [M]$^+$=231.

G. 4,6-Dichlorobenzo[b]thiophene-2-sulfonic acid [1-(2-hydroxy-5-cyano-benzyl)-2-oxo-pyrrolidin-3-yl]-amide To a solution of 3-[(3-amino-2-oxo-pyrrolidin-1-yl)-methyl]-4-hydroxy-benzonitrile hydrochloride (0.20 g, 0.75 mmol) in 3 mL of pyridine at 0° C. is added 4,6-dichlorobenzo[b]thiophene-2-sulfonyl chloride. The solution is allowed to warm to ambient temperatures and is stirred for 6 hours. After this time, the solution is concentrated. The residue is dissolved in $CH_2Cl_2$. The organic solution is washed with 1 N HCl and saturated NaCl. The crude product is triturated with $Et_2O$ to give the title compound (0.22 g, 0.44 mmol) as a white solid.

$^1$H NMR ($CDCl_3$+DMSO-$d_6$, 300 MHz) δ 7.97 (s, 1H), 7.73 (m, 1H, 7.67 (s, 1H), 7.57 (s, 1H), 7.45 (m, 2H), 6.86 (bs, 1H), 4.31 (AB, 2H), 4.04 (m, 1H), 3.24 (m, 2H), 2.40 (m, 1H), 1.94 (m, 1H).

H. 4-Hydroxy-3-[3-(S)-4,6-dichlorobenzo[b]thiophene-2-sulfonylamino)-2-oxo-pyrrolidin-1-ylmethyl]-benzamidine trifluroacetate The title compound is prepared as described in EXAMPLE 1, Part F using 4,6-dichlorobenzo[b]thiophene-2-sulfonic acid [1-(2-hydroxy-5-cyano-benzyl)-2-oxo-pyrrolidin-3-(S)-yl]-amide as the starting material. The crude product is purified by RP-HPLC eluting with a gradient of 10% $CH_3CN/H_2O$ (0.1% TFA) to 80% $CH_3CN/H_2O$ (0.1% TFA). The appropriate fractions are lyophilized to provide the title compound as a white solid.

$^1$H NMR (DMSO-$d_6$, 300 MHz) δ 10.80 (bs, 1H), 9.00 (bs, 2H), 8.82 (d, 1H), 8.62 (bs, 2H), 8.29 (s, 1H), 7.57 (m, 2H), 7.48 (m, 2H), 6.97 (d, 1H), 4.30 (AB, 2H), 4.26 (m, 1H, 3.22 (m, 2H), 2.23 (m, 1H), 1.74 (m, 1H). FAB MS, [M+H]$^+$=513, 515, $Cl_2$ pattern.

EXAMPLE 18

3-[3-(S)-(6-fluorobenzo[b]thiophene-2-sulfonylamino)-2-oxo-pyrrolidin-1-ylmethyl]-benzamidine trifluoroacetate

A. 1-Fluoro-3-(2,2-dimethyoxy-ethyl-sulfanyl)-benzene

The title compound is prepared as described in EXAMPLE 5, Part A substituting 3-fluorothiophenol for 3-chlorothiophenol. The crude product is purified by column chromatography eluting with a gradient of hexanes to 10% EtOAc/hexanes to afford the title compound as an oil.

$^1$H NMR ($CDCl_3$, 300 MHz) δ 7.21 (m, 1H), 7.09 (m, 2H), 6.82 (m, 2H), 4.51 (m, 1H), 3.09 (s, 31H), 3.07 (s, 3H).

B. 6-Fluorobenzo[b]thiophene

The title compound is prepared as described in EXAMPLE 5, Part B substituting 1-fluoro-3-(2,2-dimethoxy-ethyl-sulfanyl)-benzene for 1-chloro-3-(2,2-dimethoxy-ethyl-sulfanyl)-benzene. The crude product is purified by column chromatography eluting with hexanes to afford the title compound as a white solid. EI MS, [M]$^+$=152.

C. 6-Fluorobenzo[b]thiophene-2-sulfonyl chloride

The title compound is prepared as described in EXAMPLE 1, Part D substituting 6-fluorobenzo[b]thiophene for thianaphthalene. The crude product is purified by column chromatography eluting with hexanes to yield the title compound as a white solid.

$^1$H NMR ($CDCl_3$, 300 MHz) δ 8.08 (s, 1H), 7.94 (dd, 1H), 7.58 (dd, 1H), 7.23 (dt, 1H).

D. 6-Fluorobenzo[b]thiophene-2-sulfonic acid [1-(3-cyano-benzyl)-2-oxo-pyrrolidin-3-(S)-yl]-amide The title compound is prepared as described in EXAMPLE 17, Part G, substituting 3-[(3-(S)-amino-2-oxo-pyrrolidin-1-yl)-methyl]-benzonitrile for 3-[(3-(S)-amino-2-oxo-pyrrolidin-1-yl)-methyl]-4-hydroxy-benzonitrile and substituting 6-fluorobenzo[b]thiophene-2-sulfonyl chloride for 4,6-dichlorobenzo[b]thiophene-2-sulfonyl chloride. The crude product is triturated with $Et_2O$ to give the product as a white solid.

$^1$H NMR ($CDCl_3$, 300 MHz) δ 7.85 (s, 1H), 7.78 (m, 1H), 7.64 (m, 2H), 7.49 (m, 1H), 7.42 (m, 3H), 7.14 (dt, 1H), 4.42 (AB, 2H), 4.02 (t, 1H), 3.18 (m, 2H), 2.60 (m, 1H), 2.12 (m, 1H).

E. 3-[3-(S)-(6-Fluorobenzo[b]thiophene-2-sulfonylamino)-2-oxo-pyrrolidin-1-ylmethyl]-benzamidine trifluroacetate The title compound is prepared as described in EXAMPLE 1, Part F using 6-fluorobenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% $CH_3CN/H_2O$ (0.1% TFA) to 80% $CH_3CN/H_2O$ (0.1% TFA). The appropriate fractions are lyophilized to provide the title compound as a white solid.

$^1$H NMR (DMSO-$d_6$, 300 MHz) δ 9.25 (bs, 4H), 8.63 (d, 1H), 8.03 (s, 1H), 8.00 (m, 2H), 7.63 (m, 1H), 7.51 (m, 3H), 7.31 (dt, 1H), 4.38 (AB, 2H), 4.28 (m, 1H), 3.11 (m, 2H), 2.13 (m, 1H), 1.68 (m, 1H). FAB MS, [M+H]$^+$=447. Elemental analysis calculated with 1.0 mole of $H_2O$: C=45.67%, H=3.71%, N=9.68%; found: C=45.52%, H=3.95%, N=9.31%.

EXAMPLE 19

4-Amino-3-[3-(S)-(6-fluorobenzo[b]thiophene-2-sulfonylamino)-2-oxo-pyrrolidin-1-ylmethyl]-benzamidine trifluroacetate

A. 6-Fluorobenzo[b]thiophene-2-sulfonic acid [1-(2-amino-5-cyano-benzyl)-2-oxo-pyrrolidin-3-(S)-yl]-amide The title compound is prepared as described in EXAMPLE 17, Part G, substituting 3-[(3-(S)-amino-2-oxopyrrolidin-1-yl)-methyl]-4-amino-benzonitrile for 3-[(3-(S)-amino-2-oxo-pyrrolidin-1-yl)-methyl]-4-hydroxy-benzonitrile and substituting 6-fluorobenzo[b]thiophene-2-sulfonyl chloride for 4,6-dichlorobenzo[b]thiophene-2-sulfonyl chloride. The crude product is triturated with Et$_2$O to give the product as a white solid. FAB MS, [M+H]$^+$=445.

B. 4-Amino-3-[3-(S)-(6-fluorobenzo[b]thiophene-2-sulfonylamino)-2-oxo-pyrrolidin-1-ylmethyl]-benzamidine trifluoroacetate The title compound is prepared as described in EXAMPLE 1, Part F using 6-fluorobenzo[b]thiophene-2-sulfonic acid [1-(2-amino-5-cyano-benzyl)-2-oxo-pyrrolidin-3-(S)-yl]-amide as the starting material. The crude product is purified by RP-HPLC eluting with a gradient of 10% CH$_3$CN/H$_2$O (0.1% TFA) to 70% CH$_3$CN/H$_2$O (0.1% TFA). The appropriate fractions are lyophilized to provide the title compound as a white solid.

$^1$H NMR (DMSO-d$_6$, 300 MHz) δ 8.74 (bs, 2H), 8.68 (d, 1H), 8.40 (bs, 2H), 8.01 (m, 3H), 7.53 (d, 1H), 7.36 (m, 2H), 6.72 (d, 1H), 6.20 (bs, 2H), 4.28 (m, 1H), 4.26 (AB, 2H), 3.12 (m, 2H), 2.09 (m, 1H), 1.60 (m, 1H), FAB MS, [M+H]$^+$=462.

EXAMPLE 20

4-Hydroxy-3-[3-(S)-(6-fluorobenzo[b]thiophene-2-sulfonylamino)-2-oxo-pyrrolidin-1-ylmethyl]-benzamidine trifluroacetate A. 6-Fluorobenzo[b]thiophene-2-sulfonic acid [1-(2-hydroxy-5-cyano-benzyl)-2-oxo-pyrrolidin-3-(S)-yl]-amide The title compound is prepared as described in EXAMPLE 17, Part G, substituting 6-fluorobenzo[b]thiophene-2-sulfonyl chloride for 4,6-dichlorobenzo[b]thiophene-2-sulfonyl chloride. The crude product is triturated with Et$_2$O to give the product as a white solid.

$^1$H NMR (CDCl$_3$, 300 MHz) δ 7.85 (s, 1H), 7.82 (m, 1H), 7.63 (m, 2H), 7.47 (m, 2H), 7.22 (dt, 1H), 6.93 (d, 1H), 4.32 (AB, 2H), 4.20 (t, 1H), 3.32 (m, 2H), 2.60 (m, 2H), 2.09 (m, 1H).

B. 4-Hydroxy-3-[3-(S)-(6-fluorobenzo[b]thiophene-2-sulfonylamino)-2-oxo-pyrrolidin-1-ylmethyl]-benzamidine trifluroacetate The title compound is prepared as described in EXAMPLE 1, Part F using 6-fluorobenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% CH$_3$CN/H$_2$O (0.1% TFA) to give 70% CH$_3$CN/H$_2$O (0.1% TFA). The appropriate fractions are lyophilized to provide the title compound as a white solid.

$^1$H NMR (DMSO-d$_6$, 300 MHz) δ 10.87 (bs, 1H), 9.00 (bs, 2H), 8.68 (bs, 2H), 8.60 (d, 1H), 8.01 (s, 1H), 8.00 (m, 2H), 7.54 (d, 1H), 7.38 (m, 2H), 6.92 (m, 1H), 4.30 (AB, 2H), 4.21 (m, 1H), 3.15 (m, 2H), 2.18 (m, 1H), 1.67 (m, 1H). FAB MS, [M+H]$^+$=463.

EXAMPLE 21

4-Amino-3-[3-(S)-(4-chlorobenzo[b]thiophene-2-sulfonylamino)-2-oxo-pyrrolidin-1-ylmethyl]-benzamidine trifluroacetate A. 4-Chlorobenzo[b]thiophene-2-sulfonic acid [1-(2-amino-5-cyano-benzyl)-2-oxo-pyrrolidin-3-(S)-yl]-amide The title compound is prepared as described in EXAMPLE 17, Part G, substituting 3-[3-(S)-amino-2-oxo-pyrrolidin-1-yl)-methyl]-4-amino-benzonitrile for 3-[(3-(S)-amino-2-oxo-pyrrolidin-1-yl)-methyl]-4-hydroxy-benzonitrile and substituting 4-chlorobenzo[b]thiophene-2-sulfonyl chloride for 4,6-dichlorobenzo[b]thiophene-2-sulfonyl chloride. The crude product is triturated with Et$_2$O to give the product as a white solid. FAB MS, [M+H]$^+$=461, 463, Cl pattern.

B. 4-Amino-3-[3-(S)-(4-chlorobenzo[b]thiophene-2-sulfonylamino)-2-oxo-pyrrolidin-1-ylmethyl]-benzamidine trifluoroacetate The title compound is prepared as described in EXAMPLE 1, Part F using 4-chlorobenzo[b]thiophene-2-sulfonic acid [1-(2-amino-5-cyano-benzyl)-2-oxo-pyrrolidin-3-(S)-yl]-amide as the starting material. The crude product is purified by RP-HPLC eluting with a gradient of 10% CH$_3$CN/H$_2$O (0.1% TFA) to 70%, CH$_3$CN/H$_2$O (0.1% TFA). The appropriate fractions are lyophilized to provide the title compound as a white solid.

$^1$H NMR (DMSO-d$_6$, 300 MHz) δ 8.79 (d, 1H), 8.75 (bs, 2H, 8.36 (bs, 2H), 8.07 (d, 1H), 8.03 (s, 1H), 7.52 (d, 1H), 7.50 (m, 2H), 7.37 (m, 2H), 6.70 (d, 1H), 6.15 (bs, 2H), 4.27 (m, 1H), 4.13 (AB, 1H), 3.14 (m, 2H), 2.13 (m, 1H), 1.60 (m, 1H). FAB MS, [M+H]$^+$=478, 480, Cl pattern.

EXAMPLE 22

4-Hydroxy-3-[3-(S)-(4-chlorobenzo[b]thiophene-2-sulfamylamino)-2-oxo-pyrrolidin-1-ylmethyl]-benzamidine trifluroacetate A. 4-Chlorobenzo[b]thiophene-2-sulfonic acid [1-(2-hydroxy-5-cyano-benzyl)-2-oxo-pyrrolidin-3-(S)-yl]-amide The title compound is prepared as described in EXAMPLE 17, Part G, substituting 4-chlorobenzo[b]thiophene-2-sulfonyl chloride for 4,6-dichlorobenzo[b]thiophene-2-sulfonyl chloride. The crude product is triturated with Et$_2$O to give the product as a white solid. FAB MS, [M+H]$^+$=462, 464, Cl pattern.

B. 4-Hydroxy-3-[3-(S)-(4-chlorobenzo[b]thiophene-2-sulfonylamino)-2-oxo-pyrrolidin-1-ylmethyl]-benzamidine trifluoroacetate The title compound is prepared as described in EXAMPLE 1, Part F using 4-chlorobenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% CH$_3$CN/H$_2$O (0.1% TFA) to 70% CH$_2$CN/H$_2$O (0.1% TFA). The appropriate fractions are lyophilized to provide the title compound as a white solid.

$^1$H NMR (DMSO-d$_6$, 300 MHz) δ 10.87 (bs, 1H), 9.01 (bs, 2H), 8.74 (d, 2H), 8.60 (bs, 1H), 8.08 (d, 1H), 8.02 (s, 1H), 7.53 (m, 3H), 7.38 (m, 2H), 6.92 (d, 1H), 4.30 (AB, 2H), 4.27 (m, 1H), 3.21 (m, 2H), 2.20 (m, 1H), 1.72 (m, 1H). FAB MS, [M+H]$^+$=479, 481, Cl pattern.

EXAMPLE 23

3-[3-(S)-4-Chloro-thieno[3,2-c]pyridine-2-sulfonylamino)-2-oxo-pyrrolidin-1-ylmethyl]-benzamidine trifluroacetate A. 3-Thiophene-2-yl-acrylic acid To a solution of 2-thiophene carboxaldehyde (10 g, 89 mmol), in 300 mL of CH$_2$Cl$_2$ is added methyl (triphenylphosphorylidene)acetate. The solution is stirred for 48 hours. After this time, the solution is concentrated. The residue is dissolved in 1000 mL of $H_2O$:MeOH:THF (1:1:1). To the resulting solution is added lithium hydroxide (22.9 g, 547 mmol). The solution is stirred for 3 hours. After this time, the solution is concentrated to ⅓ its volume. The remaining solution is washed with EtOAc. The aqueous solution is acidified to pH=5 with 1N HCl. A white precipitate forms. The solid is collected by filtration and is then dried over $P_2O_5$ under vacuum.

$^1$H NMR (CDCl$_3$, 300 MHz) δ 7.90 (d, 1H), 7.42 (d, 1H), 7.27 9d, 1H), 7.08 (d, 1H, 6.22 (d, 1H).

B. 5H-Thienol[3,2-c]pyridin-4-one

To a solution of 3-thiophen-2-yl-acrylic acid (7.39 g, 47.9 mmol) in 200 mL of acetone is added triethylamine (4.9 g, 47.9 mmol). The resulting solution is cooled to 0° C. and ethyl chloroformate (5.7 g, 52.8 mmol) is added dropwise. After 2 hours, sodium azide (4.67 g, 71.9 mmol) in 25 mL of $H_2O$ is then added. The solution is stirred for 1.5 hours at 0° C. After this time, the solution is poured into 300 mL of $H_2O$. A white precipitate forms which is collected by filtration. The resulting solid is dried over $P_2O_5$ under vacuum. The solid is suspended in 20 mL of diphenyl ether. This solution is added dropwise to a solution of tributylamine (6.9 g, 37.4 mmol) in 200 ml of diphenyl ether at 190° C. After 2 hours, the solution is cooled to ambient temperatures. The solution is diluted with 1000 mL of hexanes and is cooled to 0° C. The resulting solid is collected by filtration and the solid is washed with hexanes. The title compound (3.6 g, 23.8 mmol) is obtained as a white solid.

$^1$H NMR (DMSO-d$_6$, 300 MHz) δ 6.71 (m, 2H), 6.42 (d, 1H), 6.13 (d, 1H).

C. 4-Chloro-thieno[3,2-c]pyridine

5H-Thieno[3,2-c]pyridin-4-one (1.0 g, 6.62 mmol) is dissolved in 30 mL of phosphorous oxy chloride. The solution is heated to 100° C. After 4 hours, the solution is concentrated. The residue is dissolved in $CH_2Cl_2$. The resulting solution is washed with water and saturated NaCl. The organic layer is dried over MgSO$_4$, filtered and concentrated. The crude product is purified by column chromatography eluting with a gradient of 40% $CH_2Cl_2$/hexanes to 60% $CH_2Cl_2$/hexanes. The title compound (1.0 g, 5.8 mmol) is obtained as a white solid.

$^1$H NMR (CDCl$_3$, 300 MHz) δ 8.24 (d, 1H), 7.76 (d, 1H), 7.66 (m, 2H). EI MS, [M]$^+$=169, 171, Cl pattern.

D. 4-Chloro-thieno[3,2-c]pyridine-2-sulfonyl chloride

The title compound is prepared as described in EXAMPLE 1, Part D substituting the 4-chloro-thieno[3,2-c]pyridine for thianaphthalene. The crude product is purified by column chromatography eluting with a gradient of 40% $CH_2Cl_2$/hexanes to 60% $CH_2Cl_2$/hexanes. The title compound is obtained as a white solid.

$^1$H NMR (CDCl$_3$, 300 MHz) δ 8.39 (d, 1H), 8.28 (s, 1H), 7.72 (d, 1H).

E. 4-Chloro-thieno[3,2-c]pyridine-2-sulfonic acid [1-(3-cyano-benzyl)-2-oxo-pyrrolidin-3yl]-amide The title compound is prepared as described in EXAMPLE 17, Part G, substituting 3-(3-(S)-amino-2-oxo-pyrrolidin-1-yl)-methyl-benzonitrile for 3-[(3-(S)-amino-2-oxo-pyrrolidin-1-yl)-methyl]-4-hydroxy-benzonitrile and substituting 4-chloro-thieno[3,2-c]pyridine-2-sulfonyl chloride for 4,6-dichlorobenzo[b]thiophene-2-sulfonyl chloride. The crude product is purified by column chromatography eluting with a gradient of 10% $CH_2Cl_2$/EtOAc to 20% $CH_2Cl_2$/EtOAc. The title compound is obtained as a white solid.

$^1$H NMR (CDCl$_3$, 300 MHz) δ 8.34 (m, 1H), 8.11 (s, 1H), 7.73 (m, 1H), 7.58 (m, 1H), 7.40 (m, 3H), 5.62 (bs, 1H), 4.46 (AB, 2H), 3.97 (m, 1H), 3.27 (m, 2H), 2.68 (m, 1H), 2.12 (m, 1H).

F. 3-[3-(S)-(4-Chloro-thieno[3,2-c]pyridine-2-sulfonylamino)-2-oxo-pyrrolidin-1-ylmethyl]-benzamidine trifluoroacetate The title compound is prepared as described in EXAMPLE 1, Part F using 4-chlorobenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% $CH_3CN/H_2O$ (0.1% TFA) to 70% $CH_3CN/H_2O$ (0.1% TFA). The appropriate fractions are lyophilized to provide the title compound as a white solid.

$^1$H NMR (DMSO-d$_6$, 300 MHz) δ 9.28 (bs, 2H), 9.18 (bs, 2H), 9.06 (d, 1H), 8.38 (d, 1H), 8.22 (d, 1H), 8.08 (s, 1H), 7.68 (m, 1H), 7.52 (m, 3H), 4.41 (AB, 2H), 4.33 (m, 1H), 3.14 (m, 2H), 2.21 (m, 1H), 1.72 (m, 1H). FAB MS, [M+H]$^+$=464, 466, Cl pattern.

EXAMPLE 24

4-Hydroxy-3-[3-(S)-(4-chloro-thieno[3,2-c]pyridine-2-sulfonylamino)-2-oxo-pyrrolidin-1-ylmethyl]-benzamidine trifluroacetate

A. 4-Chloro-thieno[3,2-c]pyridine-2-sulfonic acid [1-(2-hydroxy-5-cyano-benzyl)-2-oxo-pyrrolidin-3-(S)-yl]-amide The title compound is prepared as described in EXAMPLE 17, Part G, substituting 4-chloro-thieno[3,2-c]pyridine-2-sulfonyl chloride for 4,6-dichlorobenzo[b]thiophene-2-sulfonyl chloride. The crude product is purified by column chromatography eluting with a gradient of 1% MeOH/$CH_2Cl_2$ to 4% MeOH/$CH_2Cl_2$. The title compound is obtained as a white solid.

$^1$H NMR (CDCl$_3$, 300 MHz) δ 9.13 (s, 1H), 8.38 (d, 1H), 8.09 (s, 1H), 7.72 (d, 1H), 7.52 (d, 1H), 7.52 (dd, 1H), 7.38 (s, 1H), 6.96 (d, 1H), 5.44 (d, 1H), 4.32 (AB, 2H), 4.10 (m, 1H), 3.48 (m, 2H), 2.74 (m, 1H), 2.18 (m, 1H).

B. 4-Hydroxy-3-[3-(S)-(4-chloro-thieno[3,2-c]pyridine-2-sulfonylamino)-2-oxo-pyrrolidin-1-ylmethyl]-benzamidine trifluroacetate The title compound is prepared as described in EXAMPLE 1, Part F using 4-chlorobenzo[b]thiophene-2-sulfonic acid [1-(3-cyano-benzyl)-2-oxo-pyrrolidin-3-(S)-yl]-amide as the starting material. The crude product is purified by RP-HPLC eluting with a gradient of 10% $CH_3CN/H_2O$ (0.1% TFA) to 70% $CH_3CN/H_2O$ (0.1% TFA). The appropriate fractions are lyophilized to provide the title compound as a white solid.

$^1$H NMR (DMSO-d$_6$, 300 MHz) δ 10.91 (bs, 1H), 9.04 (bs, 2H), 8.93 (d, 1H), 8.78 (bs, 2H), 8.40 (d, 1H), 8.21 (d, 1H), 8.08 (s, 1H), 7.62 (m, 1H), 7.41 (s, 1H), 6.97 (d, 1H), 4.31 (AB, 2H), 4.30 (m, 1H), 3.22 (m, 2H), 2.26 (m, 1H), 1.78 (m, 1H). FAB MS, [M+H]$^+$=480, 482, Cl pattern.

EXAMPLE 25

3-[3-(S)-(5-Chlorothieno[3,2-b]pyridine-2-sulfonylamino)-2-oxo-pyrrolidin-1-ylmethyl]-benzamidine trifluoroacetate

A. 5-Chlorothieno[3,2-b]pyridine

The title compound is prepared from 3-acetyl thiophene according to the procedure described in *J. Chem. Soc., Perkin Trans. I*, 1981, 1531. The crude product is purified by column chromatography eluting with a gradient of 10% EtOAc/hexanes to 20% EtOAc/hexanes to afford a white solid.

$^1$H NMR (CDCl$_3$, 300 MHz) δ 8.12 (d, 1H), 7.80 (d, 1H), 7.51 (d, 1H), 7.28 (d, 1H), EI MS, [M]$^+$=169, 171, Cl pattern.

B. 5-Chlorothieno[3,2-b]pyridine-2-sulfonyl chloride

The title compound is prepared as described in EXAMPLE 1, Part D using 5-chlorothieno[3,2-b]pyridine in place of thianaphthalene. The crude product is obtained as a white solid and is of sufficient purity to be used in the subsequent step.

$^1$H NMR (CDCl$_3$, 300 MHz) δ 8.25 (s, 1H), 8.23 (d, 1H), 7.53 (d, 1H). EI MS, [M]$^+$=267, 269, Cl pattern.

C. 5-Chlorothieno[3,2-b]pyridine-2-sulfonic acid [1-(3-cyanobenzyl)-2-oxo-pyrrolidin-3-(S)-yl]-amide The title compound is prepared from 3-(3(S)-amino-2-oxo-pyrrolidin-1-ylmethyl)-benzonitrile hydrochloride as described in EXAMPLE 1, Part E using 5-chlorothieno[3,2-b]pyridine-2-sulfonyl chloride in place of benzo[b]thiophene-2-sulfonyl chloride. The product is obtained as a white solid.

$^1$H NMR (CDCl$_3$, 300 MHz) δ 8.18 (d, 1H), 8.03 (s, 1H), 7.59 (m, 1H), 7.47 (d, 1H), 7.45 (m, 2H), 7.42 (d, 1H), 5.95 (bs, 1H), 4.48 (s, 2H), 3.99 (m, 1H), 3.28 (m, 2H), 2.67 (m, 1H), 2.14 (m, 1H).

D. 3-[3-(S)-(5-Chlorothieno[3,2-b]pyridine-2-sulfonylamino)-2-oxo-pyrrolidin-1-ylmethyl]-benzamidine trifluoroacetate 5Chlorothieno[3,2-b]pyridine-2-sulfonic acid ([1-(3-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.1% TFA) to 70% CH$_3$CN/H$_2$O (0.1% TFA) and the appropriate product fractions are lyophilized to provide the title compound as a white solid.

$^1$H NMR (DMSO-d$_6$, 300 MHz) δ 9.30 (bs, 2H), 9.17 (bs, 2H), 8.93 (d, 1H), 8.67 (d, 1H), 8.11 (s, 1H), 7.69 (m, 1H, 7.64 (d, 1H), 7.55 (m, 3H), 4.43 (AB, 2H), 4.33 (m, 1H), 3.16 (m, 2H), 2.22 (m, 1H), 1.73 (m, 1H). FAB MS, [M+H]$^+$=464, 466, Cl pattern. Elemental analysis calculated with 1.0 mol H$_2$O: C=42.35%, H=3.55%, N=11.76%, found: C=42.34%, H=3.30%, N=11.39%.

EXAMPLE 26

3-[3-(S)-(Thieno[3,2-b]pyridine-2-sulfonylamino)-2-oxo-pyrrolidin-1-ylmethyl]-benzamidine bistrifluoroacetate To a solution of 3-[3-(S)-(5-chlorothieno[3,2-b]pyridine-2-sulfonylamino)-2-oxo-pyrrolidin-1-ylmethyl]-benzamidine trifluoroacetate (0.21 g, 0.36 mmol) in 10 mL of 1:1 benzene/MeOH is added excess solid KOH (0.25 g) and a catalytic amount of 10% palladium on activated carbon. The heterogeneous mixture is hydrogenated at room temperature on a Parr apparatus under 70 p.s.i. of H$_2$ for 5 days. The reaction mixture is filtered through a pad of Celite, washed with MeOH, and the filtrate is concentrated in vacuo. The crude product is purified by RP-HPLC eluting in a gradient of 10% CH$_3$CN/H$_2$O (0.1TFA) to 60% CH$_3$CN/H$_2$O (0.1% TFA) and the appropriate product fractions are lyophilized to provide the title compound (0.14 g, 0.21 mmol) as a white solid.

$^1$H NMR (DMSO-d$_6$, 500 MHz) δ 9.56 (bs, 2H), 9.35 (bs, 2H), 8.84 (d, 1H), 8.80 (d, 1H), 8.61 (d, 1H), 8.14 (s, 1H), 7.72 (dt, 1H), 7.61 (s, 1H), 7.57 (dd, 1H), 7.56 (s, 1H), 7.54 (dd, 1), 4.44 (AB, 2H), 4.34 (m, 1H), 3.17 (m, 2H), 2.21 (m, 1H), 1.74 (m, 1H). IS MS, [M+H]$^+$=430.

EXAMPLE 27

3-[3-(S)-(5-Chlorothieno[3,2-b]pyridine-2-sulfonylamino)-2-oxo-pyrrolidin-1-ylmethyl]-hydroxybenzamidine trifluroacetate 5-Chlorothieno[3,2-b]pyridine2-sulfonic acid [1-(3-cyanobenzyl)-2-oxo-pyrrolidin-3-(S)-yl]-amide (0.20 g, 0.45 mmol) is dissolved in 10 mL of MeOH. The solution is cooled to 0° C. and HCl gas is bubbled through the solution for 5 minutes. The reaction mixture is allowed to warm to room temperature and is stirred for 16 hours. At this time, the solution is concentrated in vacuo and pumped dry under high vacuum. To a solution of the residue dissolved in 20 mL of MeOH is added hydroxylamine hydrochloride (0.78 g, 11.2 mmol) followed by triethylamine (2.23 g, 22.0 mol). The resulting solution is heated at reflux for 2 hours. The solution is concentrated and the residue is purified by RP-HPLC eluting with a gradient of 10% CH$_3$CN/H$_2$O (0.1% TFA) to 70% CH$_3$CN/H$_2$O (0.1% TFA) and the appropriate fractions are lyophilized to give the title compound (0.17 g, 0.29 mmol) as a white solid.

$^1$H NMR (DMSO-d$_6$, 300 MHz) δ 8.94 (d, 1H), 8.78 (bs, 1H), 8.67 (d, 1H), 8.10 (s, 1H), 7.64 (d, 1H), 7.57 (m, 2H), 7.50 (m, 2H), 4.43 (AB, 2H), 4.33 m, 1H), 3.16 (m, 2H), 2.22 (m, 1H), 1.71 (m, 1H). FAB MS, [M+H]$^+$=480, 482, Cl pattern. Elemental analysis calculated with 1.6 mol H$_2$O, Cal. C=40.50%, H=3.59%, N=11.24% found: C=40.75%, H=3.20%, N=10.86%.

EXAMPLE 28

3-{3-(S)-[(5-Chlorothieno[3,2-b]pyridine-2-sulfonyl)-methylamino]-2-oxo-pyrrolidin-1-ylmethyl}-benzamidine trifluoroacetate

A. 5-Chlorothieno[3,2-b]pyridine-2-sulfonic acid [1-(3-cyanobenzyl)-2-oxo-pyrrolidin-3-(S)-yl]-methylamide 5-Chlorothienol[3,2-b]pyridine-2-sulfonic acid [1-(3-cyanobenzyl)-2-oxo-pyrrolidin-3-(S)-yl]-amide (0.25 g, 0.56 mmol) is dissolved in 6 mL of DMF and cooled to 0° C. To the solution is added methyl iodide (0.40 g, 2.82 mmol) and sodium hydride (25 mg of a 60% dispersion in mineral oil, 0.62 mmol). the reaction mixture is allowed to warm to room temperature and is stirred for 2 hours. At this time, the solution is diluted with H$_2$O and EtOAc and the layers are separated. The organic layer is washed with 1N HCl, H$_2$O, saturated NaHCO$_3$ solution and saturated NaCl.

The organic phase is then dried over MgSO$_4$, filtered and concentrated to give the title compound (0.25 g, 0.54 mmol) as a solid.

$^1$H NMR (CDCl$_3$, 300 MHz) δ 8.15 (d, 1H), 8.08 (s, 1H), 7.60 (m, 1H), 7.45 (m, 3H), 7.40 (d, 1H), 4.92 (m, 1H), 4.42 (AB, 2H), 3.24 (m, 2H), 2.92 (s, 3H), 2.43 (m, 1H), 2.06 (m, 1H).

B. 3-{3-(S)-[(5-Chlorothieno[3,2-b]pyridine-2-sulfonyl)-methylamino]-2-oxo-pyrrolidin-1-ylmethyl}-benzamidine trifluoroacetate 5-Chlorothieno[3,2-b]pyridine-2-sulfonic acid [1-(3-cyanobenzyl)-2-oxo-pyrrolidin-3-(S)-yl]-methylamide is converted to the title compound as described in EXAMPLE 1, Part F. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to afford the title compound as a white solid.

$^1$H NMR (DMSO-d$_6$, 500 MHz) δ 9.32 (bs, 2H), 9.14 (bs, 2H), 8.69 (d, 1H), 8.24 (s, 1H), 7.70 (m, 1H), 7.66 (d, 1H), 7.58 (m, 2H), 7.56 (s, 1H), 5.00 (m, 1H), 4.44 (AB, 2H), 3.24 (m, 1H), 3.19 (m, 1H), 2.83 (s, 3H), 2.17 (m, 1H), 1.96 (m, 1H). FAB MS, [M+H]$^+$=478, 480, Cl pattern. Elemental analysis calculated with 1.3 mol H$_2$O: C=42.91%, H=3.87%, N=11.37%, found: C=42.90%, H=3.52%, N=11.07%.

EXAMPLE 29

3-[3-(S)-(6-Chlorothieno[2,3-b]pyridine-2-sulfonylamino)-2-oxo-pyrrolidin-1-ylmethyl]-benzamidine trifluroacetate

A. 2-Bromo-6-chlorothieno[2,3-b]pyridine

The title compound is prepared from 2-bromo-5-acetyl thiophene according to the procedure described in *J. Chem. Soc., Perkin Trans. I*, 1981, 1531. The crude product is purified by column chromatography eluting with 2% EtOAc/ hexanes to afford a white solid.

$^1$H NMR (CDCl$_3$, 300 MHz) δ 7.89 (d, 1H), 7.28 (d, 1H), 7.27 (d, 1H).

B. 6-Chlorothieno[2,3-b]pyridine-2-sulfonyl chloride

The title compound is prepared as described in EXAMPLE 1, Part D using 2-bromo-6-chlorothieno[2,3-b] pyridine in place of thianaphthalene. The crude product is obtained as a white solid and is of sufficient purity to be used in the subsequent step.

$^1$H NMR (CDCl$_3$, 300 MHz) δ 8.22 (d, 1H), 8.09 (s, 1H), 7.52 (d, 1H). EI MS, [M]$^+$=267, 269, Cl pattern.

C. 6-Chlorothieno[2,3-b]pyridine-2-sulfonic acid [1-(3-cyanobenzyl)-2-oxo-pyrrolidin-3-(S)-yl]-amide The title compound is prepared from 3-(3-(S)-amino-2-oxo-pyrrolidin-1-ylmethyl)-benzonitrile hydrochloride as described in EXAMPLE 1, Part E using 6-chlorothieno[2,3-b]pyridine-2-sulfonyl chloride in place of benzo[b] thiophene-2-sulfonyl chloride. The crude product is purified by column chromatography eluting with a gradient of 10% EtOAc/CH$_2$Cl$_2$ to 25% EtOAc/CH$_2$Cl$_2$ to afford a white solid.

$^1$H NMR (CDCl$_3$, 300 MHz) δ 8.12 (d, 1H), 7.89 (s, 1H), 7.57 (m, 1H), 7.50 (s, 1H), 7.45 (m, 2H), 7.42 (d, 1H), 6.03 (bs, 1H) 4.48 (AB, 2H), 4.05 (m, 1H), 3.26 (m, 2H), 2.68 (m, 1H), 2.15 (m, 1H).

D. 3-[3-(S)-(6-Chlorothieno[2,3-b]pyridine-2-sulfonylamino)-2-oxo-pyrrolidin-1-ylmethyl]-benzamidine trifluoroacetate 6-Chlorothieno[2,3-b]pyridine-2-sulfonic acid [1-(3-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.1% TFA) and the appropriate product fractions are lyophilized to afford the title compound as a white solid.

$^1$H NMR (DMSO-d$_6$, 300 MHz) δ 9.29 (bs, 2H), 9.15 (bs, 2H), 8.88 (d, 1H), 8.48 (d, 1H), 8.08 (s, 1H), 7.68 (m, 2H), 7.56 (m, 3H), 4.42 (AB, 2H), 4.30 (m, 1H), 3.16 (m, 2H), 2.22 (m, 1H), 1.73 (m, 1H). FAB MS, [M+H]$^+$=464, 466, Cl pattern. Elemental analysis calculated with 1.5 mol H$_2$O Cal. C=41.69%, H=3.66%, N=11.58%, found: C=41.78%, H=3.28%, N=11.16%.

EXAMPLE 30

3-[3-(S)-(Thieno[2,3-b]pyridine-2-sulfonylamino)-2-oxo-pyrrolidin-1-ylmethyl]-benzamidine bistrifluoroacetate 3-[3-(S)-(6-Chlorothieno[2,3-b]pyridine-2-sulfonylamino)-2-oxo-pyrrolidin-1-ylmethyl]-benzamidine trifluroacetate is converted to the title compound as described in EXAMPLE 26. The reaction mixture is hydrogenated at room temperature for 3 days. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ 9.22 (bs, 2H), 9.04 (bs, 2H), 8.73 (d, 1H), 8.64 (m, 1H), 8.37 (d, 1H), 7.99 (s, 1H), 7.62 (m, 1H), 7.50 (m, 4H), 4.36 (AB, 2H), 4.21 (m, 1H), 3.08 (m, 2H), 2.13 (m, 1H), 1.67 (m, 1H). IS MS, [M+H]$^+$= 430.

EXAMPLE 31

3-{3-(S)-[(6-Chlorothieno[2,3-b]pyridine-2-sulfonyl)-methylamino]-2-oxo-pyrrolidin-1-ylmethyl}-benzamidine trifluroacetate

A. 6-Chlorothieno[2,3-b]pyridine-2-sulfonic acid [1-(3-cyanobenzyl)-2-oxo-pyrrolidin-3-(S)-yl]-methylamide The title compound is prepared as described in EXAMPLE 28, Part A using 6-chlorothieno[2,3-b]pyridine-2-sulfonic acid [1-(3-cyanobenzyl)-2-oxo-pyrrolidin-3-(S)-yl]-amide in place of 5-chlorothieno[3,2-b]pyridine-2-sulfonic acid [1-(3-cyanobenzyl)-2-oxo-pyrrolidin-3-(S)-yl]-amide. The crude product is purified by column chromatography eluting with a gradient of 5% EtOAc/CH$_2$Cl$_2$ to 10% EtOAc/CH$_2$Cl$_2$ to yield a white solid.

$^1$H NMR (CDCl$_3$, 300 MHz) δ 8.13 (d, 1H), 7.97 (s, 1H), 7.60 (m, 1H), 7.48 (m, 3H), 7.41 (d, 1H), 4.94 (m, 1H), 4.44 (AB, 2H), 3.25 (m, 2H), 2.93 (s, 3H), 2.44 (m, 1H), 2.09 (m, 1H).

B. 3-{3-(S)-[(6-Chlorothieno[2,3-b]pyridine-2-sulfonyl)-methylamino]-2-oxo-pyrrolidin-1-ylmethyl}-benzamidine trifluoroacetate 6-Chlorothieno[2,3-b]pyridine-2-sulfonic acid [1-(3-cyanobenzyl)-2-oxo-pyrrolidin-3-(S)-yl]-methylamide is converted to the title compound as described in EXAMPLE 1, Part F. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to afford the title compound as a white solid.

$^1$H NMR (DMSO-$d_6$, 500 MHz) δ 9.30 (bs, 2H), 9.03 (bs, 2H), 8.49 (d, 1H), 8.17 (s, 1H), 7.70 (d, 1H), 7.68 (m, 1H), 7.55 (m, 3H), 4.96 (m, 1H), 4.43 (AB, 2H), 3.19 (m, 2H), 2.81 (s, 3H), 2.15 (m, 1H), 1.97 (m, 1H). FAB MS, $[M+H]^+$= 478, 480, Cl pattern.

EXAMPLE 32

4-Hydroxy-3-[2-oxo-3-(S)-(5-chlorothienol[3,2-b] pyridine-2-sulfonylamino)-pyrrolidin-1-ylmethyl}-benzamidine trifluroacetate

A. 5-Chlorothienol[3,2-b]pyridine-2-sulfonic acid [1-(5-cyano-2-hydroxybenzyl)-2-oxo-pyrrolidin-3-(S)-yl]-amide The title compound is prepared from 4-hydroxy-3-(3-(S)-amino-2-oxo-pyrrolidin-1-ylmethyl)-benzonitrile hydrochloride as described in EXAMPLE 17, Part F using 5-chlorothieno[3,2-b]pyridine-2-sulfonyl chloride in place of 4,6-dichlorobenzo[b]thiophene-2-sulfonyl chloride. The product is obtained as a white solid.

$^1$H NMR (CDCl$_3$, 300 MHz) δ 9.40 (bs, 1H), 8.16 (d, 1H), 8.02 (s, 1H), 7.52 (dd, 1H), 7.43 (d, 1H), 7.38 (s, 1H), 6.96 (d, 1H), 5.65 (bs, 1H), 4.31 (AB, 2H), 4.10 (m, 1H), 3.46 (m, 2H), 2.68 (m, 1H), 2.15 (m, 1H).

B. 4-Hydroxy-3-[2-oxo-3-(S)-(5-chlorothieno[3,2-b]pyridine 2-sulfonylamino)-pyrrolidin-1-ylmethyl]-benzamidine trifluoroacetate 5-Chlorothieno[3,2-b]pyridine-2-sulfonic acid [1-(5-cyano-2-cyano-2-hydroxybenzyl)-2-oxo-pyrrolidin-3-(S)-yl]-amide is converted to the title compound as described in EXAMPLE 1, Part F. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to afford the title compound as a white solid.

$^1$H NMR (DMSO-$d_6$, 300 MHz) δ 9.03 (bs, 2H), 8.93 (d, 1H), 8.75 (bs, 2H), 8.67 (d, 1H), 8.11 (s, 1H), 7.65 (d, 1H), 7.59 (dd, 1H), 7.41 (s, 1H), 6.97 (d, 1H), 4.33 (AB, 2H), 4.29 (m, 1H), 3.21 (m, 2H), 2.22 (m, 1H), 1.74 (m, 1H). IS MS, $[M+H]^+$=480, 482, Cl pattern. Elemental analysis calculated with 1.5 mol $H_2O$: C=40.62%, H=3.57%, N=11.27% found: C=41.02%, H=3.24%, N=10.86%.

EXAMPLE 33

4-Hydroxy-3-[2-oxo-3-(S)-(thieno[3,2-b]pyridine-2-sulfonylamino)-pyrrolidin-1-ylmethyl]-benzamidine bistrifluoroacetate 5-[3-(S)-(5-Chlorothieno[3,2-b]pyridine-2-oxo-pyrrolidin-1-ylmethyl]-2-hydroxy-benzamidine trifluroacetate is converted to the title compound as described in EXAMPLE 26. The reaction mixture is hydrogenated at room temperature for 7 days. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ 9.03 (bs, 2H), 8.85 (bs, 2H), 8.83 (d, 1H), 8.78 (d, 1H), 8.60 (d, 1H), 8.12 (s, 1H), 7.61 (d, 1H), 7.53 (dd, 1H), 7.42 (s, 1H), 6.97 (d, 1H), 4.33 (AB, 2H), 4.28 (m, 1H), 3.22 (m, 2H), 2.22 (m, 1H), 1.76 (m, 1H). FAB MS, $[M+H]^+$=446.

EXAMPLE 34

4-Hydroxy-3-[2-oxo-3-(S)-(5-chlorothieno[3,2-b] pyridine-2-sulfonylamino)-pyrrolidin-1-ylmethyl]-hydroxybenzamidine trifluoroacetate 5-Chlorothieno[3,2-b]pyridine-2-sulfonic acid [1-(5-cyano-2-hydroxybenzyl)-2-oxo-pyrrolidin-3-(S)-yl]-amide is converted to the title compound as described in EXAMPLE 27. The crude product is purified by RP-HPLC eluting in a gradient of 10% $CH_3CN/H_2O$ (0.1% TFA) TO 80% $CH_3CN/H_2O$ (0.1% TFA) and the appropriate product fractions are lyophilized to provide the title compound as a white solid.

$^1$H NMR (DMSO-$d_6$, 300 MHz) δ 8.93 (d, 1H), 8.89 (bs, 1H), 8.68 (d, 1H), 8.11 (s, 1H), 7.65 (d, 1H), 7.48 (d, 1H), 7.30 (s, 1H, 6.97 (d, 1H), 4.32 (AB, 2H), 4.28 (m, 1H), 3.20 (m, 2H), 2.22 (m, 1H), 1.73 (m, 1H). FAB MS, $[M+H]^+$= 496, 498, Cl pattern.

EXAMPLE 35

4-Amino-3-[2-oxo-3-(S)-(5-chlorothieno[3,2-b] pyridine-2-sulfonylamino)-pyrrolidin-1-ylmethyl]-benzamidine trifluoroacetate

A. 5-Chlorothieno[3,2-b]pyridine-2-sulfonic acid [1-(2-amino-5-cyanobenzyl)-2-oxo-pyrrolidin-3-(S)-yl]-amide The title compound is prepared from 4-amino-3-(3-(S)-amino-2-oxo-pyrrolidin-1-ylmethyl)-benzonitrile dihydrochloride as described in EXAMPLE 17, Part F using 5-chlorothieno[3,2-b]pyridine-2-sulfonyl chloride in place of 4,6-dichlorobenzo[b]thiophene-2-sulfonyl chloride. The crude product is purified by column chromatography eluting with a gradient of 10% EtOAc/$CH_2Cl_2$ to 25% EtOAc/$CH_2cl_2$ to afford a white solid.

$^1$H NMR (CDCl$_3$, 300 MHz) δ 8.16 (d, 1H), 8.03 (s, 1H), 7.44 (d, 1H), 7.38 (dd, 1H), 7.28 (dd, 1H), 6.60 (d, 1H), 5.55 (bs, 1H), 4.86 (bs, 2H), 4.29 (AB, 2H), 4.00 (m, 1H), 3.26 (m, 2H), 2.66 (m, 1H), 2.09 (m, 1H).

B. 4-Amino-3-[2-oxo-3-(S)-(5-chlorothienol[3,2-b] pyridine-2-sulfonylamino)-pyrrolidin-1-ylmethyl]-benzamidine trifluoroacetate 5-Chlorothieno[3,2-b]pyridine-2-sulfonic acid [1-(2-amino-5-cyanobenzyl)-2-oxo-pyrrolidin-3-(S)-yl]-amide is converted to the title compound as described in EXAMPLE 1, Part F. The crude product is purified by RP-HPLC eluting in a gradient of 10% $CH_3CN/H_2O$ (0.1% TFA) TO 70% $CH_3CN/H_2O$ (0.1% TFA) and the appropriate product fractions are lyophilized to afford the title compound as a white solid.

$^1$H NMR (DMSO-$d_6$, 300 MHz) δ 8.94 (d, 1H), 8.80 (bs, 2H), 8.68 (d, 1H), 8.40 (bs, 2H), 8.11 (s, 1H), 7.65 (d, 1H), 7.54 (dd, 1H), 7.44 (s, 1H), 6.72 (d, 1H), 6.19 (bs, 2H), 4.33 (m, 1H), 4.20 (AB, 2H), 3.20 (m, 2H), 2.22 (m, 1H), 1.70 (m, 1H). FAB MS, $[M+H]^+$=479, 481, Cl pattern. Elemental analysis calculated with 2.0 mol $H_2O$, 1.7 mol $CF_3CO_2H$, cal. C=39.99%, H=3.10%, N=12.49% found: C=40.03%, H=3.19%, N=12.67%.

EXAMPLE 36

4-Amino-3-[2-oxo-3-(S)-(thieno[3,2-b]pyridine-2-sulfonylamino)-pyrrolidin-1-ylmethyl]-benzamidine bistrifluoroacetate 4-Amino-3-[3-(S)-(5-chlorothieno[3,2-b]pyridine-2-sulfonylamino)-2-oxo-pyrrolidin-1-ylmethyl]-benzamidine trifluoroacetate is converted to the title compound as described in EXAMPLE 26. The reaction mixture is hydrogenated at room temperature for 7 days. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 8.85 (d, 1H), 8.78 (bs, 3H), 8.60 (d, 1H), 8.39 (bs, 2H), 8.11 (s, 1H), 7.53 (m, 1H), 7.52 (d, 1H), 7.42 (s, 1H), 6.71 (d, 1H), 6.17 (bs, 1H), 4.31 (m, 1H), 4.19 (AB, 1H), 3.19 (m, 2H), 2.20 (m, 1H), 1.69 (m, 1H). FAB MS, [M+H]$^+$=445.

EXAMPLE 37

4-[3-(S)-(5-Chlorothieno[3,2-b]pyridine-2-sulfonylamino)-2-oxo-pyrrolidin-1-ylmethyl]-thiophene-2-carboxamidine trifluoroacetate A. 5-Chlorothieno[3,2-b]pyridine-2-sulfonic acid [1-(5-cyanothiophen-3-ylmethyl)-2-oxo-pyrrolidin-3-(S)-yl]-amide The title compound is prepared from 4-(3-(S)-amino-2-oxo-pyrrolidin-1-ylmethyl)-thiophene-2-carbonitrile hydrochloride as described in EXAMPLE 1, Part E using 5-chlorothieno[3,2-b]pyridine-2-sulfonyl chloride in place of benzo[b]thiophene-2-sulfonyl chloride. The product is triturated with $Et_2O/CH_2Cl_2$/hexanes to give a white solid.

$^1$H NMR ($CDCl_3+CD_3OD$, 300 MHz) δ 8.20 (d, 1H), 8.03 (s, 1H), 7.50 (s, 1H), 7.48 (s, 1H), 7.43 (d, 1H), 4.41 (AB, 2H), 4.08 (m, 1H), 3.27 (m, 2H), 2.58 (m, 1H), 2.05 (m, 1H).

B. 4-[3-(S)-(5-Chlorothieno[3,2-b]pyridine-2-sulfonylamino)-2-oxo-pyrrolidin-1-ylmethyl]-thiophene-2-carboxamidine trifluoroacetate 5-Chlorothieno[3,2-b]pyridine-2-sulfonic acid [1-(5-cyanothiophen-3-ylmethyl)-2-oxo-pyrrolidin-3-(S)-yl]-amide is converted to the title compound as described in EXAMPLE 1, Part F. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to afford the title compound as a white solid.

$^1$H NMR (DMSO-$d_6$, 300 MHz) δ 9.26 (bs, 2H), 9.12 (bs, 2H), 8.92 (d, 1H), 8.67 (d, 1H), 8.10 (s, 1H), 7.89 (s, 1H), 7.81 (s, 1H), 7.63 (d, 1H), 4.37 (AB, 2H), 4.28 (m, 1H), 3.19 (m, 2H), 2.22 (m, 1H), 1.73 (m, 1H). FAB MS, [M+H]$^+$=470, 472, Cl pattern. Elemental analysis calculated with 2.1 mol $H_2O$, 1.8 mol $CF_3CO_2H$, Cal. C=36.64%, H=2.66%, N=10.37% found: C=36.70%, H=2.78%, N=10.38%.

EXAMPLE 38

4-[3-(S)-(5-Chlorothieno[3,2-b]pyridine-2-sulfonylamino)-2-oxo-pyrrolidin-1-ylmethyl]-thiophene-2-hydroxycarboxamadine trifluoroacetate 5-Chlorothieno[3,2-b]pyridine-2-sulfonic acid [1-(5-cyanothiophen-3-ylmethyl)-2-oxo-pyrrolidin-3-(S)-yl]-amide is converted to the title compound as described in EXAMPLE 27. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ 8.91 (d, 1H), 8.68 (d, 1H), 8.11 (s, 1H), 7.65 (dd, 1H), 7.55 (s, 1H), 7.47 (s, 1H), 4.33 (AB, 2H), 4.28 (m, 1H), 3.18 (m, 2H), 2.22 (m, 1H), 1.72 (m, 1H). FAB MS, [M+H]$^+$=486, 488, Cl pattern. Elemental analysis calculated with 1.5 mol $H_2O$ cal. C=36.42%, H=3.21%, N=11.18%, found: C=36.43%, H=2.77%, N=10.83%.

EXAMPLE 39

4-{3-(S)-[(5-Chlorothieno[3,2-b]pyridine-2-sulfonyl)-methylamino]-2-oxo-pyrrolidin-1-ylmethyl}-thiophene-2-carboxamidine trifluoroacetate A. 5-Chlorothieno[3,2-b]pyridine-2-sulfonic acid [1-(5-cyanothiophen-3-ylmethyl)-2-oxo-pyrrolidin-3-(S)-yl]-methylamide The title compound is prepared as described in EXAMPLE 28, Part A using 5-chlorothieno[3,2-b]pyridine-2-sulfonic acid [1-(5-cyanothiophen-3-ylmethyl)-2-oxo-pyrrolidin-3-(S)-yl]-amide in place of 5-chlorothieno[3,2-b]pyridine-2-sulfonic acid [1-(3-cyanobenzyl)-2-oxo-pyrrolidin-3-(S)-yl]-amide. The crude product is obtained as a white solid.

$^1$H NMR ($CDCl_3$, 300 MHz) δ 8.20 (d, 1H), 8.05 (s, 1H), 7.48 (s, 1H), 7.45 (s, 1H), 7.40 (d, 1H), 4.91 (m, 1H), 4.40 (AB, 2H), 3.30 (m, 2H), 2.90 (s, 3H), 2.40 (m, 1H), 2.05 (m, 1H).

B. 4-{3-(S)-[5-Chlorothieno[3,2-b]pyridine-2-sulfonyl)-methylamino]-2-oxo-pyrrolidin-1-yl methyl}-thiophene-2-carboxamidine trifluoroacetate 5-Chlorothieno[3,2-b]pyridine-2-sulfonic acid [1-(5-cyanothiophen-3-ylmethyl)-2-oxo-pyrrolidin-3-(S)-yl]-methylamide is converted to the title compound as described in EXAMPLE 1, Part F. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 9.25 (bs, 2H), 8.98 (bs, 2H), 8.70 (d, 1H), 8.23 (s, 1H), 7.91 (s, 1H), 7.80 (s, 1H), 7.66 (d, 1H), 4.95 (m, 1H), 4.36 (AB, 2H), 3.22 (m, 2H), 2.79 (s, 3H), 2.13 (m, 1H), 1.94 (m, 1H). FAB MS, [M+H]$^+$=484, 486, Cl pattern. Elemental analysis calculated with 1.3 mol $H_2O$, 1.5 mol $CF_3CO_2H$, C=38.5%, H=3.00%, N=10.69% found: C=38.69%, H=2.99%, N=10.72%.

EXAMPLE 40

3-{3-(S)-[5-(2-Methylsulfanyl-pyrimidin-4-yl)-thiophene-2-sulfonylamino]-2-oxo-pyrrolidin-1-ylmethyl}-benzamidine trifluoroacetate A. 3-(3-(S)-amino-2-oxo pyrrolidin-1-ylmethyl)-benzamidine bistrifluroacetate

[1-(3-Cyanobenzyl)-2-oxo-pyrrolidin-3-(S)-yl]-carbamic acid tert-butyl ester is converted to the title compound as described in EXAMPLE 1, Part F. The crude product is purified by RP-HPLC eluting in a gradient of 2% $CH_3CN/H_2O$ (0.1% TFA) to 30% $CH_3CN/H_2O$ (0.1% TFA) and the appropriate product fractions are lyophilized to afford the title compound as a white solid.

$^1$H NMR (DMSO-$d_6$, 300 MHz) δ 9.36 (bs, 2H), 9.28 (bs, 2H), 8.47 (bs, 3H), 7.75 (m, 1H), 7.65 (s, 1H), 7.62 (m, 2H), 4.55 (AB, 2H), 4.13 (m, 1H), 3.33 (m, 2H), 2.40 (m, 1H), 1.94 (m, 1H). FAB MS, [M+H]$^+$=233. Elemental analysis B. 3-{3-(S)-[5-(2-Methylsulfanyl-pyrimidin-4-yl)-thiophene-2-sulfonylamino]-2-oxo-pyrrolidin-1-ylmethyl}-benzamidine trifluoroacetate The title compound is prepared from 3-(3-(S)-amino-2-oxo-pyrrolidin-1-ylmethyl)-benzamidine bistrifluroacetate as described in EXAMPLE 1, Part E using 5-[2-(methylthio)-pyrimidin-4-yl]thiophene-2-sulfonyl chloride in place of benzo[b]thiophene-2-sulfonyl chloride. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ 9.28 (bs, 2H), 8.98 (bs, 2H), 8.71 (d, 1H), 8.62 (d, 1H), 8.09 (d, 1H), 7.80 (d, 1H), 7.74 (d, 1H), 7.67 (m, 1H), 7.57 (m, 3H), 4.43 (AB, 2H), 4.25 (m, 1H), 3.14 (m, 2H), 2.55 (s, 3H), 2.18 (m, 1H), 1.70 (m, 1H). FAB MS, [M+H]$^+$=503.

EXAMPLE 41

3-{3-(S)-[5-(2-Methoxy-pyrimidin-4-yl)-thiophene-2-sulfonylamino]-2-oxo-pyrrolidin-1-ylmethyl}-benzamidine trifluroacetate A. [5-(2-Methylsulfanyl-pyrimidin-4-yl)-thiophene-2-sulfonic acid [1-(3-cyanobenzyl)-2-oxo-pyrrolidin-3-(S)-yl]-amide The title compound is prepared from 3-(3-(S)-amino-2-oxo-pyrrolidin-1-ylmethyl)-benzonitrile hydrochloride as described in EXAMPLE 1, Part E using 5-[2-(methylthio)-pyrimidin-4-yl]thiophene-2-sulfonyl chloride in a place of benzo[b]thiophene-2-sulfonyl chloride. The crude product is obtained as a white solid and is of sufficient purity to be used in the subsequent step.

$^1$H NMR (CDCl$_3$, 300 MHz) δ 8.55 (d, 1H), 7.70 (d, 1H), 7.65 (d, 1H), 7.60 (m, 1H), 7.50 (s, 1H), 7.46 (m, 2H), 7.23 (d, 1H), 5.84 (s, 1H), 4.48 (s, 2H), 3.97 (m, 1H), 3.28 (m, 2H), 2.66 (m, 1H), 2.60 (s, 3H), 2.15 (m, 1H).

B. [5-(2-Methylsulfinyl-pyrimidin-4-yl)-thiophene-2-sulfonic acid [1-(3-cyanobenzyl)-2-oxo-pyrrolidin-3-(S)-yl]-amide and [5-(2-Methylsulfonyl-pyrimidin-4-yl)-thiophene-2-sulfonic acid [1-(3-cyanobenzyl)-2-oxo-pyrrolidin-3-(S)-yl]-amide To a solution of [5-(2-methylsulfanyl-pyrimidin-4-yl)-thiophene-2-sulfonic acid [1-(3-cyanobenzyl)-2-oxo-pyrrolidin-3-(S)-yl]-amide (1.48 g, 3.05 mmol) in 30 mL of CHCl$_3$ at 0 C. is added dropwise a solution of 3-chloroperoxybenzoic acid (75%, 1.05 g, 4.58 mmol) in 50 mL of CHCl$_3$. The resulting solution is allowed to warm to room temperature and is stirred for 16 hours. The reaction mixture is diluted with CH$_2$Cl$_2$ and washed successively with a saturated solution of Na$_2$CO$_3$, 10% Na$_2$CO$_3$ and H$_2$O. The organic phase is then dried over MgSO$_4$, filtered and concentrated in vacuo to give a mixture of the title compounds (1.46 g, 2.82 mmol) as a solid which is of sufficient purity to be used in the subsequent step.

FAB MS, [M+H]$^+$=502, 518.

C. [5-(2-Methoxy-pyrimidin-4-yl)-thiophene-2-sulfonic acid [1-(3-cyanobenzyl)-2-oxo-pyrrolidin-3-(S)-yl]-amide A mixture of [5-(2-methylsulfinyl-pyrimidin-4-yl)-thiophene-2-sulfonic acid [1-(3-cyanobenzyl)-2-oxo-pyrrolidin-3-(S)-yl]-amide and [5-(2-methylsulfonyl-pyrimidin-4-yl)-thiophene-2-sulfonic acid [1-(3-cyanobenzyl)-2-oxo-pyrrolidin-3-(S)-yl]-amide (0.19 g, 0.37 mmol) is dissolved in 10 mL of MeOH and 1 mL of CH$_2$Cl$_2$ and NH$_3$ gas is bubbled through the solution for 5 minutes. The resulting mixture is heated at reflux for 4 hours. After this time, the solution is concentrated in vacuo to give the title compound (0.17 g, 0.36 mmol) as a solid.

$^1$H NMR (DMSO-$d_6$, 300 MHz) δ 8.70 (d, 1H), 8.09 (d, 1H), 7.75 (m, 3H), 7.66 (s, 1H), 7.55 (m, 3H), 4.42 (AB, 2H), 4.27 (m, 1H), 3.95 (s, 3H), 3.15 (m, 2H), 2.17 (m, 1H), 1.68 (m, 1H).

D. 3-{3-(S)-[5-(2-Methoxy-pyrimidin-4-yl)-thiophene-2-sulfonylamino]-2-oxo-pyrrolidin-1-ylmethyl}-benzamidine trifluoroacetate

[5(2-Methoxy-pyrimidin-4-yl)-thiophene-2-sulfonic acid [1-(3-cyanobenzyl)-2-oxo-pyrrolidin-3-(S)-yl]-amide is converted to the title compound as described in EXAMPLE 1, Part F. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to afford the title compound as a white solid.

$^1$H NMR (DMSO-$d_6$, 300 MHz) δ 9.29 (bs, 2H), 9.11 (bs, 2H), 8.70 (d, 1H), 8.62 (d, 1H), 8.09 (d, 1H), 7.75 (m, 2H), 7.68 (m, 1H), 7.57 (m, 3H), 4.45 (AB, 2H), 4.25 (m, 1H), 3.95 (s, 3H), 3.16 (m, 2H), 2.18 (m, 1H), 1.70 (m, 1H). FAB MS, [M+H]$^+$=487. Elemental analysis calculated with 2.5 mol H$_2$O: C=42.70%, H=4.39%, N=12.99%, found: C=42.69%, H=3.64%, N=12.28%.

EXAMPLE 42

3-{3-(S)-[5-(2-Amino-pyrimidin-4-yl)-thiophene-2-sulfonylamino]-2-oxo-pyrrolidin-1-ylmethyl}-benzamidine bistrifluoroacetate A mixture of [5-(2-methylsulfinyl-pyrimidin-4-yl)-thiophene-2-sulfonic acid [1-(3-cyanobenzyl)-2-oxo-pyrrolidin-3-(S)-yl]-amide and [5-(2-methylsulfonyl-pyrimidin-4-yl)-thiophene-2-sulfonic acid [1-(3-cyanobenzyl)-2-oxo-pyrrolidin-3-(S)-yl]-amide (0.20 g, 0.39 mmol) is dissolved in 10 mL of EtOH and NH$_3$ gas is bubbled through the solution for 5 minutes. The resulting mixture is heated at 90° C. for 3 hours in a stainless steel Parr high pressure reaction vessel. After this time, the solution is allowed to cool to room temperature and is concentrated in vacuo to give [5-(2-amino-pyrimidin-4-yl)-thiophene-2-sulfonic acid [1-(3-cyanobenzyl)-2-oxo-pyrrolidin-3-(S)-yl]-amide (0.20 g) as a crude product. FAB MS, [M+H]$^+$=455. The crude [5-(2-amino-pyrimidin-4-yl)-thiophene-2-sulfonic acid [1-(3-cyanobenzyl)-2-oxo-pyrrolidin-3-(S)-yl]-amide is converted to the title compound as described in EXAMPLE 1, Part F. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ 9.29 (bs, 2H), 9.08 (bs, 2H), 8.55 (d, 1H), 8.33 (d, 1H), 7.93 (d, 1H), 7.68 (m, 2H), 7.57 (m, 3H), 7.20 (d, 1H), 7.01 (bs, 1H), 4.45 (AB, 2H), 4.22 (m, 1H), 3.15 (m, 2H), 2.15 (m, 1H), 1.68 (m, 1H). FAB MS, [M+H]$^+$=472.

EXAMPLE 43

3-{3-(S)-([5-(2-Amino-pyrimidin-4-yl)-thiophene-2-sulfonyl]-methylamino)-2-oxo-pyrrolidin-1-ylmethyl}-benzamidine bistrifluoroacetate

A. [5-(2-Methylsulfinyl-pyrimidin-4-yl)-thiophene-2-sulfonic acid [1-(3-cyanobenzyl)-2-oxo-pyrrolidin-3-(S)-yl]-methylamide and [5-(2-Methylsulfonyl-pyrimidin-4-yl)-thiophene-2-sulfonic acid [1-(3-cyanobenzyl)-2-oxo-pyrrolidin-3-(S)-yl]-methylamide The title compounds are prepared as described in EXAMPLE 28, Part A using the mixture of [5-(2-methylsulfinyl-pyrimidin-4-yl)-thiophene-2-sulfonic acid [1-(3-cyanobenzyl)-2-oxo-pyrrolidin-3-(S)-yl]-amide and [5-(2-methylsulfonyl-pyrimidin-4-yl)-thiophene-2-sulfonic acid [1-(3-cyanobenzyl)-2-oxo-pyrrolidin-3-(S)-yl]-amide in place of 5-chlorothieno[3,2-b]pyridine-2-sulfonic acid [1-(3-cyanobenzyl)-2-oxo-pyrrolidin-3-(S)-yl]-amide. The mixture of crude products are obtained as a white solid.

$^1$H NMR (CDCl$_6$, 300 MHz) δ 8.94 (d, 1H), 7.90 (d, 1H), 7.84 (d, 1H), 7.73 (m, 1H), 7.62 (m, 1H), 7.46 (m, 3H), 4.93 (m, 1H), 4.43 (AB, 2H), 3.43 (s, 3H), 3.27 (m, 2H), 2.97 (s, 3H), 2.41 (m, 1H), 2.06 (m, 1H). FAB MS, [M+H]$^+$=516, 532.

B. 3-{3-(S)-([5-(2-Amino-pyrimidin-4-yl)-thiophene-2-sulfonyl]-methylamino)-2-oxo-pyrrolidin-1-ylmethyl}-benzamidine bistrifluoroacetate The title compound is prepared as described in EXAMPLE 42 using a mixture of [5-(2-methylsulfinyl-pyrimidin-4-yl)-thiophene-2-sulfonic acid [1-(3-cyanobenzyl)-2-oxo-pyrrolidin-3-(S)-yl]-methylamide and [5-(2-methylsulfonyl-pyrimidin-4-yl)-thiophene-2-sulfonic acid [1-(3-cyanobenzyl)-2-oxo-pyrrolidin-3-(S)-yl]-methylamide in place of the mixture of [5-(2-methylsulfinyl-pyrimidin-4-yl)-thiophene-2-sulfonic acid [1-(3-cyanobenzyl)-2-oxo-pyrrolidin-3-(S)-yl]-amide and [5-(2-methylsulfonyl-pyrimidin-4-yl)-thiophene-2-sulfonic acid [1-(3-cyanobenzyl)-2-oxo-pyrrolidin-3-(S)-yl]-amide. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to afford the title compound as a white solid.

$^1$H NMR (DMSO-d$_6$, 300 MHz) δ 9.29 (bs, 2H), 9.03 (bs, 2H), 8.36 (d, 1H), 7.98 (d, 1H), 7.75 (d, 1H), 7.68 (m, 1H), 7.56 (m, 3H, 7.21 (d, 1H), 6.95 (bs, 1H), 4.88 (m, 1H), 4.44 (AB, 2H), 3.18 (m, 2H), 2.74 (s, 3H), 2.07 (m, 1H), 1.89 (m, 1H), IS MS, [M+H]$^+$=486.

EXAMPLE 44

3-[3-(S)-(5'-Chloro-[2,2']-bithiophenyl-5-sulfonylamino)-2-oxo-pyrrolidin-1-ylmethyl]-benzamidine trifluroacetate

A. 5-Chloro-[2,2']bithiophenyl

The title compound is prepared from 2-chloro-thiophene according to the procedure described in *Bull. Chem. Soc. Japan*, 1979, 1126. The crude product is purified by column chromatography eluting with a gradient of 5% EtOAc/hexanes to 10% EtOAc/hexanes to afford a white solid.

$^1$H NMR (CDCl$_3$, 300 MHz) δ 7.24 (m, 1H), 7.11 (d, 1H), 7.03 (dd, 1H), 6.94 (d, 1H), 6.83 (d, 1H). EI MS, [M]$^+$=200, 202, Cl pattern.

B. 5'-Chloro-[2,2']bithiophenyl-5-sulfonyl chloride

The title compound is prepared as described in EXAMPLE 1, Part D using 5-chloro-[2,2']bithiophenyl in place of thianaphthalene. The crude product is purified by column chromatography eluting with a gradient of 5% EtOAc/hexanes to 10% EtOAc/hexanes to give a white solid $^1$H NMR (CDCl$_3$, 300 MHz) δ 7.76 (d, 1H), 7.14 (d, 1H), 7.09 (d, 1H), 6.92 (d, 1H). EI MS, [M]$^+$=298, 300, Cl pattern.

C. 5'-Chloro-[2,2']-bithiophenyl-5-sulfonic acid [1-(3-cyanobenzyl)-2-oxo-pyrrolidin-3-(S)-yl]-amide The title compound is prepared from 3-(3-(S)-amino-2-oxo-pyrrolidin-1-ylmethyl)-benzonitrile hydrochloride as described in EXAMPLE 1, Part E using 5'-chloro-[2,2'] bithiophenyl-5-sulfonyl chloride in place of benzo[b] thiophene-2-sulfonyl chloride. The crude product is triturated with EtOAc/CH$_2$Cl$_2$ to yield a beige solid.

$^1$H NMR (CDCl$_3$, 300 MHz) δ 7.62 (m, 1H), 7.56 (d, 1H), 7.50 (m, 2H), 7.48 (d, 1H), 7.06 (d, 1H), 7.04 (d, 1H), 6.90 (d, 1H), 5.54 (s, 1H), 4.48 (s, 2H), 3.93 (m, 1H), 3.27 (m, 2H), 2.65 (m, 1H), 2.15 (m, 1H).

D. 3-[3-(S)-(5'-Chloro-[2,2']-bithiophenyl-5-sulfonylamino)-2-oxo-pyrrolidin-1-ylmethyl]-benzamidine trifluoroacetate 5'-Chloro-[2,2']-bithiophenyl-5-sulfonic acid [1-(3-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ 9.30 (bs, 2H), 9.19 (bs, 2H), 8.56 (d, 1H), 7.68 (m, 1H), 7.62 (d, 1H), 7.58 (m, 3H), 7.36 (d, 1H), 7.34 (d, 1H), 7.19 (d 1H), 4.46 (AB, 2H), 4.22 (m, 1H), 3.17 (m, 2H), 2.18 (m, 1H), 1.70 (m, 1H). FAB MS, [M+H]$^+$=495, 497, Cl pattern. Elemental analysis calculated with 0.9 mol H$_2$O: C=42.23%, H=3.52%, N=8.95%, found: C=42.22%, H=3.02%, N=8.62%.

EXAMPLE 45

4-Amino-3-[3-(S)-benzo[b]thiophene-2-sulfonylamino)-2-oxopyrrolidin-1-ylmethyl] benzamidine trifluoroacetate

A. Benzo[b]thiophene-2-sulfonic acid [1-(4-amino-3-cyanobenzyl)-2-oxo-pyrrolidin-3-(S)-yl]amide The title compound (0.131 g, 0.307 mmol) is prepared as in EXAMPLE 1, Part E from 4-amino-3-(3-(S)-amino-2-oxo-pyrrolidin-1-ylmethyl)benzonitrile dihydrochloride (0.135 g, 0.445 mmol) and benzo[b]thiophene-2-sulfonyl chloride (0.114 g, 0.49 mmol) in acetonitrile.

$^1$H NMR (CDCl$_3$, 300 MHz) δ 7.88–7.94 (m, 3H), 7.48 (m, 2H), 7.36 (dd, 1H), 7.28 (d, 1H), 6.58 (d, 1H), 5.36 (d, 1H), 4.88 (bs, 2H), 4.30 (AB, 2H), 3.94 (m, 1H), 3.26 (m, 2H), 2.65 (m, 1H), 2.10 (m, 1H); FAB MS, [M+H]$^+$=427.

B. 4-Amino-3-[3-(S)-benzo[b]thiophene-2-sulfonylamino-2-oxopyrrolidin-1-ylmethyl] benzamidine trifluoroacetate The title compound was prepared from benzo[b] thiophene-2-sulfonic acid [1-(4-amino-3-cyanobenzyl)-2- oxo-pyrrolidin-3-(S)-yl]amide (0.131 g, 0.307 mmol) as described in EXAMPLE 1, Part F. The crude product is purified by RP-HPLC eluting with a gradient of 10% CH$_3$CN/H$_2$O (0.1% TFA) to 100% CH$_3$CN. The appropriate fractions are lyophilized to provide 4-amino-3-[3-(S)-benzo[b]thiophene-2-sulfonylamino-2-oxopyrrolidin-1-ylmethyl]benzamidine trifluoroacetate as a white solid (0.08 g, 0.14 mmol). $^1$H NMR (DMSO-d$_6$, 300 MHz) δ 8.80 (bs, 2H), 8.67 (d, 1H), 8.39 (bs, 2H), 8.0–8.12 (m, 3H), 7.47–7.57 (m, 3H), 7.43 (m, 1H), 6.73 (d, .21 (bs, 2H), 4.28 (m, 1H), 4.22 (m, 2H), 3.18 (m, 2H), 2.17 (m, 1H), 1.67 (m, 1H). FAB MS, [M+H]$^+$=444. Elemental analysis calculated with 1.6 mol H$_2$O cal. C=45.06%, H=4.33%, N=11.94%, found: C=45.41%, H=4.07%, N=11.47%.

EXAMPLE 46

4-Amino-3-[6-chlorobenzo[b]thiophene-2-sulfonylamino)-2-oxopyrrolidin-1-ylmethyl]benzamidine trifluoroacetate A. 6-Chlorobenzo[b]thiophene-2-sulfonic acid [1-(4-amino-3-cyanobenzyl)-2-oxo-pyrrolidin-3-(S)-yl]amide The title compound (0.133 g, 0.288 mmol) is prepared as in EXAMPLE 1, Part E from 4-amino-3-(3-(S)-amino-2-oxo-pyrrolidin-1-ylmethyl)benzonitrile (0.175 g, 0.758 mmol) and 6-chlorobenzo[b]thiophene-2-sulfonyl chloride (0.203 g, 0.758 mmol).

$^1$H NMR (CDCl$_3$, 300 MHz) δ 7.89 (s, 1H), 7.86 (d, 1H), 7.82 (d, 1H), 7.45 (dd, 1H), 7.37 (dd, 1H), 7.29 (d, 1H), 6.60 (d, 1H), 5.41(bs, 1H), 4.89 (bs, 2H), 4.28 (AB, 2H), 3.97 (m, 1H), 3.28 (m, 2H), 2.64 (m, 1H), 2.09 (m, 1H). FAB MS, [M+H]$^+$=461, 463 Cl pattern.

B. 4-Amino-3-[6-chlorobenzo[b]thiophene-2-sulfonylamino)-2-oxopyrrolidin-1-ylmethyl]benzamidine trifluoroacetate The title compound was prepared from 6-chlorobenzo[b]thiophene-2-sulfonic acid [1-(4-amino-3-cyanobenzyl)-2-oxo-pyrrolidin-3-(S)-yl]amide (0.131 g, 0.284 mmol) as described in EXAMPLE 1, Part F. The crude product is purified by RP-HPLC eluting with a gradient of 10% CH$_3$CN/H$_2$O (0.1% TFA) to 100% CH$_3$CN. The appropriate fractions are lyophilized to provide the title compound as a solid (0.126 g, 0.207 mmol).

$^1$H NMR (DMSO-d$_6$, 300 MHz) δ 8.80 (bs, 2H), 8.73 (d, 1H), 8.43 (bs, 2H), 8.29 (s, 1H), 8.05 (s, 1H), 8.02 (d, 1H), 7.57 (m, 2H), 7.44 (s, 1H), 6.73 (dd, 1H), 6.20 (bs, 2H), 4.1–4.25 (m, 3H), 3.20 (m, 2H), 2.18 (m, 1H), 1.68 (m, 1H). FAB MS, [M+H]$^+$=478, 480, Cl pattern. Elemental analysis calculated with 1.4 mol H$_2$O: C=42.84%, H=3.88%, N=11.35%, found: C=42.84%, H=3.74%, N=11.05%.

EXAMPLE 47

4-Amino-3-[6-chlorobenzo[b]thiophene-2-sulfonylamino)-2-oxopyrrolidin-1-ylmethyl]hydroxybenzamidine trifluoroacetate 6-chlorobenzo[b]thiophene-2-sulfonic acid [1-(4-amino-3-cyanobenzyl)-2-oxopyrrolidin-3-(S)-yl]amide (0.20 g, 0.434 mmol) was converted to the title compound (0.178 g, 0.36 mmol) by the methods described in EXAMPLE 27.

$^1$H NMR (DMSO-d$_6$, 300 MHz) δ 12.27 (bs, 1H), 10.80 (bs, 1H), 8.98 (bs, 1H), 8.74, (d, 1H), 8.65, (bs, 2H), 8.28, (s, 1H), 8.07 (s, 1H), 8.03 (d, 1H), 7.56 (dd, 1H), 7.39 (dd, 1H), 7.30 (s, 1H), 6.73 (d, 1H), 6.08 (bs, 1H), 4.12–4.28 (m, 3H), 3.18 (m, 2H), 2.17 (m, 1H), 1.68 (m, 1H).; Ion spray MS, [M]$^+$=495.

EXAMPLE 48

3-[2-Oxo-3-(S)-(5-pyridin-3-yl-thiophene-2-sulfonylamino)-pyrrolidin-1-ylmethyl]-benzamidine trifluoroacetate A. 2-Thiophene boronic acid To a solution of 2-bromothiophene (5.94 mL, 61.3 mmol) in 100 mL of ether at −60 ° C. is added n-butyl lithium (40 mL of a 1.6 M solution in hexanes, 64.4 mmol). After stirring for 30 minutes, tributylborate (23.7 mL, 85.9 mmol) is added and the mixture is stirred for 3 hours. The reaction mixture is warmed to room temperature overnight, and then treated with 150 mL of 1N HCl and washed with either (2×150 mL). The combined organic layers are extracted with 1N NaOH. The pH of the aqueous layer is adjusted to <7 using 1N HCl during which time a precipitate forms. The precipitate is collected and washed with hexane to give the product as an off-white solid (3.95 g, 30.9 mmol).

$^1$H NMR (CDCl$_3$, 300 MHz) δ 7.64 (dd, 1H), 7.59 (dd, 1H), 7.21 (dd, 1H), 4.75 (s, 2H). EI, [M]$^+$=128.

B. 3-Thiophene-2-yl-pyridine

A mixture of 3-bromopryidine (1.30 mL, 13.5 mmol) and tetrakis(triphenylphosphine) (0.468 g, 0.41 mmol) in 40 mL of dimethoxyethane is stirred under nitrogen at room temperature for 10 minutes. 2-Thiophene boronic acid (1.90 g, 14.8 mmol) and 20 mL of 1N sodium carbonate are added and the resulting mixture is refluxed overnight. The solution is cooled to room temperature and filtered through Celite. The filtrate is extracted with ether (2×30 mL). The combined organic layers are dried over MgSO$_4$, filtered and concentrated. The crude product is purified by column chromatography eluting with a gradient of 10% EtOAc/hexanes to 20% EtOAc/hexanes to afford the title compound (0.355 g, 2.20 mmol) as a light yellow oil.

$^1$H NMR (CDCl$_3$, 300 MHz) δ 8.89 (d, 1H), 8.52 (dd, 1H), 7.87 (ddd, 1H), 7.38 (s, 1H), 7.36 (d, 1H), 7.31, (m, 1H), 7.12 (dd, 1H). El, [M]$^+$=161.

C. 5-Pyridin-3-yl-thiophene-2-sulfonyl chloride

To a solution of 3-thiophen-2-yl-pyridine (0.35 g, 2.20 mmol) in 15 mL of THF at −78° C. is added n-BuLi (1.44 mL of a 1.6M solution in hexanes, 2.31 mmol). After stirring for 15 minutes, SO$_2$ gas is bubbled through the solution for 30 minutes. The solution is then allowed to warm to room temperature and stirred overnight. The solution is concentrated to dryness and the resulting solid is suspended in 20 mL of hexane. Sulfuryl chloride (0.185 mL, 2.31 mmol) is added and the reaction mixture is stirred for 30 minutes and then a small amount of methylene chloride is added and the mixture is stirred for another 30 minutes. The mixture is then concentrated to dryness and diluted with ethyl acetate and washed with saturated NaHCO$_3$ (aq), water and brine. The organic layer is dried over MgSO$_4$, filtered and concentrated to give a brown solid as the title product (0.452 g, 1.74 mmol) which is used in the subsequent step without further purification.

$^1$H NMR (CDCl$_3$, 300 MHz) δ 8.95 (bs, 1H), 8.70 (bs, 1H), 7.95 (d, 1H), 7.90 (d, 1H), 7.45 (bs, 1H), 7.44 (d, 1H). EI, [M]$^+$=259, 261, Cl pattern.

D. 5-Pyridin-3-yl-thiophene-2-sulfonic acid [1-(3-cyano-benzyl)-2-oxo-pyrrolidin-3-(S)-yl]-amide The title compound is prepared in CH$_3$CN instead of CH$_2$Cl$_2$ as described in EXAMPLE 1, Part E using 5-pyridin-3-yl-thiophene-2-sulfonyl chloride in place of benzo[b]thiophene-2-sulfonyl chloride. The crude product is obtained by diluting with ethyl acetate and washing with saturated sodium bicarbonate (aq), water and brine. The organic layer is dried over $MgSO_4$, filtered and concentrated. The title product is purified by column chromatography eluting with 5% $MeOH/CH_2Cl_2$ to give an off-white solid.

$^1$H NMR ($CDCl_3$, 300 MHz) δ 8.90 (d, 1H), 8.63 (d, 1H), 7.85 (dd, 1H), 7.68 (d, 1H), 7.61 (m, 1H), 7.41–7.45 (m, 3H), 7.34 (dd, 1H), 7.31 (d, 1H), 5.45 (s, 1H), 4.50 (s, 2H), 3.95 (m, 1H), 3.25 (m, 2H), 2.68 (m, 1H), 2.15 (m, 1H). FAB MS, [M+H]$^+$=439.

E. 3-[2-Oxo-3-(S)-(5-pyridin-3-yl-thiophene-2-sulfonylamino)-pyrrolidin-1-ylmethyl]-benzamidine trifluroacetate The title compound is prepared as described in EXAMPLE 1, Part F using 5-pyridin-3-yl-thiophene-2-sulfonic acid [1-(3-cyano-benzyl)-2-oxo-pyrrolidin-3-yl]-amide as the starting material. The crude product is purified by RP-HPLC eluting with a gradient of 10% $CH_3CN/H_2O$ (0.1% TFA) to 80% $CH_3CN/H_2O$ (0.1% TFA). The appropriate fractions are lyophilized to provide the title compound as a white solid.

$^1$H NMR (DMSO-$d_6$, 300 MHz) δ 9.30 (s, 2H), 9.05 (s, 2H), 8.95 (s, 1H), 8.63 (d, 1H), 8.55 (d, 1H), 8.16 (d, 1H), 7.65–7.71 (m, 3H), 7.48–7.60 (m, 4H), 4.48 (AB, 2H), 4.28 (m, 1H), 3.15 (m, 2H), 2.20 (m, 1H), 1.71 (m, 1H). FAB MS, [M+H]$^+$=456. Elemental analysis calculated with 0.8 mole of $H_2O$: C=43.02%, H=3.55%, N=10.03%; found: C=43.10%, H=3.85%, N=9.98%.

EXAMPLE 49

4-Amino-3-[2-oxo-3-(S)-(5-pyridin-3-yl-thiophene-2-sulfonylamino)-pyrrolidin-1-ylmethyl]-benzamidine trifluroacetate

A. 5-Pyridin-3-yl-thiophene-2-sulfonic acid [1-(2-amino-5-cyano-benzyl)-2-oxo-pyrrolidin-3-(S)-yl]-amide The title compound is prepared in $CH_3CN$ instead of $CH_2Cl_2$ as described in EXAMPLE 1, Part E using 5-pyridin-3-yl-thiophene-2-sulfonyl chloride in place of benzo[b]thiophene-2-sulfonyl chloride and substituting 4-amino-[3-(3-(S)-amino-2-oxo-pyrrolidin-1-ylmethyl)]-benzonitrile dihydrochloride for 3-(3-(S)-amino-2-oxo-pyrrolidin-1-ylmethyl)-benzonitrile hydrochloride. The crude product is obtained by diluting with ethyl acetate and washing with saturated sodium bicarbonate (aq.), water and brine. The organic layer is dried over MgSO, filtered and concentrated. The crude product is purified by column chromatography eluting with 50% $EtOAc/CH_2Cl_2$ to give a light brown solid.

$^1$H NMR ($CDCl_3$, 300 MHz) δ 8.85 (d, 1H), 8.61 (dd, 1H), 7.82 (m, 1H), 7.68 (d, 1H), 7.26–7.38 (m, 4H), 6.60 (d, 1H), 5.35 (d, 1H), 4.89 (d, 1H), 4.89 (s, 2H), 4.30 (AB, 2H), 3.97 (m, 1H), 3.30 (m, 2H), 2.65 (m, 1H), 2.09 (m, 1H). FAB MS, [M+H]$^+$=454.

B. 4-Amino-3-[2-oxo-3-(S)-(5-pyridin-3-yl-thiophene-2-sulfonylamino)-pyrrolidin-1-ylmethyl]-benzamidine trifluroacetate The title compound is prepared as described in EXAMPLE 1, Part F using 5-pyridin-3-yl-thiophene-2-sulfonic acid [1-(2-amino-5-cyano-benzyl)-2-oxo-pyrrolidin-3-yl]-amide as the starting material. The crude product is purified by RP-HPLC eluting with a gradient of 10% $CH_3CN/H_2O$ (0.1% TFA) to 80% $CH_3CN/H_2O$ (0.1% TFA). The appropriate fractions are lyophilized to provide the title compound as a white solid.

$^1$H NMR (DMSO-$d_6$, 300 MHz) δ 8.95 (d, 1H), 8.75 (s, 2H), 8.58 (d, 1H), 8.50 (d, 1H), 8.48 (s, 2H), 8.10 (d, 1H), 7.70 (s, 2H), 7.50 (m, 2H), 7.40 (d, 1H), 6.71 (d, 1H), 6.20 (bs, 2H), 4.11–4.25 (m, 3H), 3.15 (m, 2H), 2.18 (m, 1H), 1.62 (m, 1H). FAB MS, [M+H]$^+$=471.

EXAMPLE 50

4-Hydroxy-3-[2-oxo-3-(S)-(5-pyridin-3-yl-thiophene-2-sulfonylamino)-pyrrolidin-1-ylmethyl]-benzamidine trifluoroacetate

A. 5-Pyridin-3-yl-thiophene-2-sulfonic acid {1-[5-cyano-2-hydroxy-benzyl]-2-oxo-pyrrolidin-3-(S)-yl}-amide The title compound is prepared as described in EXAMPLE 17, Part G using 5-pyridin-3-yl-thiophene-2-sulfonyl chloride in place of 4,6-dichlorobenzo[b]thiophene-2-sulfonyl chloride. The solution is concentrated, and then purified by column chromatography eluting with 10% $MeOH/CH_2Cl_2$ to give a brown oil.

$^1$H NMR ($CDCl_3$, 300 MHz) δ 8.82 (bs, 1H), 8.61 (bs, 1H), 7.85 (d, 1H), 7.65 (d, 1H), 7.63 (d, 1H), 7.55 (s, 1H), 7.53 (dd, 1H), 7.41 (d, 1H), 7.31 (m, 1H), 7.28 (d, 1H), 6.91 (d, 1H), 4.41 (s, 2H, 4.12 (m, 1H), 3.35 (m, 2H), 2.55 (m, 1H), 2.09 (m, 1H). FAB MS, [M+H]$^+$=455.

B. 4-Hydroxy-3-[2-oxo-3-(S)-(5-pyridin-3-yl-thiophene-2-sulfonylamino)-pyrrolidin-1-ylmethyl]-benzamidine trifluoroacetate The title compound is prepared as described in EXAMPLE 1, Part F using 5-pyridin-3-yl-thiophene-2-sulfonic acid {1-[5-cyano-2-hydroxy-benzyl]-2-oxo-pyrrolidin-3-yl}-amide as the starting material. The crude product is purified by RP-HPLC eluting with a gradient of 10% $CH_3CN/H_2O$ (0.1% TFA) to 80% $CH_3CN/H_2O$ (0.1% TFA). The appropriate fractions are lyophilized to provide the title compound as a white solid.

$^1$H NMR (DMSO-$d_6$, 300 MHz) δ 10.91 (s, 1H), 9.06 (s, 2H), 8.98 (s, 8.67 (s, 2H), 8.61 (d, 1H), 8.55 (d, 1H), 8.16 (d, 1H), 7.71 (m, 2H), 7.60 (d, 1H), 7.51 (m, 1H), 7.42 (s, 1H), 7.00 (d, 1H), 4.35 (AB, 2H), 4.21 (m, 1H), 3.21 (m, 2H), 2.20 (m, 1H), 1.71 (m, 1H). FAB MS, [M+H]$^+$=472.

EXAMPLE 51

4-Hydroxy-3-[2-oxo-3-(S)-(5-pyridin-N-oxide-3-yl-thiophene-2-sulfonylamino)-pyrrolidin-1-ylmethyl]-benzamidine trifluoroacetate

A. 5-Pyridin-3-yl-thiophene-2-sulfonic acid {1-[2-(tert-butyl-dimethyl-silanyloxy)-5-cyano-benzyl]-2-oxo-pyrrolidin-3-(S)-yl}-amide Imidazole (0.094 g, 1.37 mol) and t-butyldimethylchlorosilane (0.099 g, 0.66 mmol) are added to a solution of 5-pyridin-3-yl-thiophene-2-sulfonic acid {1-[5-cyano-2-hydroxy-benzyl]-2-oxo-pyrrolidin-3-yl}-amide (0.25 g, 0.55 mmol) in 10 mL of DMF. The resulting mixture is stirred overnight, and then diluted with EtOAc and washed with saturated $NaHCO_3$ (aq) and brine. The organic layer is dried over MgSO₄, filtered and concentrated. The product is purified by column chromatography eluting with 3% MeOH/CH₂Cl₂ to give a brown oil (0.236 g, 0.41 mmol).

¹H NMR (CDCl₃, 300 MHz) δ 8.90 (bs, 1H), 8.52 (bs, 1H), 7.79 (m, 1H), 7.60 (d, 1H), 7.56 (dd, 1H), 7.45 (d, 1H), 7.39 (m, 1H), 7.28 (d, 1H), 7.22 (d, 1H), 6.80 (d, 1H), 6.70 (s, 1H), 4.40 (s, 2H), 4.03 (m, 1H), 3.21 (m, 2H), 2.60 (m, 1H), 2.10 (m, 1H), 0.92 (s, 9H), 0.20 (s, 6H).

B. 5-Pyridin-N-oxide-3-yl-thiophene-2-sulfonic acid {1-[2-(tert-butyl-dimethyl-silanyloxy)-5-cyano-benzyl]-2-oxo-pyrrolidin-3-(S)-yl}-amide To a solution of 5-pyridin-3-yl-thiophene-2-sulfonic acid {1-[2-(tert-butyl-dimethyl-silanyloxy)-5-cyano-benzyl]-2-oxo-pyrrolidin-3-(S)-yl}-amide (0.18 g, 0.32 mmol) in 10 mL of CH₂Cl₂, is added m-chloroperbenzoic acid (0.17 g, 0.63 mmol). The mixture is stirred overnight and then diluted with CH₂Cl₂ and washed with saturated NaHCO₃ (aq) and brine. The organic layer is dried over MgSO₄, filtered and concentrated to give the title product as a yellow oil (0.18 g, 0.32 mmol) which is used in the subsequent step without further purification.

¹H NMR (CDCl₃, 300 MHz) δ 10.70 (bs, 1H), 8.85 (s, 1H), 8.42 (d, 1H), 8.00 (s, 1H), 7.95 (d, 1H), 7.85 (s, 1H), 7.80 (d, 1H), 7.70 (m, 1H, 7.35 (d, 1H, 6.90 (d, 1H), 6.82 (d, 1H), 4.44 (s, 2H), 4.18 (m, 1H), 3.31 (m, 2H), 2.62 (m, 1H), 2.20 (m, 1H), 0.92 (s, 9H), 0.25 (s, 6H). FAB MS, [M+H]⁺=585.

C. 4-Hydroxy-3-[2-oxo-3-(S)-(5-pyridin-N-oxide-3-yl-thiophene-2-sulfonylamino)-pyrrolidin-1-ylmethyl]-benzamidine trifluoroacetate The title compound is prepared as described in EXAMPLE 1, Part F using 5-pyridin-N-oxide-3-yl-thiophene-2-sulfonic acid {1-[2-(tert-butyl-dimethyl-silanyloxy)-5-cyano-benzyl]-2-oxo-pyrrolidin-3-(S)-yl}-amide. The crude product is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz) δ 10.91 (s, 1H), 9.05 (s, 2H), 8.75 (s, 1H), 8.65 (s, 2H), 8.60 (d, 1H), 8.21 (d, 1H), 7.76 (d, 1H), 7.70 (d, 1H), 7.66 (d, 1H), 7.60 (dd, 1H), 7.49 (m, 1H), 7.41 (d, 1H), 6.98 (d, 1H), 4.35 (AB, 2H), 4.19 (m, 1H), 3.21 (m, 2H), 2.25 (m, 1H), 1.75 (m, 1H). FAB MS, [M+H]⁺=488.

EXAMPLE 52

3-[2-Oxo-3-(S)-(5-pyridin-4-yl-thiophene-2-sulfonylamino)-pyrrolidin-1-ylmethyl]-benzamidine trifluoroacetate A. 4-Thiophen-2-yl-pyridine The title compound is prepared as described in EXAMPLE 48, Part B using 4-bromopyridine in place of 3-bromopyridine. The crude product is purified by column chromatography eluting with a gradient of 20% EtOAc/hexanes to 40% EtOAc/hexanes to afford the title product as a white solid.

¹H NMR (CDCl₃, 300 MHz) δ 8.60 (d, 2H), 7.51 (m, 1H), 7.49 (d, 2H), 7.42 (dd, 1H), 7.14 (dd, 1H). EI, [M]⁺32 161.

B. 5-Pyridin-4-yl-thiophene-2-sulfonyl chloride

The title compound is prepared as described in EXAMPLE 48, Part C using 4-thiophen-2-yl-pyridine in place of 3-thiophen-2-yl-pyridine. The title compound is used in the subsequent step without further purification.

¹H NMR (CDCl₃, 300 MHz) δ 8.75 (d, 2H), 8.60 (d, 1H), 7.90 (d, 1H), 7.51 (d, 2H). EI, [M]⁺=259, 261, Cl pattern.

C. 5-Pyridin-4-yl-thiophene-2-sulfonic acid [1-(3-cyano-benzyl)-2-oxo-pyrrolidin-3-(S)-yl]-amide The title compound is prepared in CH₃CN instead of CH₂Cl₂ as described in EXAMPLE 1, Part E using 5-pyridin-4-yl-thiophene-2-sulfonyl chloride in place of benzo[b]thiophene-2-sulfonyl chloride. The crude product is obtained by diluting with ethyl acetate and washing with saturated sodium bicarbonate (aq), water and brine. The organic layer is dried over MgSO₄, filtered and concentrated. The title product is purified by column chromatography eluting with 5% MeOH/CH₂Cl₂ to give a light brown solid.

¹H NMR (CDCl₃, 300 MHz) δ 8.70 (d, 2H), 7.68 (d, 1H), 7.60 (m, 1H), 7.40–7.50 (m, 6H), 5.65 (bs, 1H), 4.48 (AB, 2H), 3.98 (m, 1H), 3.28 (m, 2H), 2.68 (m, 1H), 2.17 (m, 1H). FAB MS, [M+H]⁺=439.

D. 3-[2-Oxo-3-(S)-(5-pyridin-4-yl-thiophene-2-sulfonylamino)-pyrrolidin-1-ylmethyl]-benzamidine trifluroacetate The title compound is prepared as described in EXAMPLE 1, Part F using 5-pyridin-4-yl-thiophene-2-sulfonic acid [1-(3-cyano-benzyl)-2-oxo-pyrrolidin-3-yl]-amide as the starting material. The crude product is purified by RP-HPLC eluting with a gradient of 10% CH₃CN/H₂O (0.1% TFA) to 80% CH₃CN/H₂O (0.1% TFA). The appropriate fractions are lyophilized to provide the title compound as a white solid.

¹H NMR (DMSO-d₆, 300 MHz) δ 9.30 (s, 2H), 9.05 (s, 2H), 8.69 (d, 2H), 8.67 (d, 1H), 7.89 (d, 1H), 7.85 (d, 2H), 7.77 (d, 1H), 7.68 M, 2H), 7.51–7.60 (m, 3H), 4.42 (AB, 2h), 4.26 (M, 1h), 3.18 (m, 2H), 2.21 (m, 1H), 1.70 (m, 1H). FAB MS, [M+H]⁺=456.

EXAMPLE 53

3-[3-(S)-(4-chloro-thiophene-2-sulfonylamino)-2-oxo-pyrrolidin-1-ylmethyl]-benzamidine trifluroacetate A. 4-chloro-5-trimethylsilanyl-thiophene-2-sulfonyl chloride The title compound is prepared as described in EXAMPLE 48, Part C using (3-chloro-thiophen-2-yl)-trimethylsilane (prepared using the method described in WO 94/12505, PCT/US93/08613) in place of 3-thiophen-2-yl-pyridine.

¹H NMR (CDCl₃, 300 MHz) δ 7.10 (s, 1H), 0.30 (s, 9H). EI, [M]⁺=288, 290, Cl pattern.

B. 4-Chloro-5-trimethylsilanyl-thiophene-2-sulfonic acid [1-(3-cyano-benzyl)-2-oxo-pyrrolidin-3-(S)-yl]-amide and 4-chloro thiophene-2-sulfonic acid [1-(3-cyano-benzyl)-2-oxo-pyrrolidin-3-(S)-yl]-amide The title compound is prepared in CH₃CN instead of CH₂Cl₂ as described in EXAMPLE 1, Part E using 4-chloro-5-trimethylsilanyl-thiophene-2-sulfonyl chloride in place of benzo[b]thiophene-2-sulfonyl chloride. The crude product is obtained by diluting with ethyl acetate and washing with saturated sodium bicarbonate (aq), water and brine. The organic layer is dried over MgSO$_4$, filtered and concentrated. The title product is purified by column chromatography eluting with 3% MeOH/CH$_2$Cl$_2$ to give two products. 4-chloro-5-trimethylsilanyll-thiophene-2-sulfonic acid [1-(3-cyano-benzyl)-2-oxo-pyrrolidin-3-(S)-yl]-amide $^1$H NMR (CDCl$_3$, 300 MHz) δ 7.60 (m, 1H), 7.45–7.50 (m, 3H), 7.30 (s, 1H), 5.80 (bs, 1H), 4.50 (AB, 2H), 3.85 (m, 1H), 3.28 (m, 2H), 2.62 (m, 1H), 2.15 (m, 1H), 0.35 (s, 9H). FAB MS, [M+H]$^+$=396, 398, Cl pattern.

4-chloro-thiophene-2-sulfonic acid [1-(3-cyano-benzyl)-2-oxo-pyrrolidin-3-(S)-yl]-amide $^1$H NMR (CDCl$_3$, 300 MHz) δ 7.69 (m, 1H), 7.56 (d, 1H), 7.50 (m, 3H), 7.08 (d, 1H), 5.83 (bs, 1H), 4.48 (s, 2H), 3.85 (s, 1H), 3.21 (m, 2H), 2.60 (m, 1H), 2.11 (m, 1H), FAB MS, [M+H]$^+$=468, 470, Cl pattern.

C. 3-[3-(S)-(4-Chloro-thiophene-2-sulfonylamino)-2-oxo-pyrrolidin-1-ylmethyl]-benzamidine trifluoroacetate The title compound is prepared as described in EXAMPLE 1, Part F using 4-chloro-thiophene-2-sulfonic acid [1-(3-cyano-benzyl)-2-oxo-pyrrolidin-3-yl]-amide as the starting material. The crude product is purified by RP-HPLC eluting with a gradient of 10% CH$_3$CN/H$_2$O (0.1% TFA) to 80% CH$_3$LCN/H$_2$O (0.1% TFA). The appropriate fractions are lyophilized to provide the title compound as a white solid.

$^1$H NMR (DMSO-d$_6$, 300 MHz) δ 9.25 (bs, 2H), 8.91 (bs, 2H), 8.65 (m, 1H), 7.95 (d, 1H), 7.68 (m, 1H), 7.55 (m, 2H), 7.22 (d, 1H), 4.41 (AB, 2H), 4.20 (m, 1H), 3.18 (m, 2H), 2.10 (m, 1H), 1.75 (m, 1H). MS, [M+H]$^+$=413, 415, Cl pattern.

EXAMPLE 54

3-{3-(S)-[5-(5-Chloropyridin-3-yl)-thiophene-2-sulfonylamino]-2-oxopyrrolidin-1-ylmethyl}benzamidine trifluoroacetate

A. 5-Chloro-3-(thiophen-2-yl) pyridine

The title compound (0.21 g, 1.08 mmol) was prepared from 3,5-dichloropyridine (1.0 g, 6.76 mmol) and 2-thiophene boronic acid (0.95 g, 7.43 mmol) as described in EXAMPLE 48, Part B.

$^1$H NMR (CDCl$_3$, 300 MHz) δ 8.73 (d, 1H), 8.47 (d, 1H), 7.83 (dd, 1H), 7.34 (two dd, 2H), 7.10 (dd, 1H).

B. 5-(5-chloropyridin-3-yl)thiophene-2-sulfonylchloride 5-(5-Chloropyridin-3-yl)thiophene-2-sulfonylchloride (0.21 g, 1.08 mmol) was prepared as described in EXAMPLE 48, Part C from 5-chloro3-(thiophen-2-yl) pyridine.

$^1$H NMR (CDCl$_3$, 300 MHz) δ 8.88 (d, 1H), 8.66 (d, 1H), 7.94 (m, 1H), 7.65 (AB, 2H); EI MS, [M]$^+$=293, 295.

C. 5-(5-chloropyridin-3-yl)thiophene-2-sulfonic acid [1-(3-cyanobenzyl)-2-oxo-pyrrolidin-3-(S)-yl]amide The title compound (0.012 g, 0.288 mmol) is prepared as in EXAMPLE 1, Part E from 3-(3-(S)-amino-2-oxo-pyrrolidin-1-ylmethyl)benzonitrile (0.039 g, 0.153 mmol) and 6-chlorobenzo[b]thiophene-2-sulfonyl chloride (0.045 g, 0.153 mmol) in acetonitrile.

$^1$H NMR (CDCl$_3$300 MHz) δ 8.74 (d, 1H), 8.58 (d, 1H), 7.88 (dd, 1H), 7.61 (m, 1H), 7.52 (AB, 2H), 7.47 (m, 3H), 5.64 (bs, 1H), 4.47(AB, 2H) 3.97 (dd, 3H) 3.27 (m, 2H), 2.64 (m, 1H), 2.16 (m, 1H); EI MS, [M]$^+$=473, 475, Cl pattern.

D. 3-{3-(S)-[5-(5-Chloropyridin-3-yl)-thiophene-2-sulfonylamino]-2-oxopyrrolidin-1-ylmethyl}benzamidine trifluroacetate The title compound was prepared from 5-(5-chloropyridin-3-yl)thiophene-2-sulfonic acid [1-(3-cyanobenzyl)-2-oxo-pyrrolidin-3-(S)-yl]amide (0.012 g, 0.025 mmol) as described in EXAMPLE 1, Part F. The crude product is purified by RP-HPLC eluting with a gradient of 10% CH$_3$CN/H$_2$O (0.1% TFA) to 100% CH$_3$CN. The appropriate fractions are lyophilized to provide 3-{3-(S)-[5-(5-chloropyridin-3-yl)-thiophene-2-sulfonylamino[-2-oxopyrrolidin-1-ylmethyl}benzamidine trifluroacetate as a white solid (0.005 g, 0.14 mmol).

$^1$H NMR (DMSO-d$_6$, 300 MHz) δ 9.28 (bs), 8.89 (bs), 8.60 (m), 8.37 (m), 7.75 (AB), 7.67 m), 7.56 (m4.44 (AB), 4.24 (m, 2H), 3.17 (m), 2.20 (m), 1.69 (m). FAB MS, [M+H]$^+$=490, 492, Cl pattern.

EXAMPLE 55

3-[3-(S)-(4-chloro-5-pyridin-3-ylthiophene-2-sulfonylamino)-2-oxopyrrolidin-1-ylmethyl]-benzamidine trifluoroacetate

A. (3-Chlorothiophen-2-yl)pyridine 3-chlorothiophene-2-boronic acid (1.5 g, 9.24 mmol), prepared as described in EXAMPLE 48, Part A from 3-chlorothiophene was reacted with 3-bromopyridine (0.81 mL, 8.4 mmol) as described in EXAMPLE 48, Part B to give the title compound (0.232 g, 1.19 mmol).

$^1$H NMR (CDCl$_3$300 MHz) δ 8.89 (dd, 1H), 8.58 (dd, 1H), 7.98 (ddd, 1H), 7.36 (dd, 1H), 7.19 (AB, 2H).

B. 3-chloro-5-pyridin-3-ylthiophene-2-sulfonylchloride (3-chlorothiophene-2-yl)pyridine (0.232 g, 1.19 mmol) was reacted as described in EXAMPLE 48, Part C to give 3-chloro-5-(pyridin-3-yl)thiophene-2-sulfonyl chloride (0.154 g, 0.612 mmol) which is contaminated with some butylated material.

$^1$H NMR (CDCl$_3$, 300 MHz) δ 8.92 (bs, 1H), 8.87 (d, 1H), 8.05 (dd, 1H), 7.84 (s, 1H), 7.47 (dd, 1H); EI MS, [M]$^+$=293, 295, Cl pattern.

C. 4-Chloro-5-pyridin-3-ylthiophene-2-sulfonic acid [1-(3-cyanobenzyl)-2-oxo-pyrrolidin-3-(S)-yl]amide The title compound (0.063 g, 0.133 mmol) is prepared as in EXAMPLE 1, Part E from 3-(3-(S)-amino-2-oxo-pyrrolidin-1-ylmethyl)benzonitrile (0.154 g, 0.612 mmol) and 3-chloro-5-pyridin-3-ylthiophene-2-sulfonylchloride (0.180 g, 0.612 mmol) in acetonitrile.

$^1$H NMR (CDCl$_3$, 300 MHz) δ 8.86 (bs, 1H), 8.70 (dd, 1H), 7.98 (ddd, 1H), 7.42–7.55 (m, 4H), 7.56–7.66 (m,2H), 6.64 (bs, 1H), 4.50 (AB, 2H), 4.08 (dd, 3H), 3.28 M, 2H), 2.67 (m, 1H), 2.18 (m, 1H).

D. 3-[3-(S)-(4-chloro-5-pyridin-3-ylthiophene-2-sulfonylamino)-2-oxopyrrolidin-1-ylmethyl]-benzamidine trifluoroacetate The title compound was prepared from 4-chloro-5-pyridin-3-ylthiophene-2-sulfonic acid [1-(3-cyanobenzyl)-

2-oxo-pyrrolidin-3-(S)-yl]amide (0.063 g, 0.133 mmol) as described in EXAMPLE 1, Part F. The crude product is purified by RP-HPLC eluting with a gradient of 10% CH$_3$CN/H$_2$O (0.1% TFA) to 100% CH$_3$CN to give 3-[3-(S)-4-chloro-5-pyridin-3-ylthiophene-2-sulfonylamino)-2-oxopyrrolidin-1-ylmethyl]-benzamidine trifluoroacetate as a white solid (0.076 g, 0.106 mmol). $^1$H NMR (DMSO-d$_6$, 300 MHz) δ 9.32 (bs, 2H), 9.08 (bs, 2H), 8.88 (bs, 1H), 8.82 (d, 1H), 8.70 (d, 1H), 8.13 (dd, 1H), 7.87 (s, 1H), 7.72 (m,1H), 7.51 (m, 4H4.45 (AB, 2H), 4.31 (m, 1H), 3.21 (m, 2H), 2.33 (m, 1H), 1.79 (m, 1H). Ion spray MS, [M+H]$^+$= 490, 492, Cl pattern.

EXAMPLE 56

4-Hydroxy-3-[3-(S)-(6-chlorobenzo[b]thiophene-2-sulfonylamino)-2-oxo-pyrrolidin-1-ylmethyl]-benzamide trifluoroacetate A. 6-chlorobenzo[b]thiophene-2-sulfonic acid [1-(5-cyano-2-hydroxy-benzyl)-2-oxo-pyrrolidin-3-(S)-yl]-amide The title compound is prepared from 3-[(3-amino-2-oxo-pyrrolidin-1-yl)-methyl]-4-hydroxy-benzonitrile hydrochloride as described in EXAMPLE 17, Part G substituting 6-chlorobenzo[b]thiophene-2-sulfonyl chloride in place of 4,6-dichlorobenzo[b]thiophene-2-sulonyl chloride. The crude product is triturated with Et$_2$O to give the title compound as a white solid.

$^1$H NMR (CDCl$_3$) δ 8.15 (d, 1H), 7.95 (s, 1H), 7.82 (m, 2H), 7.50 (s, 1H), 7.40 (m, 2H), 6.94 (d, 1H), 4.46 (d, 1H), 4.35 (d, 1H), 4.15 (t, 1H), 3.30 (m, 2H), 2.40 (m, 1H), 1.95 (m, 1H). FAB MS, [M+H]$^+$=462, 464, Cl pattern.

B. 4-Hydroxy-3-[3-(S)-(6-chlorobenzo[b]thiophene-2-sulfonylamino)-2-oxo-pyrrolidin-1-ylmethyl]-benzamide The title compound is prepared as described in EXAMPLE 1, Part F using 6-chlorobenzo[b]thiophene-2-sulfonic acid [1-(5-cyano-2-hydroxy-benzyl)-2-oxo-pyrrolidin-3-(S)-yl]-amide as the starting material. The crude product is purified by RP-HPLC eluting with a gradient of 10% CH$_3$CN/H$_2$O (0.1% TFA) to 80% CH$_3$CN/H$_2$O (0.1% TFA). The appropriate fractions are lyophilized to provide the title compound as a white solid.

$^1$H NMR (DMSO-d$_6$, 300 MHz) δ 10.80 (bs, 1H), 9.00 (bs, 2H), 8.82 (d, 1H), 8.62 (bs, 2H), 7.98 (m, 2H), 7.90 (d, 1H), 7.47 (m, 2H), 6.65 (d, 1H), 4.49 (AB, 2H), 4.23 (m, 1H), 3.32 (m, 2H), 2.30 (m, 1H), 1.82 (m, 1H). FAB MS, [M+H]$^+$=479, 481, Cl pattern.

EXAMPLE 57

3-[3-(S)-(1-Aminoisoquinoline-6-sulfonylamino)-2-oxopyrrolidin-1-ylmethyl]-benzamidine trifluoroacetate A. 3-(3-Bromophenyl)acrylic acid 3-Bromobenzaldehyde (10.0 g, 54 mmol), malonic acid (10.1 g, 97 mmol) and piperidine (0.267 mL, 2.7 mmol) are treated with pyridine (30 mL) and treated at 100° C. for 3.5 hours. The reaction mixture is cooled to room temperature, poured into 200 ml of 20% hydrochloric acid at 0° C.; the resultant precipitate is collected, washed with copious amounts of water and dried in a vacuum dessicator overnight to afford the title compound (11.64 g, 51 mmol).

$^1$H NMR (DMSO-d$_6$, 300 MHz) δ 12.55 (bs, 1H), 7.96 (s, 1H), 7.70 (d, 1H), 7.5–7.64 (m, 2H), 7.38 (m, 1H), 6.62 (d, 1H). EI MS, M$^+$=226, 228, Br pattern.

B. 6-Bromoisoquinolin-1-one 3-(3-Bromophenyl)acrylic acid (10.0 g, 44 mmol) is subjected to methods described in EXAMPLE 23, Part B to give 5.6 g of a yellow solid. This material is washed with hot ethanol/ethyl acetate to give the title compound as a white solid (2.54 g, 11 mmol).

$^1$H NMR (DMSO-d$_6$, 300 MHz) δ 11.32 (bs, 1H), 8.05 (bs, 1H), 7.92 (s, 1H), 7.58 (d, 1H), 7.23 (m, 1H), 6.49 (d, 1H). EI MS, M$^+$=223, 225, Br pattern.

C. 6-Bromo-1-Chloroisoquinoline

6-Bromoisoquinolin-1-one (2.54 g, 11 mmol) is converted to the title compound (2.69 g, 11 mmol) by the method described in EXAMPLE 23, Part C.

$^1$H NMR (CDCl$_3$, 300 MHz) δ 8.30 (d, 1H), 8.19 (d, 1H), 8.04 (s, 1H), 7.78 (d, 1H), 7.52 (d, 1H), 7.27 (s, 1H), 6.49 (d, 1H). EI MS, M$^+$=241, 243.

D. 1-Chloroisoquinoline-2-sulfonyl chloride

6-Bromo-1-Chloroisoquinoline (2.69 g, 11 mmol) is converted to the title compound by the method described in EXAMPLE 1, Part D except that the crude product was washed with hexane to give a yellow solid (3.6 g) which was used without further purification; EI MS, M$^+$=261, 263.

E. 1-Chloroisoquinoline-6-sulfonic acid [1-(3-cyanobenzyl)-2-oxo-pyrrolidin-3-(S)-yl]amide 3-(3-(S)-amino-2-oxo-pyrrolidin-1-ylmethyl)benzonitrile hydrochloride (1.7 g, 6.8 mmol) is reacted with 1-Chloroisoquinoline-2-sulfonyl chloride (3.54 g, 13.6 mmol) as described in EXAMPLE 1, Part E. The crude product was purified by flash chromatography (2% MeOH/CH$_2$Cl$_2$) to yield the title compound (1.14 g, 2.58 mmol).

$^1$H NMR (CDCl$_3$, 300 MHz) δ8.49 (m, 2H), 8.40 (d, 1H), 8.12 (dd, 1H), 7.74 (d, 1H), 7.57 (m, 1H), 7.45 (d, 1H), 7.39 (d, 1H), 5.83 (bs, 1H), 4.44 (AB, 2H), 3.90 (dd, 1H) 3.20 (dd, 2H), 2.61 (m, 1H), 2.08 (m, 1H); FAB MS, [M+H]$^+$= 441, 443.

F. 1-Aminoisoquinoline-6-sulfonic acid [1-(3-cyanobenzyl)-2-oxo-pyrrolidin-3-(S)-yl]amide.

1-Aminoisoquinoline-6-sulfonic acid [1-(3-cyanobenzyl)-2-oxo-pyrrolidin-3-(S)-yl]amide (0.20 g, 0.45 mmol) and phenol (3 g) were heated together at 70° C. for 5 minutes treated with ammonium acetate (2.5 g) and heated to 115° C. for an additional 7 hours. The reaction is cooled to room temperature, diluted with ethyl acetate and partitioned with 1 N sodium hydroxide. The aqueous layer was saturated with sodium chloride and washed with fresh ethyl acetate (2×100 mL). the organic layers are combined, dried (sodium sulfate), concentrated and chromatographed (5% MeOH/CH$_2$Cl$_2$) to afford the title compound (0.108 g, 0.26 mmol).

$^1$H NMR (CDCl$_3$, 300 MHz) δ8.28 (s, 1H), 8.03 (d, 1H), 7.92 (AB, 2H), 7.55 (m, 1H), 7.4–7.48 (m, 3H), 7.08 (d, 1H), 5.50 (bs, 3H), 4.34 (AB,2H), 3.89 (dd, 1H) 3.22 (m, 2H), 2.58 (m, 1H), 2.09 (m, 1H); FAB MS, [M+H]$^+$=422.

G. 3-[3-(S)-(1-Aminoisoquinoline-6-sulfonylamino)-2-oxopyrrolidin-1-ylmethyl]-benzamidine bistrifluoroacetate.

1-Aminoisoquinoline-6-sulfonic acid [1-(3-cyanobenzyl)-2-oxo-pyrrolidin-3-(S)-yl]amide (0.108 g, 0.26 mmol) is treated as described in EXAMPLE 1, Part F and purified by HPLC to obtain the title compound as a white solid (0.10 g, 0.15 mmol).

$^1$H NMR (DMSO-d$_6$, 300 MHz) δ9.39 (bs, 2H), 9.21 (bs, 4H), 8.69 (d, 1H), 8.60 (d, 1H), 8.46 (d, 1H), 8.12 (dd, 1H), 7.80 (d, 1H), 7.67 (d, 1H), 7.5–7.6 (m, 3H), 7.38 (d, 1H), 4.39 (bs, 2H), 4.26 (m, 1H) 3.14 (dd, 2H), 2.18 (m, 1H), 1.67 (m, 1H); FAB MS, [M+H]$^+$=439. Elemental analysis calculated with 2 mol H$_2$O: C=42.09%, H=4.13%, N=11.78%, found: C=42.17%, H=3.90%, N=11.38%.

EXAMPLE 58
4-Fluoro-3-[3-(S)-(5-pyridin-3-yl-thiophene-2-sulfonylamino)-2-oxo-pyrrolidin-1-ylmethyl]-benzamide trifluoroacetate.

A. 5-Bromo-2-fluoro-benzyl alcohol.

To a solution of 5-bromo-2-fluoro-benzaldehyde (6.10 g, 30.0 mmol) in 30 mL of THF at 0° C. is added 5 mL of sodium borohydride (2.0 M solution in triglyme, 10.0 mmol). The reaction mixture is stirred at 0° C. for 25 minutes and then quenched by the addition of 1 N HCl. The mixture is diluted with EtOAc and the layers are separated. The organic layer is washed with H$_2$O and saturated NaCl. The organic layer is dried over MgSO$_4$, filtered and concentrated. The crude product is purified by column chromatography eluting with 15% EtOAc/hexanes to afford the title compound (6.00 g, 29.3 mmol).

$^1$H NMR (CDCl$_3$, 300 MHz) δ7.55 (dd, 1H), 7.36 (m, 1H), 6.89 (t, 1H), 4.71 (d, 2H), 2.11 (bs, 1H). EI MS, [M]$^+$=204, 206, Br pattern.

B. 5-Bromo-2-fluoro-benzyl bromide.

To a solution of 5-bromo-2-fluoro-benzyl alcohol (3.10 g, 15.1 mmol) in 30 mL of THF at 10° C. is added triphenyl phosphine (4.10 g, 15.6 mmol) followed by N-bromosuccinimide (2.67 g, 15.0 mmol). The ice bath is removed and the resulting solution is stirred for 20 minutes at room temperature. The crude product is purified by column chromatography eluting with 5% EtOAc/hexanes to give the title compound (3.90 g, 14.5 mmol).

$^1$H NMR (CDCl$_3$, 300 MHz) δ7.50 (dd, 1H), 7.37 (m, 1H), 6.92 (t, 1H), 4.42 (s, 2H). EI MS, [M]$^+$=266, 268, 270; 2 Br pattern.

C. 3-(S)-(tert-Butoxy-carbonyl-amino)-1-(5-bromo-2-fluoro-benzyl)-pyrrolidin-2-one.

The title compound is prepared as described in EXAMPLE 1, Part B substituting 5-bromo-2-fluoro-benzyl bromide for α-bromo-m-toluoyl nitrile. The crude material is purified by column chromatography eluting with 3:1:1 EtOAc:hexane:CH$_2$Cl$_2$.

$^1$H NMR (CDCl$_3$, 300 MHz) δ7.40 (m, 2H), 6.96 (t, 1H), 5.20 (bs, 1H), 4.50 (s, 2H), 4.18 (m, 1H), 3.28 (m, 2H), 2.64 (m, 1H), 1.90 (m, 1H), 1.45 (s, 9H). EI MS [M]$^+$=387, 389, Br pattern.

D. 3-(S)-(tert-Butoxy-carbonyl-amino)-1-(5-cyano-2-fluoro-benzyl)-pyrrolidin-2-one.

The title compound is prepared as described in EXAMPLE 3, Part C substituting 3-(S)-(tert-butoxy-carbonyl-amino)-1-(5-bromo-2-fluoro-benzyl)-pyrrolidin-2-one for (5-iodo-thiophen-3-yl)methanol. The crude material is purified by column chromatography eluting with 3:1:1 EtOAc:hexane:CH$_2$Cl$_2$.

$^1$H NMR (CDCl$_3$, 300 MHz) δ7.70 (bd, 1H), 7.61 (m, 1H), 7.19 (t, 1H), 5.18 (bs, 1H), 4.63 (d, 1H), 4.50 (d, 1H), 4.18 (m, 1H), 3.32 (m, 2H), 2.64 (m, 1H), 2.00 (m, 1H), 1.47 (s, 9H). EI MS, [M]$^+$=334.

E. 3-(S)-[(3-Amino-2-oxo-pyrrolidin-1-yl)-methyl]-4-fluoro-benzonitrile hydrochloride.

The title compound is prepared as described in Example 1, Part C substituting 3-(S)-(tert-butoxy-carbonyl-amino)-1-(5-cyano-2-fluoro-benzyl)-pyrrolidin-2-one for [1-(3-cyanobenzyl)-2-oxo-pyrrolidin-3-(S)-yl]-carbamic acid tert-butyl ester. The title compound is obtained as a white solid.

$^1$H NMR (DMSO-d$_6$, 300 MHz) δ8.73 (bs, 3H), 7.92 (m, 1H), 7.86 (d, 1H), 7.50 (t, 1H), 4.54 (s, 2H). 4.10 (m, 1H), 3.38 (m, 2H), 2.42 (m, 1H), 2.07 (m, 1H). EI MS, [M]$^+$=233.

F. 5-Pyridin-3-yl-thiophene-2-sulfonic acid [1-(5-cyano-2-fluoro-benzyl)-2-oxo-pyrrolidin-3-(S)-yl]-amide.

The title compound is prepared from 3-(S)-[(3-amino-2-oxo-pyrrolidin-1-yl)-methyl]-4-fluoro-benzonitrile hydrochloride as described in EXAMPLE 17, Part G substituting 5-pyridin-3-yl-thiophene-2-sulfonyl chloride in place of 4,6-dichlorobenzo[b]thiophene-2-sulfonyl chloride. The crude product is triturated with Et$_2$O to give the title compound as a white solid $^1$H NMR (CDCl$_3$+CD$_3$OD; 300 MHz) δ8.87 (s, 1H), 8.55 (d, 1H), 8.08 (d, 1H), 7.73 (m, 3H), 7.53 (m, 1H), 7.48 (d, 1H), 7.28 (t, 1H), 4.54 (AB, 2H), 4.20 (m, 1H), 3.34 (m, 2H), 2.49 (m, 1H), 1.98 (m, 1H). FAB MS, [M+H]$^+$=457.

G. 4-Fluoro-3-[3-(S)-(5-pyridin-3-yl-thiophene-2-sulfonylamino)-2-oxo-pyrrolidin-1-ylmethyl]-benzamide trifluoroacetate.

The title compound is prepared as described in EXAMPLE 1, Part F using 5-pyridin-3-yl-thiophene-2-sulfonic acid [1-(5-cyano-2-fluoro-benzyl)-2-oxo-pyrrolidin-3-(S)-yl]-amide as the starting material. The crude product is purified by RP-HPLC eluting with a gradient of 10% CH$_3$CN/H$_2$O (0.1% TFA) to 80% CH$_3$CN/H$_2$O (0.1% TFA). The appropriate fractions are lyophilized to provide the title compound as a white solid.

$^1$H NMR (CD$_3$OD, 300 MHz) δ8.77 (s, 1H), 8.44 (d, 1H), 8.03 (d, 1H), 7.67 (m, 2H), 7.58 (d, 1H), 7.45 (d, 1H), 7.41 (m, 1H), 7.28 (t, 1H), 5.10 (s, 1H), 4.47 (s, 2H), 4.13 (m, 1H), 3.23 (m, 2H), 2.28 (m, 1H), 1.81 (m, 1H). FAB MS, [M+H]$^+$=473.

EXAMPLE 59
2-Chloroquinoline-6-sulfonic acid {1-[3-(aminoiminomethyl)-benzyl]-2-oxo-pyrrolidin-3-(S)-yl}-amide trifluoroacetate.

A. 2-Chloro-6-bromoquinoline.

The title compound is prepared from 4-bromoaniline and cinnamoyl chloride according to the procedure described in J. Chem. Soc., Perkin Trans. I, 1972, 1648. The crude 6-bromo-1H-quinolin-2-one intermediate obtained is triturated in Et$_2$O/hexanes and filtered to give a beige solid which is used directly in the chlorination step. The crude product is recrystallized in MeOH to afford the title compound as a beige solid.

$^1$H NMR (CDCl$_3$, 300 MHz) δ8.01 (d, 1H), 7.98 (s, 1H), 7.89 (m, 1H), 7.80 (m, 1H), 7.40 (d, 1H).

B. 2-Chloroquinoline-6-sulfonyl chloride.

The title compound is prepared as described in EXAMPLE 1, Part D using 2-chloro-6-bromoquinoline in place of thianaphthalene. The crude product is triturated with hexanes to give a beige solid and is of sufficient purity to be used in the subsequent step.

$^1$H NMR (CDCl$_3$, 300 MHz) δ8.60 (s, 1H), 8.31 (d, 1H), 8.28 (m, 2H), 7.60 (d, 1H).

C. 2-Chloroquinoline-6-sulfonic acid [1-(3-cyanobenzyl)-2-oxopyrrolidin-3-(S)-yl]-amide.

The title compound is prepared from 3-(3-(S)-amino-2-oxo-pyrrolidin-1-ylmethyl)-benzonitrile hydrochloride as described in EXAMPLE 1, Part E using 2-chloroquinoline-6-sulfonyl chloride in place of benzo[b]thiophene-2-sulfonyl chloride. The product is obtained as a white solid.

$^1$H NMR (CDCl$_3$, 300 MHz) δ8.50 (s, 1H), 8.25 (d, 1H), 8.18 (m, 1H), 8.14 (m, 1H), 7.58 (m, 1H), 7.52 (d, 1H), 7.44

(m, 3H), 5.68 (bs, 1H), 4.45 (AB, 2H), 3.89 (m, 1H), 3.22 (m, 2H), 2.63 (m, 1H), 2.08 (m, 1H).

D. 2-Chloroquinoline-6-sulfonic acid {1-[3-(aminoiminomethyl)-benzyl]-2-oxopyrrolidin-3-(S)-yl}amide trifluoroacetate.

2-Chloroquinoline-6-sulfonic acid [1-(3-cyanobenzyl)-2-oxopyrrolidin-3-(S)-yl]-amide is converted to the title compound as described in EXAMPLE 1, Part F. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.29 (bs, 2H), 9.13 (bs, 2H), 8.68 (d, 1H), 8.64 (s, 1H), 8.46 (d, 1H), 8.19 (m, 1H), 8.13 (m, 1H), 7.75 (d, 1H), 7.66 (m, 1H), 7.55 (m, 3H), 4.42 (AB, 2H), 4.21 (m, 1H), 3.10 (m, 2H), 2.07 (m, 1H), 1.62 (m, 1H). IS MS, [M+H]$^+$=458, 460, Cl pattern. Elemental analysis calculated with 1.5 mol $H_2O$, cal C=45.83%, H=3.45%, N=11.13% found: C=45.53%, H=3.49%, N=10.79%.

EXAMPLE 60
2-Aminoquinoline-6-sulfonic acid {1-[3-(aminoiminomethyl)-benzyl]-2-oxo-pyrrolidin-3-(S)-yl}-amide bistrifluoroacetate.

2-Chloroquinoline-6-sulfonic acid {1-[3-(aminoiminomethyl)-benzyl]-2-oxopyrrolidin-3-(S)-yl}amide trifluoroacetate (0.25 g, 0.50 mmol) and phenol (0.80 g, 8.25 mmol) are melted together at 80° C. for 5 minutes. To the mixture is added ammonium acetate (0.64 g, 8.25 mmol) and heating is continued at 120° C. for 2.5 hours. At this time, more $NH_4OAc$ (s) is added. After 1 hour, the reaction mixture is cooled to room temperature and partitioned between EtOAc and 0.5 N HCl. The layers are separated and the aqueous phase is extracted with EtOAc. The aqueous layer is concentrated in vacuo to a small volume (~5 mL). The solution of crude product is purified by RP-HPLC eluting in a gradient of 10% $CH_3CH/H_2O$ (0.1% TFA) to 40% $CH_3CN/H_2O$ (0.1% TFA) and the appropriate product fractions are lyophilized to provide the title compound as a white solid.

$^1$H NMR (DMSO-$d_6$, 300 MHz) δ9.29 (bs, 2H), 9.21 (bs, 2H), 9.03 (bs, 2H), 8.46 (d, 1H), 8.44 (s, 1H), 8.37 (d, 1H), 8.13 (d, 1H), 7.75 (d, 1H), 7.68 (m, 1H), 7.56 (m, 3H), 7.15 (d, 1H), 4.40 (s, 2H), 4.16 (m, 1H), 3.10 (m, 2H), 2.07 (m, 1H), 1.62 (m, 1H). IS MS, [M+H]$^+$=439. Elemental analysis calculated with 2.4 mol $H_2O$, 2.7 mol $CF_3CO_2H$, Cal. C=42.48%, H=3.34%, N=11.26% found: C=42.33%, H=3.69%, N=11.39%.

EXAMPLE 61
4-Hydroxy-3-[3-(S)-(7-chloro-thieno[2,3-c]pyridine-2-sulfonylamino)-2-oxo-pyrrolidin-1-ylmethyl]-benzamidine trifluoroacetate.

A. 6H-Thieno[2,3-c]pyridin-7-one.

To a solution of 3-thiophen-3-yl-acrylic acid (15.5 g, 100.5 mmol) in 400 mL of acetone is added triethylamine (12.0 g, 110.6 mmol). The resulting solution is cooled to 0° C. and ethyl chloroformate (11.2 g, 110.6 mmol) is added dropwise. After 2 hours, sodium azide (9.8 g, 150.8 mmol) in 100 mL of $H_2O$ is then added. The solution is stirred for 1.5 hours at 0° C. After this time, the solution is poured into 1000 mL of $H_2O$. A white precipitate forms which is collected by filtration. The resulting solid is dried over $P_2O_5$ under vacuum. The solid is suspended in 20 mL of diphenyl ether. This solution is added dropwise to a solution of tributylamine (18.6 g, 100.5 mmol) in 200 ml of diphenyl ether at 190° C. After 2 hours, the solution is cooled to ambient temperatures. The solution is diluted with 1000 mL of hexanes and is cooled to 0° C. The resulting solid is collected by filtration and the solid is washed with hexanes. The title compound (10.9 g, 72.1 mmol) is obtained as a white solid.

$^1$H NMR (DMSO-$d_6$, 300 MHz) δ11.4 (bs, 1H), 7.54 (d, 1H), 7.42 (d, 1H), 7.22 (d, 1H), 6.84 (d, 1H).

C. 7-Chloro-thieno[2,3-c]pyridine.

6H-Thieno[2,3-c]pyridin-7-one (2.3 g, 15.22 mmol) is dissolved in 50 mL of phosphorous oxy chloride. The solution is heated to 100° C. After 4 hours, the solution is concentrated. The residue is dissolved in $CH_2Cl_2$. The resulting solution is washed with water and saturated NaCl. The organic layer is dried over $MgSO_4$, filtered and concentrated. The crude product is purified by column chromatography eluting with a gradient of 40% $CH_2Cl_2$/hexanes to 60% $CH_2Cl_2$/hexanes. The title compound (2.0 g, 12.2 mmol) is obtained as a white solid.

$^1$H NMR (CDCl$_3$, 300 MHz) δ8.26 (d, 1H), 7.76 (d, 1H), 7.62 (d, 1H), 7.41 (d, 1H). EI MS, [M]$^+$=169, 171, Cl pattern.

D. 7-Chloro-thieno[2,3-c]pyridine-2-sulfonyl chloride.

The title compound is prepared as described in EXAMPLE 1, Part D substituting the 7-chloro-thieno[2,3-c]pyridine for thianaphthalene. The crude product is purified by column chromatography eluting with a gradient of 40% $CH_2Cl_2$/hexanes to 60% $CH_2Cl_2$/hexanes. The title compound is obtained as a white solid.

$^1$H NMR (CDCl$_3$, 300 MHz) δ8.48 (d, 1H), 8.18 (s, 1H), 7.77 (d, 1H).

E. 4-Hydroxy-3-[3-(S)-(7-chloro-thieno[2,3-c]pyridine-2-sulfonylamino)-2-oxo-pyrrolidin-1-ylmethyl]-benzamidine trifluoroacetate.

The title compound is prepared as described in EXAMPLE 17, Part G, substituting 7-chloro-thieno[2,3-c] pyridine-2-sulfonyl chloride for 4,6-dichlorobenzo[b] thiophene-2-sulfonyl chloride. The crude product is then treated as described in EXAMPLE 1, Part F using 7-chlorobenzo[b]thiophene-2-sulfonic acid [1-(3-cyanobenzyl)-2-oxo-pyrrolidin-3-(S)-yl]-amide as the starting material. The crude product is purified by RP-HPLC eluting with a gradient of 10% $CH_3CN/H_2O$ (0.1% TFA) to 70% $CH_3CN/H_2O$ (0.1% TFA). The appropriate fractions are lyophilized to provide the title compound as a white solid.

$^1$H NMR (DMSO-$d_6$, 300 MHz) δ10.89 (bs, 1H), 9.03 (bs, 3H), 8.68 (bs, 2H), 8.40 (d, 1H), 8.18 (s, 1H), 8.00 (d, 1H), 7.56 (d, 1H), 7.33 (s, 1H), 6.95 (d, 1H), 4.38 (m, 3H), 3.18 (m, 2H), 2.21 (m, 1H), 1.72 (m, 1H). FAB MS, [M+H]$^+$=480, 482, Cl pattern.

EXAMPLE 62
4-Hydroxy-3-[3-(S)-(thieno[2,3-c]pyridine-2-sulfonylamino)-2-oxo-pyrrolidin-1-ylmethyl]-benzamidine bistrifluoroacetate.

A. 4-Hydroxy-3-[3-(S)-(thieno[2,3-c]pyridine-2-sulfonylamino)-2-oxo-pyrrolidin-1-ylmethyl]-benzamidine bistrifluoroacetate.

To a solution of 4-hydroxy-3-[3-(S)-(7-chloro-thieno[2,3-c]pyridine-2-sulfonylamino)-2-oxo-pyrrolidin-1-ylmethyl]-benzamidine trifluoroacetate (0.26 g, 0.54 mmol) in 15 mL of methanol is added KOH (0.07 g, 1.54 mmol) and 10% by weight Pd/C (0.05 g). The atmosphere above the reaction mixture is replaced by hydrogen and the solution is heated to 50° C. After 24 hours, the solution is cooled to ambient temperatures and filtered through a pad of Celite. The Celite is washed with methanol. The collected solution is concentrated. The crude material is purified by RP-HPLC eluting with a gradient of 10% $CH_3CN/H_2O$ (0.1% TFA) to 40%

CH₃CN/H₂O (0.1% TFA). The appropriate fractions are lyophilized to provide the title compound as a white solid.

$^1$H NMR (DMSO-d$_6$, 300 MHz) δ10.89 (bs, 1H), 9.38 (bs, 2H), 8.96 (bs, 2H), 8.88 (d, 1H), 8.70 (m, 2H), 8.58 (m, 1H), 8.12 (s, 1H), 7.98 (d, 1H), 7.58 (d, 1H), 7.38 (s, 1H), 6.95 (d, 1H), 4.28 (AB, 2H), 4.20 (m, 1H), 3.18 (m, 2H), 2.21 (m, 1H), 1.72 (m, 1H). FAB MS, [M+H]$^+$=446.

EXAMPLE 63

4-Hydroxy-3-[3-(S)-(thieno[3,2-c]pyridine-2-sulfonylamino)-2-oxo-pyrrolidin-1-ylmethyl]-benzamidine trifluoroacetate.

4-Hydroxy-3-[3-(S)-(thieno[3,2-c]pyridine-2-sulfonylamino)-2-oxo-pyrrolidin-1-ylmethyl]-benzamidine trifluoroacetate.

The title compound is prepared as described in EXAMPLE 62, Part A, substituting 4-hydroxy-3-[3-(S)-(4-chloro-thieno[3,2-c]pyridine-2-sulfonylamino)-2-oxo-pyrrolidin-1-ylmethyl]-benzamidine trifluoroacetate for 4-hydroxy-3-[3-(S)-(7-chloro-thieno[2,3-c]pyridine-2-sulfonylamino)-2-oxo-pyrrolidin-1-ylmethyl]-benzamidine trifluoroacetate. The crude material is purified by RP-HPLC eluting with a gradient of 10% CH₃CN/H₂O (0.1% TFA) to 40% CH₃CN/H₂O (0.1% TFA). The appropriate fractions are lyophilized to provide the title compound as a white solid.

$^1$H NMR (DMSO-d$_6$, 300 MHz) δ11.00 (bs, 1H), 9.35 (bs, 2H), 8.96 (m, 2H), 8.77 (d, 1H), 8.70 (bs, 2H), 8.28 (s, 1H), 8.21 (s, 1H), 7.58 (d, 1H), 7.30 (s, 1H), 6.92 (d, 1H), 4.24 (AB, 2H), 4.16 (m, 1H), 3.12 (m, 2H). 2.18 (m, 1H), 1.72 (m, 1H). FAB MS, [M+H]$^+$=446.

EXAMPLE 64

4-[3-(6-Fluorobenzo[b]thiophene-2-sulfonylamino)-2-oxo-pyrrolidin-1-ylmethyl]-thiophene-2-carboxamidine hydrochloride A. 6-Fluorobenzo[b]thiophene-2-sulfonic acid [1-(5-cyanothiophen-3-ylmethyl)-2-oxo-pyrrolidin-3-(S)-yl]-amide.

The title compound is prepared as described in EXAMPLE 1, Part E, substituting 4-(3-(S)-amino-2-oxo-pyrrolidin-1-ylmethyl)-thiophene-2-carbonitrile hydrochloride for 3-(3-(S)-amino-2-oxo-pyrrolidin-1-ylmethyl)-benzonitrile hydrochloride and substituting 6-fluorobenzo[b]thiophene sulfonyl chloride for benzo[b]thiophene sulfonyl chloride.

$^1$H NMR (DMSO-d$_6$, 300 MHz) δ8.58 (d, 1H), 8.02 (m, 3H), 7.82 (s, 1H), 7.79 (s, 1H), 7.38 (m, 1H), 4.36 (s, 2H), 4.19 (m, 1H), 3.11 (m, 2H), 2.12 (m, 1H), 1.62 (m, 1H).

B. 4-[3-(6-Fluorobenzo[b]thiophene-2-sulfonylamino)-2-oxo-pyrrolidin-1-ylmethyl]-thiophene-2-carboxamidine hydrochloride The title compound is prepared as described in EXAMPLE 1, Part F using 6-fluorobenzo[b]thiophene-2-sulfonic acid [1-(5-cyanothiophen-3-ylmethyl)-2-oxo-pyrrolidin-3-(S)-yl]-amide as the starting material. The crude product is purified by RP-HPLC eluting with a gradient of 10% CH₃CN/H₂O to 70% CH₃CN/H₂O. The appropriate fractions are lyophilized to provide the title compound as a white solid.

$^1$H NMR (DMSO-d$_6$, 300 MHz) δ9.34 (bs, 2H), 9.03 (bs, 2H), 8.68 (s, 1H), 8.03 (m, 3H), 7.88 (s, 1H), 7.36 (m, 1H), 4.38 (AB, 2H), 4.17 (m, 1H), 3.16 (m, 2H), 2.17 (m, 1H), 1.71 (m, 1H). FAB MS, [M+H]$^+$=453.

EXAMPLE 65

4-{3-(S)-[(3-Aminopropyl)-(6-fluorobenzo[b]thiophene-2-sulfonylamino)]-2-oxo-pyrrolidin-1-ylmethyl}-thiophene-2-carboxamidine bistrifluoroacetate.

A. 4-{3-(S)-[(3-Aminopropyl)-(6-fluorobenzo[b]thiophene-2-sulfonylamino)]-2-oxo-pyrrolidin-1-ylmethyl}-thiophene-2-carboxamidine bistrifluoroacetate.

To a solution of 6-fluorobenzo[b]thiophene-2-sulfonic acid [1-(5-cyanothiophen-3-ylmethyl)-2-oxo-pyrrolidin-3-(S)-yl]-amide (0.50 g, 1.15 mmol); prepared as described in EXAMPLE 62, Part A; in 6 mL of DMF, is added K₂CO₃ (0.80 g, 5.75 mmol). The solution is cooled to 0° C. and 3-iodopropyl azide (0.36 g, 1.173 mmol) is added. The solution is stirred for 16 hours. After this time, the solution is diluted with EtOAc. The organic layer is washed with water and saturated NaCl. The organic layer is dried over MgSO₄, filtered and concentrated. The resulting residue is dissolved in ethanol. The solution is saturated with HCl (g). The solution is stirred for 16 hours. After this time, the solution is concentrated. The residue is dissolved in MeOH. The solution is saturated with NH₃ (g) and heated to 50° C. for 3 hours. After this time, the solution is concentrated. The crude material is purified by RP-HPLC eluting with a gradient of 10% CH₃CN/H₂O (0.1% TFA) to 80% CH₃CN/H₂O (0.1% TFA). The resulting product is dissolved in 8 mL of MeOH. To the solution is added 10% by weight Pd/C (0.1 g). The atmosphere above the reaction is replaced by hydrogen. After 24 hours, the solution is filtered through a pad of Celite. The Celite is washed with MeOH. The collected solution is concentrated. The crude material is purified by RP-HPLC eluting with a gradient of 10% CH₃CN/H₂O (0.1% TFA) to 80% CH₃CN/H₂O (0.1% TFA).

$^1$H NMR (DMSO-d$_6$, 300 MHz) δ9.21 (bs, 2H), 9.07 (bs, 2H), 8.12 (s, 1H), 8.03 (m, 2H), 7.90 (s, 1H), 7.81 (m, 1H), 7.68 (bs, 2H), 7.37 (m, 1H), 4.76 (m, 1H), 4.38 (AB, 2H), 3.17 (m, 2H), 2.79 (m, 2H), 2.09 (m, 1H), 1.86 (m, 3H). FAB MS, [M+H]$^+$=510.

EXAMPLE 66

[[1-(5-Carbamimidoyl-thiophen-3-ylmethyl-2-oxo-pyrrolidin-3-yl]-(6-fluorobenzo[b]thiophen-2-sulfonyl)-amino]-acetic acid trifluoroacetate.

A. [[1-(5-Cyano-thiophen-3-ylmethyl-2-oxo-pyrrolidin-3-yl]-(6-fluorobenzo[b]thiophen-2-sulfonyl)-amino]-acetic acid t-butyl ester.

To a solution of 6-fluorobenzo[b]thiophene-2-sulfonic acid [1-(5-cyanothiophen-3-ylmethyl)-2-oxo-pyrrolidin-3-(S)-yl]-amide (0.58 g, 1.33 mmol); prepared as described in EXAMPLE 62, Part A; in 10 mL of DMF, is added K₂CO₃ (0.37 g, 2.68 mmol). The solution is cooled to 0° C. and t-butyl bromoacetate (0.4 g, 2.68 mmol) is added. The solution is stirred for 4 hours. After this time, the solution is diluted with EtOAc. The organic layer is washed with water and saturated NaCl. The organic layer is dried over MgSO₄, filtered and concentrated to give the product as a white solid (0.71 g, 1.3 mmol).

$^1$H NMR (CDCl₃, 300 MHz) δ8.02 (s, 1H), 7.83 (m, 1H), 7.54 (m, 1H), 7.48 (m, 1H), 7.20 (m, 2H), 4.57 (m, 1H), 4.40 (AB, 2H), 4.00 (AB, 2H), 3.27 (m, 2H), 2.59 (m, 1H), 2.44 (m, 2H). 1.42 (s, 9H).

B. [[1-(5-Carbamimidoyl-thiophen-3-ylmethyl-2-oxo-pyrrolidin-3-yl]-(6-fluorobenzo[b]thiophen-2-sulfonyl)-amino]-acetic acid t-butyl ester trifluoroacetate.

To a solution of [[1-(5-cyano-thiophen-3-ylmethyl-2-oxo-pyrrolidin-3-yl]-(6-fluorobenzo[b]thiophen-2-sulfonyl)-amino]-acetic acid t-butyl ester (0.7 g, 1.3 mmol), in 10 mL of pyridine is added 1.0 mL of triethyl amine. The resulting solution is saturated with H₂S. After 16 hours, the solution is concentrated. The residue is dissolved in 30 mL of acetone. To the solution is added methyl iodide (1.7 mL, 26 mmol). The solution is heated to reflux for 3 hours. After this time, the solution is concentrated. The residue is dissolved in 10 mL of MeOH and ammonium acetate (0.5 g, 6.5 mmol) is added. The solution is heated to reflux. After 3 hours, the solution is concentrated to give the product as a yellowish solid. FAB MS, [M+H]$^+$=557.

C. [[1-(5-Carbamimidoyl-thiophen-3-ylmethyl-2-oxo-pyrrolidin-3-yl]-(6-fluorobenzo[b]thiophen-2-sulfonyl)-amino]-acetic acid trifluoroacetate.

[[1-(5-Carbamimidoyl-thiophen-3-ylmethyl-2-oxo-pyrrolidin-3-yl]-(6-fluorobenzo[b]thiophen-2-sulfonyl)-amino]-acetic acid t-butyl ester trifluoroacetate was dissolved in 12 mL of $CH_2Cl_2$. To the solution is added 3 mL of trifluoroacetic acid. After 3 hours, the solution is concentrated. The crude material is purified by RP-HPLC eluting with a gradient of 10% $CH_3CN/H_2O$ (0.1% TFA) to 60% $CH_3CN/H_2O$ (0.1% TFA).

$^1$H NMR (DMSO-$_6$, 300 MHz) δ9.21 (bs, 2H), 9.10 (bs, 2H), 8.14 (s, 1H), 8.01 (m, 2H), 7.88 (s, 1H), 7.78 (s, 1H), 7.37 (m, 1H), 4.78 (m, 1H), 4.38 (AB, 2H), 3.98 (AB, 2H), 3.19 (m, 2H), 2.24 (m, 1H), 2.11 (m, 1H). FAB MS [M+H]$^+$=511.

EXAMPLE 67

[Imino-(4-{3-[(7-methoxynaphthalene-2-sulfonyl)-pyridin-2-ylmethyl-amino]-2-oxo-pyrrolidin-1-ylmethyl}-thiophen-2-yl)-methyl]-carbamic acid ethyl ester.

A. 7-Methoxy-naphthalene-2-sulfonic acid [1-(5-cyanothiophen-3-ylmethyl)-2-oxo-pyrrolidin-3-(S)-yl]-amide.

The title compound is prepared as described in EXAMPLE 1, Part E, substituting 4-(3-(S)-amino-2-oxo-pyrrolidin-1-ylmethyl)-thiophene-2-carbonitrile hydrochloride for 3-(3-(S)-amino-2-oxo-pyrrolidin-1-ylmethyl)-benzonitrile hydrochloride and substituting 7-methoxy-naphthalene sulfonyl chloride for benzo[b]thiophene sulfonyl chloride. FAB MS, [M+H]$^+$=442.

B. 7-methoxynaphthalene-2-sulfonic acid [1-(5-cyanothiophen-3-ylmethyl)-2-oxo-pyrrolidin-3-(S)-yl]-pyridin-2-ylmethyl amide.

To a solution of 7-methoxy-naphthalene-2-sulfonic acid [1-(5-cyanothiophen-3-ylmethyl)-2-oxo-pyrrolidin-3-(S)-yl]-amide (0.5 g, 1.13 mmol) in 5 mL of DMF is added $K_2CO_3$ (0.78 g, 5.65 mmol). To the solution is added 2-picolyl chloride (0.23 g, 1.41 mmol). After 16 hours, the solution is diluted with EtOAc. The organic solution is washed with water and saturated NaCl. The organic layer is dried over $MgSO_4$, filtered and concentrated.

$^1$H NMR (CDCl$_3$, 300 MHz) δ8.44 (m, 2H), 7.98 (m, 2H), 7.76 (d, 1H), 7.69 (m, 2H), 7.48 (m, 2H), 7.21 (m, 2H), 4.72 (m, 1H), 4.50 (AB, 2H), 4.28 (AB, 2H), 3.16 (m, 2H), 2.24 (m, 1H), 2.00 (1H).

C. [Imino-(4-{3-[(7-methoxynaphthalene-2-sulfonyl)-pyridin-2-ylmethyl-amino]-2-oxo-pyrrolidin-1-ylmethyl}-thiophen-2-yl)-methyl]-carbamic acid ethyl ester.

The title compound is prepared as described in EXAMPLE 1, Part F using 7-methoxynaphthalene-2-sulfonic acid [1-(5-cyanothiophen-3-ylmethyl)-2-oxo-pyrrolidin-3-(S)-yl]-pyridin-2-ylmethyl amide as the starting material. The crude product is purified by RP-HPLC eluting with a gradient of 10% $CH_3CN/H_2O$ to 60% $CH_3CN/H_2O$. The appropriate fractions are lyophilized to provide the title compound as a white solid. The resulting solid (0.80 g, 1.04 mmol), is dissolved in 10 mL of $CH_2Cl_2$:DMF (10:1). To the solution is added N-methylpiperdine (0.46 g, 4.68 mmol), and ethyl chloroformate (0.11 g, 1.04 mmol). The reaction mixture is stirred for 16 hours. After this time, the solution is diluted with $CH_2Cl_2$. The organic solution is washed with $H_2O$. The organic layer is dried over $MgSO_4$, filtered and concentrated. The crude product is purified by RP-HPLC eluting with a gradient of 10% $CH_3CN/H_2O$ to 80% $CH_3CN/H_2O$. The appropriate fractions are lyophilized to provide the title compound as a white solid.

$^1$H NMR (DMSO-d$_6$, 300 MHz) δ9.5 (bs, 4H), 9.03 (bs, 2H), 8.48 (d, 1H), 8.41 (s, 1H), 8.03 (d, 1H), 7.93 (d, 1H), 7.86 (m, 1H), 7.77 (m, 4H), 7.66 (s, 1H), 7.52 (s, 1H), 7.32 (m, 1H), 4.90 (m, 1H), 4.42 (AB, 2H), 4.42 (AB, 2H), 4.10 (q, 2H), 3.90 (s, 3H), 3.12 (m, 2H), 2.12 (m, 1H), 1.78 (m, 1H), 1.18 (t, 3H). FAB MS [M+H]$^+$=622.

EXAMPLE 68

4-Amino-3-{3-(S)-[(7-methoxy-naphthalene-2-sulfonyl)-pyridine-2-ylmethyl-amino]-2-oxo-pyrrolidin-1-ylmethyl}-benzamidine trifluoroacetate.

A. 4-Amino-3-methylbenzonitrile.

To a solution of 3-methyl-4-nitrobenzonitrile (2 g, 12.3 mmol) in 100 mL of EtOH is added $SnCl_2$ (13.9 g, 61.7 mmol). The resulting solution is refluxed. After 2 hours, the solution is cooled to ambient temperatures. The solution is poured into 150 mL of ice water. The pH of the solution is adjusted to >7 with a solution of saturated $NaHCO_3$. The solution is diluted with EtOAc and the resulting mixture is filtered through Celite. The filtered solution is separated. The organic layer is dried over $MgSO_4$, filtered and concentrated to give the title compound (1.57 g, 8.7 mmol) as an off-white solid.

$^1$H NMR (CDCl$_3$, 300 MHz) δ7.30 (m, 2H), 6.63 (d, 1H), 4.10 (bs, 2H), 2.15 (m, 2H). EI MS, [M]$^+$=132.

B. 4-(Benzhydrylidenylamino)-3-methylbenzonitrile.

To a solution of 4-amino-3-methylbenzonitrile (1.2 g, 9.08 mmol) in 75 mL of toluene is added benzophenone (1.74 g, 9.53 mmol) and p-toluensulfonic acid (0.43 g, 2.1 mmol). The reaction vessel is fitted with a Dean-Stark trap and the solution is heated to reflux. After 24 hours, the solution is cooled to ambient temperatures. The solution is concentrated. The crude material is purified by column chromatography eluting with a gradient of 3% EtOAc/hexanes to 10% EtOAc/hexanes. The title compound (2.43 g, 8.2 mmol) is obtained as an oil.

$^1$H NMR (CDCl$_3$, 300 MHz) δ7.80 (m, 2H), 7.40 (m, 6H), 7.30 (s, 1H), 7.15 (d, 1H), 7.05 (bs, 2H), 6.50 (d, 1H), 2.20 (s, 3H). EI MS, [M]$^+$=296.

C. 4-(Benzhydrylidenylamino)-3-bromomethylbenzonitrile.

To a solution of 4-(benzhydrylidenylamino)-3-methylbenzonitrile (1.36 g, 4.27 mmol) in 40 mL of $CCl_4$ is added N-bromosuccinimide (0.84 g, 4.7 mmol) and benzoyl peroxide (0.22 g, 0.64 mmol). The solution is refluxed for 16 hours. The solution is cooled to ambient temperatures. The solution is diluted with $CH_2Cl_2$. The solution is washed with 1 N NaOH and saturated NaCl. The organic layer is dried over $MgSO_4$, filtered and concentrated. The crude material is purified by column chromatography eluting with a gradient of 5% EtOAc/hexanes to 10% EtOAc/hexanes. The title compound (0.91 g, 2.43 mmol) is obtained as an oil.

$^1$H NMR (CDCl$_3$, 300 MHz) δ7.80 (m, 2H), 7.60 (d, 1H), 7.35 (m, 8H), 7.15 (dd, 1H), 6.35 (d, 1H), 4.55 (s, 2H). EI MS, [M]$^+$=374.

D. {1-[2-(Benzhydrylidenylamino)-5-cyano-benzyl]-2-oxopyrrolidin-3-yl}-carbamic acid tert-butyl ester.

The title compound is prepared as described in EXAMPLE 1, Part B substituting 4-(benzhydrylidenylamino)-3-bromomethylbenzonitrile for α-bromo-m-toluyl nitrile. The crude material is purified by column chromatography eluting with a gradient of 30% EtOAc/hexanes to 40% EtOAc/hexanes. The title compound is obtained as a yellow solid.

$^1$H NMR (CDCl$_3$, 300 MHz) δ7.70 (bs, 2H), 7.40 (s, 1H), 7.38 (bs, 6H), 7.30 (d, 1H), 7.15 (bs, 2H), 6.48 (d, 1H), 5.00 (d, 1H, 4.45 (AB, 2H), 4.15 (m, 1H), 3.30 (m, 2H), 2.61 (m, 1H), 1.90 (m, 1H), 1.45 (s, 9H).

E. 7-Methoxynaphthalene-2-sulfonic acid [1-(2-amino-5-cyanobenzyl)-2-oxopyrrolidin-3-yl]amide.

Hydrogen chloride gas is bubbled through a solution of {1-[2-(benzhydrylidenylamino)-5-cyanobenzyl]-2-oxopyrrolidin-3-yl}carbamic acid tert-butyl ester (0.70 g, 1.42 mmol) in 75 mL of EtOAc at 0° C. for 5 minutes. After 1 hour, the solution is concentrated. The resulting residue is dissolved in 50 mL of CH$_3$CN. To the solution is added triethyl amine (0.79 mL, 5.68 mmol) and 7-methoxynaphthalene sulfonyl chloride (0.38 g, 1.49 mmol). After 5 hours, the reaction mixture is diluted with EtOAc. The resulting solution is washed with saturated NaHCO$_3$ and saturated NaCl. The organic layer is dried over MgSO$_4$, filtered and concentrated. The crude material is purified by column chromatography eluting with 5% CH$_3$OH/CH$_2$Cl$_2$. The title compound (0.60 g, 1.21 mmol) is obtained as a yellow solid.

$^1$H NMR (CDCl$_3$, 300 MHz) δ8.30 (s, 1H), 7.90 (d, 1H), 7.80 (d, 1H), 7.70 (d, 1H), 7.35 (m, 4H), 6.55 (d, 1H), 5.25 (d, 1H), 4.90 (s, 2H), 4.30 (AB, 2H), 3.95 (s, 3H), 3.75 (m, 1H), 3.20 (m, 2H), 2.55 (m, 1H), 2.00 (m, 1H).

F. 7-Methoxynaphthalene-2-sulfonic acid [1-(2-amino-5-cyanobenzyl)-2-oxopyrrolidin-3-yl]pyridine-2-ylmethylamide.

2-Picolyl chloride hydrochloride (0.14 g, 0.84 mmol) is added to a solution of 7-methoxynaphthalene-2-sulfonic acid [1-(2-amino-5-cyanobenzyl)-2-oxopyrrolidin-3-yl] amide (0.36 g, 0.80 mmol), potassium carbonate (0.33 g, 2.39 mmol) and tetrabutylammonium iodide (0.07 g, 0.20 mmol) in DMF/acetone (5 mL/20 mL). The resulting solution is heated to reflux overnight and then cooled to room temperature. The reaction mixture is diluted with ethyl acetate and washed with brine. The organic layer is dried over MgSO$_4$, filtered and concentrated. The crude product is purified by column chromatography eluting with a gradient of 10% EtOAc/CH$_2$Cl$_2$ to afford the title product (0.27 g, 0.50) as a foamy white solid.

$^1$H NMR (CDCl$_3$, 300 MHz) δ8.4 (m, 2H), 7.95–7.8 (m, 3H), 7.65 (m, 2H), 7.35–7.23 (m, 4H), 7.15 (m, 1H), 6.55 (d, 1H), 4.9 (bs, 2H), 4.75 (t, 1H), 4.65 (d, 1H), 4.4–4.3 (m, 2H), 4.2–4.15 (m, 1H), 3.95 (s, 3H), 3.1 (m, 2H), 2.75 (m, 1H), 2.0–1.92 (m, 1H).

G. 4-Amino-3-{3-(S)-[(7-methoxy-naphthalene-2-sulfonyl)-pyridine-2-ylmethyl-amino]-2-oxo-pyrrolidin-1-ylmethyl}-benzamidine trifluoroacetate.

The title compound is prepared as described in EXAMPLE 1, Part F using 7-methoxynaphthalene-2-sulfonic acid [1-(2-amino-5-cyanobenzyl)-2-oxopyrrolidin-3-yl]-pyridine-2-ylmethyl-amide as the starting material.

$^1$H NMR (DMSO-d$_6$, 300 MHz) δ8.80 (s, 2H), 8.55 (s, 2H), 8.45 (d, 1H), 8.41 (s, 1H), 8.03 (d, 1H), 7.96 (d, 1H), 7.84 (t, 1H), 7.78 (d, 1H), 7.69 (d, 1H), 7.47–7.54 (m, 2H), 7.41 (s, 1H), 7.30–7.38 (m, 2H), 6.71 (d, 1H), 4.93 (t, 1H), 4.50 (AB, 2H), 4.30 (AB, 2H), 3.91 (s, 3H), 3.15 (m, 2H), 2.16 (m, 1H), 1.78 (m, 1H). FAB MS, [M+H]$^+$=559.

EXAMPLE 69

2-[[1-(2-Amino-5-carbamimidoyl-benzyl)-2-oxo-pyrrolidin-3-(S)-yl}-(7-methoxy-naphthalene-2-sulfonyl)-amino]-acetamide trifluoroacetate.

A. 2-[[1-(2-Amino-5-cyanobenzyl)-2-oxo-pyrrolidin-3-(S)-yl}-(7-methoxy-naphthalene-2-sulfonyl)-amino]-acetic acid tert-butyl ester.

The title compound is prepared as described in Example 66, Part A using 7-methoxynaphthalene-2-sulfonic acid [1-(2-amino-5-cyanobenzyl)-2-oxopyrrolidin-3-yl]amide as the starting material. The crude product is purified by column chromatography eluting with a gradient of 10% EtOAc/CH$_2$Cl$_2$ to 20% EtOAc/CH$_2$Cl$_2$ to afford the product as a yellow oil.

$^1$H NMR (CDCl$_3$, 300 MHz) δ8.40 (s, 1H), 7.90 (d, 1H), 7.77–7.83 (m, 2H), 7.37 (dd, 1H), 7.21–7.31 (m, 3H), 6.58 (d, 1H), 4.92 (s, 2H), 4.61 (m, 1H), 4.30 (AB, 2H), 3.98 (s, 3H), 3.20 (m, 2H), 2.49 (m, 1H), 2.30 (m, 1H), 1.55 (s, 9H).

B. 2-[[1-(2-Amino-5-cyanobenzyl)-2-oxo-pyrrolidin-3-(S)-yl}-(7-methoxy-naphthalene-2-sulfonyl)-amino]-acetic acid.

The title compound is prepared as described in Example 66, Part C using 2-[[1-(2-amino-5-cyanobenzyl)-2-oxo-pyrrolidin-3-(S)-yl}-(7-methoxy-naphthalene-2-sulfonyl)-amino]-acetic acid tert-butyl ester as the starting material. After workup, the crude product is taken on to the next step without further purification.

$^1$H NMR (DMSO-d$_6$, 300 MHz) δ8.42 (s, 1H), 8.05–7.9 (m, 2H), 7.75 (d, 1H), 7.55 (s, 1H), 7.4–7.3 (m, 2H), 7.25–7.15 (m, 2H), 6.65 (d, 1H), 4.85 (m, 2H), 4.2–4.18 (m, 2H) 3.95 (s, 3H), 3.65 (d, 1H), 3.2–3.15 (m, 2H) 2.3–2.2 (m, 1H), 2.15–2.0 (m, 1H).

C. 2-[[1-(2-Amino-5-cyanobenzyl)-2-oxo-pyrrolidin-3-(S)-yl}-(7-methoxy-naphthalene-2-sulfonyl)-amino]-acetamide.

Diisopropylethylamine (0.42 mL, 2.39 mmol) followed by TBTU (2-(1H-benzotriazol-1-yl)-1,1,3,3-tetramethyluronium tetrafluoroborate) (0.27 g, 0.84 mmol) is added to a solution of 2-[[1-(2-amino-5-cyanobenzyl)-2-oxo-pyrrolidin-3-(S)-yl}-(7-methoxy-naphthalene-2-sulfonyl)-amino]-acetic acid in DMF (8 mL). The mixture is stirred for 10 minutes and then concentrated ammonium hydroxide (0.12 mL) is added. After stirring for 2 hours, the reaction mixture is diluted with EtOAc and washed with 1 N HCl, and brine. The organic layer is dried over MgSO$_4$, filtered and concentrated to dryness. The crude product is purified by column chromatography eluting with 5:5:1 EtOAc:CH$_2$Cl$_2$:MeOH to afford the title compound (0.38 g, 0.75 mmol) as a light yellow foamy solid.

$^1$H NMR (CDCl$_3$, 300 MHz) d 8.35 (s, 1H), 8.0 (s, 1H), 7.9–7.85 (d, 1H), 7.8–7.65 (m, 3H), 7.4–7.2 (m, 3H), 6.6 (d, 1H), 5.5 (bs, 1H), 4.95 (bs, 2H), 4.8–4.7 (t, 1H), 4.47 (d, 1H), 4.17 (d, 1H), 3.98 (s, 3H), 3.67 (s, 2H), 3.26 (m, 2H), 2.27 (m, 1H), 1.91 (m, 1H).

D. 2-[[1-(2-Amino-5-carbamimidoyl-benzyl)-2-oxo-pyrrolidin-3-(S)-yl}-(7-methoxy-naphthalene-2-sulfonyl)-amino]-acetamide trifluoroacetate.

The title compound is prepared as described in Example 1, Part F using 2-[[1-(2-amino-5-cyanobenzyl)-2-oxo-pyrrolidin-3-(S)-yl}-(7-methoxy-naphthalene-2-sulfonyl)-amino]-acetamide as the starting material. The product is purified by RP-HPLC eluting in a gradient of 10% CH$_3$CN/H$_2$O (0.1% TFA) to 100% CH$_3$CN and the appropriate product fractions are lyophilized to provide the title compound as a white solid.

$^1$H NMR (DMSO-d$_6$, 300 MHz) d 8.8 (s, 2H), 8.47 (d, 2H), 8.05 (d, 1H), 7.97 (d, 1H), 7.77 (d, 1H), 7.6–7.5 (m, 3H), 7.47 (s, 1H), 7.37 (m, 1H), 7.22 (s, 1H), 6.72 (d, 1H), 6.40–6.00 (b, 1H), 4.84 (t, 1H), 4.27 (AB, 2H), 3.90 (s, 3H), 3.86 (d, 1H), 3.20 (m, 2H), 2.15 (m, 1H), 2.05 (m, 1H). FAB MS, [M+H]$^+$=525.

EXAMPLE 70

[Imino-(3-{3-[(7-methoxy-naphthalene-2-sulfonyl)-methylamino]-2-oxo-3-(S)-pyrrolidin-1-ylmethyl}-4-amino-phenyl)-methyl]carbamic acid ethyl ester.

A. {1-[2-(Benzhydrylidenylamino)-5-cyano-benzyl]-2-oxopyrrolidin-3-yl}-N-methylcarbamic acid tert-butyl ester.

To a solution of {1-[2-(benzhydrylidenylamino)-5-cyanobenzyl]-2-oxopyrrolidin-3-yl}carbamic acid tert-butyl ester (3.94 g, 7.98 mmol) in 8 mL of DMF at 0° C. is added a 60% mineral oil dispersion of NaH (0.35 g, 8.77 mmol). After 20 minutes, methyl iodide (0.99 mL, 15.9 mmol) is added. After 2 hours, the solution is diluted with saturated $NH_4Cl$ and EtOAc. The layers are separated. The organic layer is washed with $H_2O$ and saturated NaCl. The organic layer is dried over $MgSO_4$, filtered and concentrated. The crude material is purified by column chromatography eluting with a gradient of 30% EtOAc/hexanes to 50% EtOAc/hexanes. The title compound (3.72 g, 7.31 mmol) is obtained as a yellow solid.

$^1$H NMR ($CDCl_3$, 300 MHz) δ7.70 (bs, 2H), 7.45 (m, 8H), 7.10 (bs, 2H), 6.45 (dd, 1H), 4.70 (m, 1H), 4.49 (AB, 2H), 3.30 (m, 2H), 2.83 (s, 3H), 2.35 (m, 1H), 2.10 (m, 1H), 1.50 (s, 9H). FAB MS, [M+H]$^+$=509.

B. 7-Methoxynaphthalene-2-sulfonic acid [1-(2-amino-5-cyanobenzyl)-2-oxopyrrolidin-3-yl]-N-methylamide.

The title compound is prepared as described in EXAMPLE 1, Part E substituting {1-[2-(benzhydrylidenylamino)-5-cyanobenzyl]-2-oxopyrrolidin-3-yl}-N-methylcarbamic acid tert-butyl ester for {1-[2-(benzhydrylidenylamino)-5-cyanobenzyl]-2-oxopyrrolidin-3-yl}carbamic acid tert-butyl ester. The title compound is obtained as a yellow solid.

$^1$H NMR ($CDCl_3$, 300 MHz) δ8.38 (s, 1H), 7.87 (d, 1H), 7.78 (d, 1H), 7.72 (dd, 1H), 7.32 (dd, 1H), 7.30 (dd, 1H), 7.28 (d, 1H), 7.23 (dd, 1H), 6.55 (d, 1H), 4.98 (s, 2H), 4.25 (AB, 2H), 4.15 (m, 1H), 3.98 (s, 3H), 3.20 (m, 2H), 2.70 (s, 3H), 1.95 (m, 1H).

C. 4-Amino-3-[3-(S)-(7-methoxynaphthalene-2-sulfonyl-N-methylamino)-2-oxopyrrolidin-1-ylmethyl]benzamidine trifluoroacetate.

7-Methoxynaphthalene-2-sulfonic acid [1-(2-amino-5-cyano-benzyl)-2-oxopyrrolidin-3-yl]methylamide is converted to the title compound as described in EXAMPLE 1, Part F. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-d$_6$, 300 MHz) δ8.90 (bs, 2H), 8.75 (bs, 2H), 8.40 (s, 1H), 8.050 (d, 1H), 7.95 (d, 1H), 7.70 (dd, 1H), 7.60 (d, 1H), 7.55 (dd, 1H), 7.48 (d, 1H), 7.39 (dd, 1H), 6.70 (d, 1H), 6.00 (bs, 1H), 4.98 (m, 1H), 4.20 (AB, 2H), 3.90 (s, 3H), 3.15 (m, 2H), 2.67 (s, 3H), 2.05 (m, 1H), 1.70 (m, 1H). FAB MS, [M+H]$^+$=482. Elemental analysis calculated with 1.3 mmol of $H_2O$, 1.5 mol $CF_3CO_3H$, cal C=50.73%, H=4.53%, N=11.12% found C=50.50%, H=4.50%, N=10.99%.

D. [Imino-(3-{3-[(7-methoxy-naphthalene-2-sulfonyl)-methylamino]-2-oxo-3-(S)-pyrrolidin-1-ylmethyl}-4-amino-phenyl)-methyl]carbamic acid ethyl ester.

The title compound is prepared as described in Example 67, Part C using 4-amino-3-[3-(S)-(7-methoxynaphthalene-2-sulfonylmethylamino)-2-oxopyrrolidin-1-ylmethyl]benzamidine trifluoroacetate as the starting material. The crude product is purified by column chromatography eluting with 3% $MeOH/CH_2Cl_2$ to give a white solid as the product.

$^1$H NMR ($CDCl_3$, 300 MHz) δ9.60 (bs, 1H), 8.41 (s, 1H), 7.97 (d, 1H), 7.70–7.80 (m, 3H), 7.54 (d, 1H), 7.30 (m, 2H), 6.50 (d, 1H), 4.90 (m, 1H), 4.85 (s, 2H), 4.40 (AB, 2H), 4.30 (q, 2H), 3.98 (s, 3H), 3.25 (m, 2H), 2.80 (s, 3H), 2.25 (m, 1H), 1.95 (m, 1H), 1.35 (t, 3H). FAB MS, [M+H]$^+$=554.

EXAMPLE 71

4-Hydroxy-3-{3-(S)-[5-(1-Hydroxy-pyridin-4-yl)-thiophene-2-sulfonyl amino]-2-oxo-pyrrolidin-1-ylmethyl}-benzamidine trifluoroacetate A. 5-Pyridin-4-yl-thiophene-2-sulfonic acid [1-(5-cyano-2-hydroxybenzyl)-2-oxo-pyrrolidin-3-(S)-yl]-amide The title compound is prepared as described in Example 17, Part G using 5-pyridin-4-yl-thiophene-2-sulfonyl chloride in place of 4,6-dichlorobenzo[b]thio-phene-2-sulfonyl chloride.

$^1$H NMR ($CDCl_3$, 300 MHz) δ9.30 (bs, 1H), 8.68 (m, 2H), 7.70 (d, 1H), 7.53 (dd, 1H), 7.40–7.45 (m, 3H), 7.39 (d, 1H), 6.98 (d, 1H), 5.34 (d, 1H), 4.34 (AB, 2H), 4.05 (m, 1H), 2.70 (m, 2H), 2.10 (m, 1H), 0.98 (m, 1H). FAB MS, [M+H]$^+$=455.

B. 5-Pyridin-4-yl-thiophene-2-sulfonic acid [1-[2-(tert-butyl-dimethyl-silanyloxy)-5-cyano-benzyl]-2-oxo-pyrrolidin-3-(S)-yl]-amide.

Tert-butyldimethylsilyl chloride (0.129 g, 0.856 mmol) is added to a solution of 5-pyridin-4-yl-thiophene-2-sulfonic acid [1-(5-cyano-2-hydroxybenzyl)-2-oxo-pyrrolidin-3-(S)-yl]amide (0.325 g, 0.715 mmol) and imidazole (0.122 g, 1.79 mmol) in DMF (14 mL). The resulting mixture is stirred overnight at room temperature and then diluted with EtOAc and washed with saturated sodium bicarbonate, water and brine. The organic layer is dried over $MgSO_4$, filtered and concentrated to dryness. The crude product is purified by column chromatography eluting with 5% MeOH/$CH_2Cl_2$ to give the title compound (0.330 g, 0.580 mmol) as a foamy yellow solid.

$^1$H NMR ($CDCl_3$, 300 MHz) δ8.70 (m, 2H), 7.70 (d, 1H), 7.45–7.50 (m, 4H), 7.30 (d, 1H), 6.88 (d, 1H), 5.45 (d, 1H), 4.45 (AB, 2H), 3.98 (m, 1H), 3.20 (m, 2H), 2.61 (m, 1H), 2.13 (m, 1H), 0.98 (s, 9H), 0.25 (s, 6H). FAB MS, [M+H]$^+$=569.

C. 5-(1-Hydroxy-pyridin-4-yl)-thiophene-2-sulfonic acid [1-[2-(tert-butyl-dimethyl-silanyloxy)-5-cyano-benzyl]-2-oxo-pyrrolidin-3-(S)-yl]-amide.

m-Chloroperbenzoic acid (0.309 g, of a ~65% grade of m-CPBA) is added to a solution of 5-pyridin-4-yl-thiophene-2-sulfonic acid [1-[2-(tert-butyl-dimethyl-silanyloxy)-5-cyano-benzyl]-2-oxo-pyrrolidin-3-(S)-yl]-amide (0.330 g, 0.54 mmol) in $CH_2Cl_2$ (19 mL). The resulting solution is stirred at room temperature for 5 hours and then diluted with additional $CH_2Cl_2$ and washed with saturated sodium bicarbonate solution and brine. The organic layer is dried over $MgSO_4$, filtered and concentrated. The crude material is used in the subsequent step without further purification.

$^1$H NMR ($CDCl_3$, 300 MHz) δ8.23 (d, 2H), 7.68 (d, 1H), 7.50 (d, 2H), 7.38 (d, 1H), 7.30 (d, 1H), 6.90 (d, 1H), 5.45 (d, 1H), 4.45 (AB, 2H), 3.98 (m, 1H), 4.23 (m, 2H), 2.70 (m, 1H), 2.20 (m, 1H), 0.98 (s, 9H), 0.20 (s, 6H). FAB MS, [M+H]$^+$=585.

D. 4-Hydroxy-3-{3-(S)-[5-(1-Hydroxy-pyridin-4-yl)-thiophene-2-sulfonyl amino]-2-oxo-pyrrolidin-1-ylmethyl}-benzamidine trifluoroacetate.

The title compound is prepared as described in Example 1, Part F using 5-pyridin-4-yl-thiophene-2-sulfonic acid [1-(5-cyano-2-hydroxybenzyl)-2-oxo-pyrrolidin-3-(S)-yl]-amide as the starting material. The crude product is purified by RP-HPLC eluting with a gradient of 10% $CH_3CN/H_2O$ (0.1% TFA) to 100% $CH_3CN$ and the appropriate product fractions are lyophilized to provide the title compound as a white solid.

¹H NMR (DMSO-d₆, 300 MHz) δ9.98 (bs, 1H), 9.10 (s, 2H), 8.80 (s, 2H), 8.50 (d, 1H), 8.30 (d, 2H), 7.68–7.80 (m, 4H), 7.61 (d, 1H), 7.40 (d, 1H), 6.98 (d, 1H), 4.45 (AB, 2H), 4.20 (m, 1H), 3.20 (m, 2H), 2.14 (m, 1H), 1.70 (m, 1H). Ion spray MS, [M+H]⁺=488.

EXAMPLE 72
4-Amino-3-[3-(S)-(5-chloro-thieno[3,2-b]pyridine-2-sulfonylamino)-2-oxo-pyrrolidin-1-ylmethyl]-hydroxybenzamidine trifluoroacetate.

5-Chlorothieno[3,2-b]pyridine-2-sulfonic acid [1-(2-amino-5-cyanobenzyl)-2-oxo-pyrrolidin-3-(S)-yl]-amide is converted to the title compound as described in EXAMPLE 27. The crude product is purified by RP-HPLC eluting in a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ8.97 (bs, 1H), 8.94 (d, 1H), 8.68 (d, 1H), 8.66 (bs, 1H), 8.10 (s, 1H), 7.64 (d, 1H), 7.37 (d, 1H), 7.28 (s, 1H), 6.71 (d, 1H), 6.07 (bs, 2H), 4.31 (m, 1H), 4.18 (AB, 2H), 3.21 (m, 2H), 2.21 (m, 1H), 1.70 (m, 1H). FAB MS, [M+H]⁺=495, 497, Cl pattern. Elemental analysis calculated with 1.05 mol H₂O; C=40.17%, H=3.55%, N=13.38%, Cl=5.65, found: C=40.16%, H=2.99%, N=12.99%, Cl=6.28%.

EXAMPLE 73
4-Amino-3-[3-(S)-(5-methoxy-thieno[3,2-b]pyridine-2-sulfonylamino)-2-oxo-pyrrolidin-1-ylmethyl]-benzamidine bistrifluoroacetate.

4-Amino-3-[3-(S)-(5-chlorothieno[3,2-b]pyridine-2-sulfonylamino)-2-oxo-pyrrolidin-1-ylmethyl]-benzamidine trifluoroacetate is converted to the title compound as described in EXAMPLE 26. The reaction mixture is heated at 50° C. and hydrogenated at 50 p.s.i. for 3 days. The crude product is purified by RP-HPLC eluting in a gradient of 10% CH₃CN/H₂O (0.1% TFA) to 80% CH₃CN/H₂O (0.1% TFA) and the appropriate product fractions are lyophilized to provide 4-amino-3-[2-oxo-3-(S)-(thieno[3,2-b]pyridine-2-sulfonylamino)-pyrrolidin-1-ylmethyl]-benzamidine bistrifluoroacetate as the major product and the title compound as a minor by-product as a white solid.

¹H NMR (DMSO-d₆, 300 MHz) δ8.80 (bs, 2H), 8.77 (d, 1H), 8.48 (bs, 2H), 8.45 (d, 1H), 7.96 (s, 1H), 7.53 (dd, 1H), 7.41 (d, 1H), 7.02 (d, 1H), 6.71 (d, 1H), 4.30 (m, 1H), 4.20 (AB, 2H), 3.95 (s, 3H), 3.20 (m, 2H), 2.20 (m, 1H), 1.69 (m, 1H). FAB MS, [M+H]⁺=475.

EXAMPLE 74
3-[3-(S)-(5-Isoxazol-3-yl-thiophene-2-sulfonylamino)-2-oxo-pyrrolidin-1-ylmethyl]-benzamidine trifluoroacetate.

A. 5-Isoxazol-3-yl-thiophene-2-sulfonic acid [1-(3-cyanobenzyl)-2-oxo-pyrrolidin-3-(S)-yl]-amide.

The title compound is prepared from 3-(3-(S)-amino-2-oxo-pyrrolidin-1-ylmethyl)-benzonitrile hydrochloride as described in EXAMPLE 1, Part E using 5-isoxazol-3-yl-thiophene-2-sulfonyl chloride in place of benzo[b]thiophene-2-sulfonyl chloride. The crude product is used in the subsequent step without further purification.

¹H NMR (CDCl₃, 300 MHz) δ8.36 (d, 1H), 7.70 (d, 1H), 7.61 (m, 1H), 7.49 (m, 4H), 6.57 (d, 1H), 5.55 (bs, 1H), 4.51 (s, 2H), 3.97 (m, 1H), 3.29 (m, 2H), 2.69 (m, 1H), 2.17 (m, 1H).

B. 3-[3-(S)-(5-Isoxazol-3-yl]-thiophene-2-sulfonylamino)-2-oxo-pyrrolidin-1-ylmethyl]-benzamidine trifluoroacetate.

5-Isoxazol-3-yl-thiophene-2-sulfonic acid [1-(3-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH₃CN/H₂O (0.1% TFA) to 40% CH₃CN/H₂O (0.1% TFA) and the appropriate product fractions are lyophilized to provide the title compound as a white solid.

¹H NMR (DMSO-d₆, 300 MHz) δ9.31 (bs, 2H), 9.22 (bs, 2H), 8.74 (s, 1H), 8.70 (d, 1H), 7.75 (m, 3H), 7.57 (m, 3H), 7.10 (d, 1H), 4.44 (AB, 2H), 4.26 (m, 1H), 3.15 (m, 2H), 2.20 (m, 1H), 1.71 (m, 1H). FAB MS, [M+H]⁺=446. Elemental analysis calculated with 1.58 mol H₂O: C=42.90%, H=3.97%, N=11.91%, found: C=42.92%, H=3.39%, N=11.31%.

EXAMPLE 75
4-Amino-3-[3-(S)-(5-isoxazol-3-yl-thiophene-2-sulfonylamino)-2-oxo-pyrrolidin-1-ylmethyl]-benzamidine trifluoroacetate.

A. 5-Isoxazol-3-yl-thiophene-2-sulfonic acid [1-(2-amino-5-cyanobenzyl)-2-oxo-pyrrolidin-3-(S)-yl]-amide.

The title compound is prepared from 4-amino-3-(3-(S)-amino-2-oxo-pyrrolidin-1-ylmethyl)-benzonitrile dihydrochloride as described in EXAMPLE 17, Part F using 5-isoxazol-3-yl-thiophene-2-sulfonyl chloride in place of 4,6-dichlorobenzo[b]thiophene-2-sulfonyl chloride. The crude product is used in the subsequent step without further purification.

¹H NMR (CDCl₃, 300 MHz) δ8.35 (d, 1H), 7.81 (d, 1H), 7.69 (d, 1H), 7.50 (d, 2H), 7.39 (dd, 1H), 6.65 (d, 1H), 6.59 (d, 1H), 4.32 (AB, 2H), 4.02 (m, 1H), 3.30 (m, 2H), 2.60 (m, 1H), 2.08 (m, 1H).

B. 4-Amino-3-[3-(S)-(5-isoxazol-3-yl-thiophene-2-sulfonylamino)-2-oxo-pyrrolidin-1-ylmethyl]-benzamidine trifluoroacetate.

5-Isoxazol-3-yl-thiophene-2-sulfonic acid [1-(2-amino-5-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH₃CN/H₂O (0.1% TFA) to 70% CH₃CN/H₂O (0.1% TFA) and the appropriate product fractions are lyophilized to afford the title compound as a white solid.

¹H NMR (DMSO-d₆, 300 MHz) δ8.80 (bs, 2H), 8.75 (d, 1H), 8.70 (d, 1H), 8.52 (bs, 2H), 7.75 (s, 2H), 7.52 (dd, 1H), 7.45 (d, 1H), 7.10 (d, 1H), 6.71 (d, 1H), 6.20 (bs, 1H), 4.28 (m, 1H), 4.21 (AB, 2H), 3.20 (m, 2H), 2.20 (m, 1H), 1.70 (m, 1H). IS MS, [M+H]⁺=461.

EXAMPLE 76
4-Hydroxy-3-[3-(S)-(5-isoxazol-3-yl-thiophene-2-sulfonylamino)-2-oxo-pyrrolidin-1-ylmethyl}-benzamidine trifluoroacetate.

A. 5-Isoxazol-3-yl-thiophene-2-sulfonic acid [1-(5-cyano-2-hydroxybenzyl)-2-pyrrolidin-3-(S)-yl]-amide.

The title compound is prepared from 4-hydroxy-3-(3-(S)-amino-2-oxo-pyrrolidin-1-ylmethyl)-benzonitrile hydrochloride as described in EXAMPLE 17, Part F using 5-isoxazol-3-yl-thiophene-2-sulfonyl chloride in place of 4,6-dichlorobenzo[b]thiophene-2-sulfonyl chloride. The crude product is purified by column chromatography eluting with 50% EtOAc/CH₂Cl₂ to give a solid.

¹H NMR (CDCl₃, 300 MHz) δ9.37 (bs, 1H), 8.35 (d, 2H), 7.50 (m, 2H), 7.41 (d, 1H), 7.00 (d, 1H), 6.57 (d, 1H), 5.48 (bs, 1H), 4.35 (AB, 2H), 4.10 (m, 1H), 3.50 (m, 2H), 2.70 (m, 1H), 2.20 (m, 1H).

B. 4-Hydroxy-3-[3-(S)-(5-isoxazol-3-yl-thiophene-2-sulfonylamino)-2-oxo-pyrrolidin-1-ylmethyl}-benzamidine trifluoroacetate.

5-Isoxazol-3-yl-thiophene-2-sulfonic acid [1-(5-cyano-2-hydroxybenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to afford the title compound as a pale yellow solid.

$^1$H NMR (DMSO-d$_6$, 300 MHz) δ9.04 (bs, 2H), 8.87 (bs, 2H), 8.73 (d, 1H), 8.67 (d, 1H), 7.74 (m, 2H), 7.61 (dd, 1H), 7.42 (d, 1H), 7.09 (d, 1H), 6.97 (d, 1H), 4.33 (AB, 2H), 4.23 (m, 1H), 3.21 (m, 2H), 2.21 (m, 1H), 1.75 (m, 1H). IS MS, [M+H]$^+$=462. Elemental analysis calculated with 0.87 mol H$_2$O: C=42.65%, H=3.49%, N=11.41%, found: C=42.65%, H=3.49%, N=11.41%.

EXAMPLE 77

3-(S)-[3-([2,2']-Bithiophenyl-5-sulfonylamino)-2-oxo-pyrrolidin-1-ylmethyl]-benzamidine trifluoroacetate.
A. [2,2']Bithiophenyl-5-sulfonyl chloride.

The title compound is prepared as described in EXAMPLE 1, Part D using [2,2']-bithiophene in place of thianaphthalene. The crude product is purified by column chromatography eluting with 5% EtOAc/hexanes to give a pale green solid.

$^1$H NMR (CDCl$_3$, 300 MHz) δ7.78 (d, 1H), 7.43 (d, 1H), 7.36 (d, 1H), 7.17 (d, 1H), 7.10 (t, 1H). EI MS, [M]$^+$=264, 266, Cl pattern.
B. [2,2']-Bithiophenyl-5-sulfonic acid [1-(3-cyanobenzyl)-2-oxo-pyrrolidin-3-(S)-yl]-amide.

The title compound is prepared from 3-(3-(S)-amino-2-oxo-pyrrolidin-1-ylmethyl)-benzonitrile hydrochloride as described in EXAMPLE 1, Part E using [2,2']bithiophenyl-5-sulfonyl chloride in place of benzo[b]thiophene-2-sulfonyl chloride. The crude product is used in the subsequent step without further purification.

$^1$H NMR (CDCl$_3$, 300 MHz) δ7.60 (d, 2H), 7.50 (s, 1H), 7.46 (d, 2H), 7.34 (d, 1H), 7.28 (d, 1H), 7.13 (d, 1H), 7.06 (m, 1H), 5.46 (bs, 1H), 4.48 (s, 2H), 3.91 (m, 1H), 3.26 (m, 2H), 2.68 (m, 1H), 2.19 (m, 1H).
C. 3-(S)-[3-([2,2']-Bithiophenyl-5-sulfonylamino)-2-oxo-pyrrolidin-1-ylmethyl]-benzamidine trifluoroacetate.

[2,2']-Bithiophenyl-5-sulfonic acid [1-(3-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.30 (bs, 2H), 9.10 (bs, 2H), 8.51 (d, 1H), 7.68 (m, 2H), 7.58 (m, 4H), 7.50 (d, 1H), 7.35 (d, 1H), 7.15 (m, 1H), 4.47 (AB, 2H), 4.21 (m, 1H), 3.19 (m, 2H), 2.20 (m, 1H), 1.71 (m, 1H). IS MS, [M+H]$^+$= 461. Elemental analysis calculated with 0.95 mol H$_2$O: C=44.66%, H=3.90%, N=9.47%, found: C=44.65%, H=3.20%, N=9.05%.

EXAMPLE 78

4-Amino-3-[3-(S)-([2,2']-bithiophenyl-5-sulfonylamino)-2-oxo-pyrrolidin-1-ylmethyl]-benzamidine trifluoroacetate.
A. [2,2']-Bithiophenyl-5-sulfonic acid [1-(2-amino-5-cyanobenzyl)-2-oxo-pyrrolidin-3-(S)-yl]-amide.

The title compound is prepared from 4-amino-3-(3-(S)-amino-2-oxo-pyrrolidin-1-ylmethyl)-benzonitrile dihydrochloride as described in EXAMPLE 17, Part F using [2,2'bithiophenyl-5-sulfonyl chloride in place of 4,6-dichlorobenzo[b]thiophene-2-sulfonyl chloride. The crude product is purified by column chromatography eluting with a gradient of 10% EtOAc/CH$_2$Cl$_2$ to 25% EtOAc/CH$_2$Cl$_2$ to yield a solid.

$^1$H NMR (CDCl$_3$, 300 MHz) δ7.54 (d, 1H), 7.36 (m, 2H), 7.30 (m, 2H), 7.12 (d, 1H), 7.07 (dd, 1H), 6.60 (d, 1H), 5.39 (bs, 1H), 4.93 (bs, 2H), 4.31 (AB, 2H), 3.94 (m, 1H), 3.30 (m, 2H), 2.65 (m, 1H), 2.11 (m, 1H).
B. 4-Amino-3-[3-(S)-([2,2']-bithiophenyl-5-sulfonylamino)-2-oxo-pyrrolidin-1-ylmethyl]-benzamidine trifluoroacetate.

[2,2']-Bithiophenyl-5-sulfonic acid [1-(2-amino-5-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to afford the title compound as a white solid.

$^1$H NMR (DMSO-d$_6$, 300 MHz) δ8.79 (bs, 2H), 8.50 (d, 1H), 8.48 (bs, 2H), 7.65 (dd, 1H), 7.59 (d, 1H), 7.51 (dd, 1H), 7.47 (d, 1H), 7.43 (d, 1H), 7.34 (d, 1H), 7.14 (m, 1H), 6.72 (d, 1H), 6.20 (bs, 2H), 4.20 (m, 3H), 3.20 (m, 2H), 2.20 (m, 1H), 1.70 (m, 1H). FAB MS, [M+H]$^+$=476. Elemental analysis calculated with 1.2 mol H$_2$O cal. C=43.23%, H=4.02%, N=11.46%, found: C=43.17%, H=3.43%, N=10.87%.

EXAMPLE 79

4-Amino-3-[3-(S)-(5'-chloro-[2,2']-bithiophenyl-5-sulfonylamino)-2-oxo-pyrrolidin-1-ylmethyl]-benzamidine trifluoroacetate.
A. 5'-Chloro-[2,2']-bithiophenyl-5-sulfonic acid [1-(2-amino-5-cyanobenzyl)-2-oxo-pyrrolidin-3-(S)-yl]-amide.

The title compound is prepared from 4-amino-3-(3-(S)-amino-2-oxo-pyrrolidin-1-ylmethyl)-benzonitrile dihydrochloride as described in EXAMPLE 17, Part F using [2,2']bithiophenyl-5-sulfonyl chloride in place of 4,6-dichlorobenzo[b]thiophene-2-sulfonyl chloride. The crude product is purified by column chromatography eluting with a gradient of 10% EtOAc/CH$_2$Cl$_2$ to 30% EtOAc/CH$_2$Cl$_2$ to yield a beige solid.

$^1$H NMR (CDCl$_3$+CD$_3$OD, 300 MHz) δ7.59 (d, 1H), 7.39 (dd, 1H), 7.31 (dd, 1H), 7.08 (m, 2H), 6.90 (d, 1H), 6.65 (d, 1H), 4.30 (AB, 2H), 4.05 (m, 1H), 3.25 (m, 2H), 2.52 (m, 1H), 2.03 (m, 1H).
B. 4-Amino-3-[3-(S)-(5'-chloro-[2,2']-bithiophenyl-5-sulfonylamino)-2-oxo-pyrrolidin-1-ylmethyl]-benzamidine trifluoroacetate.

5-Chloro-[2,2']-bithiophenyl-5-sulfonic acid [1-(2-amino-5-cyanobenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to afford the title compound as a white solid.

$^1$H NMR (DMSO-d$_6$, 300 MHz) δ8.84 (bs, 2H), 8.74 (bs, 2H), 8.57 (d, 1H), 7.61 (d, 1H), 7.56 (dd, 1H), 7.49 (dd, 1H), 7.39 (dd, 2H), 7.20 (d, 1H), 6.75 (d, 1H), 4.22 (m, 3H), 3.20 (m, 2H), 2.19 (m, 1H), 1.70 (m, 1H). FAB MS, [M+H]$^+$= 510, 512, Cl pattern. Elemental analysis calculated with 1.1 mol H$_2$O cal. C=41.07%, H=3.63%, N=10.88%, Cl=5.51%, found: C=41.08%, H=3.14%, N=10.44%, Cl=5.77%.

EXAMPLE 80

4-Hydroxy-3-[3-(S)-(5'-chloro-[2,2']-bithiophenyl-5-sulfonylamino)-2-oxo-pyrrolidin-1-ylmethyl]-benzamidine hydrochloride.
A. 5'-Chloro-[2,2']-bithiophenyl-5-sulfonic acid [1-(5-cyano-2-hydroxybenzyl)-2-oxo-pyrrolidin-3-(S)-yl]-amide.

The title compound is prepared from 4-hydroxy-3-(3-(S)-amino-2-oxo-pyrrolidin-1-ylmethyl)-benzonitrile hydrochloride as described in EXAMPLE 17, Part F using 5'-chloro-[2,2']-bithiophenyl-5-sulfonyl chloride in place of 4,6-dichlorobenzo[b]thiophene-2-sulfonyl chloride. The crude product is purified by column chromatography eluting with 25% EtOAc/CH$_2$Cl$_2$ to give a solid.

$^1$H NMR (CDCl$_3$, 300 MHz) δ9.30 (s, 1H), 7.57 (d, 1H), 7.53 (s, 1H), 7.43 (s, 1H), 7.30 (s, 1H), 7.08 (m, 1H), 7.00 (d, 1H), 6.90 (d, 1H), 5.40 (bs, 1H), 4.36 (AB, 2H), 4.05 (m, 1H), 3.51 (m, 2H), 2.70 (m, 1H), 2.20 (m, 1H).

B. 4-Hydroxy-3-[3-(S)-(5'-chloro-[2,2']-bithiophenyl-5-sulfonylamino)-2-oxo-pyrrolidin-1-ylmethyl}-benzamidine hydrochloride.

5-'-Chloro-[2,2']-bithiophenyl-5-sulfonic acid [1-(5-cyano-2-hydroxybenzyl)-2-oxo-pyrrolidin-3-(S)-yl]-amide is converted to the title compound as described in EXAMPLE 1, Part F. The crude product is purified by RP-HPLC eluting in a gradient of 10% CH$_3$CN/H$_2$O (0.05% HCl) to 80% CH$_3$CN/H$_2$O (0.05% HCl) and the appropriate product fractions are lyophilized to afford the title compound as a pale yellow solid.

$^1$H NMR (DMSO-d$_6$, 300 MHz) δ9.56 (bs, 2H), 9.24 (bs, 2H), 8.74 (d, 1H), 8.71 (d, 1H), 8.07 (m, 2H), 7.98 (s, 1H), 7.61 (d, 1H), 7.42 (m, 1H), 4.45 (AB, 2H), 4.31 (m, 1H), 3.20 (m, 2H), 2.20 (m, 1H), 1.79 (m, 1H). IS MS, [M+H]$^+$= 511, 513, Cl pattern.

EXAMPLE 81

4-Hydroxy-3-[3-(S)-(5'-chloro-[2,2']-bithiophenyl-5-sulfonylamino)-2-oxo-pyrrolidin-1-ylmethyl]-hydroxybenzamidine.

5'-Chloro-[2,2']-bithiophenyl-5-sulfonic acid [1-(5-cyano-2-hydroxybenzyl)-2-oxo-pyrrolidin-3-(S)-yl]-amide is converted to the title compound as described in EXAMPLE 27. The crude product is purified by column chromatography eluting with a gradient of 5% MeOH/CH$_2$Cl$_2$ to 10% MeOH/CH$_2$Cl$_2$ to provide the title compound as a white solid.

$^1$H NMR (DMSO-d$_6$, 300 MHz) δ9.83 (s, 1H), 9.38 (s, 1H), 8.53 (d, 1H), 7.60 (d, 1H), 7.40 (dd, 1H), 7.39 (d, 1H), 7.34 (d, 1H), 7.31 (s, 1H), 6.78 (d, 1H), 5.66 (bs, 2H), 4.29 (AB, 2H), 4.10 (m, 1H), 3.15 (m, 2H), 2.20 (m, 1H), 1.67 (m, 1H). FAB MS, [M+H]$^+$=527, 529 Cl pattern. Elemental analysis calculated with 0.70 mol H$_2$O cal. C=44.52%, H=3.81%, N=9.67%, Cl=8.51%, found: C=44.52%, H=3.59%, N=9.67%, Cl=8.51%.

EXAMPLE 82

4-[3-(S)-(6-Fluoro-benzo[b]thiophene-2-sulfonylamino)-2-oxo-pyrrolidin-1-ylmethyl]-pyridine-2-carboxamidine hydrochloride.

A. 2-Cyano-4-[{(tert-butyldimethylsilyl)oxy}methyl] pyridine.

The title compound is prepared according to the procedure described in *J. Heterocyclic Chem.* 1993, 30, 631. The crude residue obtained is purified by column chromatography eluting with gradient of 5% EtOAc/hexanes to 20% EtOAc/hexanes to give the title compound as a yellow oil.

$^1$H NMR (CDCl$_3$, 300 MHz) δ8.66 (d, 1H), 7.69 (s, 1H), 7.48 (m, 1H), 4.80 (s, 2H), 1.00 (s, 9H), 0.19 (s, 6H).

B. 2-Cyano-4-(hydroxymethyl)pyridine.

A solution of 2-cyano-4-[{(tert-butyldimethylsilyl) oxy}methyl]pyridine (10.1 g, 40.5 mmol) in 200 mL of anhydrous MeOH is stirred over 12 g of Dowex-50W-H$^+$ ion-exchange resin (pre-washed with MeOH) for a period of 18 hours. After this time, the mixture is filtered and washed with MeOH twice. The combined filtrates are concentrated in vacuo. The crude residue is purified by column chromatography eluting with 50% EtOAc/hexanes to yield the title compound (4.82 g, 35.9) as an oil.

$^1$H NMR (CDCl$_3$, 300 MHz) δ8.70 (m, 1H), 7.75 (s, 1H), 7.55 (d, 1H), 4.87 (d, 2H), 2.31 (bs, 1H).

C. 2-Cyano-4-(bromomethyl)pyridine.

Bromine (6.88 g, 43.1 mmol) is added dropwise to a solution of triphenylphosphine (11.3 g, 43.1 mmol) in 280 mL of CH$_2$Cl$_2$ at 0° C. The mixture is stirred for 30 minutes at 0° C. At this time, 2-cyano-4-(hydroxymethyl)pyridine (4.82 g, 35.9 mmol) is added and the resulting mixture is stirred for 2 hours at room temperature. The reaction mixture is diluted with CH$_2$Cl$_2$ and washed with water (2×) and saturated NaCl solution. The organic layer is dried with MgSO$_4$, filtered and concentrated. The crude product is purified by column chromatography eluting in a gradient of 20% EtOAc/hexanes to 30% EtOAc/hexanes to afford the title compound (6.40 g, 32.5 mmol) as an oil.

$^1$H NMR (CDCl$_3$, 300 MHz) δ8.75 (d, 1H), 7.79 (s, 1H), 7.60 (d, 1H), 4.49 (s, 2H).

D. [1-(2-Cyano-pyridin-4-ylmethyl)-2-oxo-pyrrolidin-3-(S)-yl]-carbamic acid tert-butyl ester.

The title compound is prepared from (2-oxo-pyrrolidin-3-(S)-yl)-carbamic acid tert-butyl ester as described in EXAMPLE 1, Part B using 2-cyano-4-(bromomethyl) pyridine in place of α-bromo-m-toluoyl nitrile. The crude product is purified by column chromatography eluting with gradient of 25% EtOAc/CH$_2$Cl$_2$ to 50% EtOAc/CH$_2$Cl$_2$ to afford the title compound as a solid.

$^1$H NMR (CDCl$_3$, 300 MHz) δ8.69 (d, 1H), 7.70 (s, 1H), 7.46 (d, 1H), 5.42 (bs, 1H), 4.57 (AB, 2H), 4.22 (m, 1H), 3.35 (m, 2H), 2.62 (m, 1H), 2.10 (m, 1H), 1.50 (s, 9H).

E. 4-(3-(S)-Amino-2-oxo-pyrrolidin-1-ylmethyl)pyridine-2-carbonitrile trifluoroacetate.

To a solution of [1-(2-cyano-pyridin-4-ylmethyl)-2-oxo-pyrrolidin-3-(S)-yl]-carbamic acid tert-butyl ester (3.34 g, 10.6 mmol) in 50 mL of CH$_2$Cl$_2$ is added 5 mL of TFA. The reaction mixture is stirred for 18 hours and then concentrated to give the title compound (3.40 g, 10.3 mmol) as a white foam.

$^1$H NMR (DMSO-d$_6$, 300 MHz) δ7.90 (d, 1H), 7.70 (bs, 3H), 7.09 (s, 1H), 6.80 (m, 1H), 3.78 (AB, 2H), 3.35 (m, 1H), 2.55 (m, 2H), 1.62 (m, 1H), 1.20 (m, 1H).

F. 6-Fluoro-benzo[b]thiophene-2-sulfonic acid [1-(2-cyano-pyridin-4-ylmethyl)-2-oxo-pyrrolidin-3-(S)-yl]-amide.

The title compound is prepared as described in EXAMPLE 1, Part E using 6-fluoro-benzo[b]thiophene-2-sulfonyl chloride and 4-(3-(S)-amino-2-oxo-pyrrolidin-1-ylmethyl)pyridine-2-carbonitrile trifluoroacetate in place of 3-(3-(S)-amino-2-oxo-pyrrolidin-1-ylmethyl)-benzonitrile hydrochloride. The crude product is purified by column chromatography eluting with a gradient of 10% EtOAc/CH$_2$Cl$_2$ to 25% EtOAc/CH$_2$Cl$_2$ to provide the title compound as a white solid.

$^1$H NMR (CDCl$_3$, 300 MHz) δ8.66 (d, 1H), 7.97 (s, 1H), 7.83 (dd, 1H), 7.58 (s, 1H), 7.50 (dd, 1H), 7.39 (d, 1H), 7.20 (m, 1H), 6.40 (bs, 1H), 4.56 (AB, 2H), 4.12 (m, 1H), 3.31 (m, 2H), 2.65 (m, 1H), 2.20 (m, 1H). IS MS, [M+H]$^+$=431.

G. 4-[3-(S)-(6-Fluoro-benzo[b]thiophene-2-sulfonylamino)-2-oxo-pyrrolidin-1-ylmethyl]-pyridine-2-carboxamidine hydrochloride.

Hydrogen sulfide gas is bubbled for 5 minutes through a solution of 6-fluoro-benzo[b]-thiophene-2-sulfonic acid-[1-(2-cyano-pyridin-4-ylmethyl)-2-oxo-pyrrolidin-3-(S)-yl]-amide (0.67 g, 1.56 mmol) in 10 mL of a 10:1 mixture of pyridine/triethylamine. After stirring the pale green solution for a period of 64 hours, the reaction mixture is concentrated in vacuo. The residue is diluted in acetone and concentrated to give the crude thioamide. To a solution of thioamide in 20 mL of acetone is added iodomethane (5.5 mL). The resulting mixture is heated at reflux for 2.5 hours, allowed to cool to room temperature and concentrated in vacuo to provide the crude thioimidate hydroiodide. To a solution of thioimidate hydroiodide in 20 mL of MeOH is added ammonium acetate (0.60 g, 7.60 mmol). The resulting mixture is heated at reflux for 2 hours, allowed to cool to room temperature and stirred overnight. The resulting mixture is concentrated in vacuo to provide the crude amidine salt. The crude product is purified by RP-HPLC eluting in a gradient of 10% $CH_3CN/H_2O$ (0.05% HCl) to 80% $CH_3CN/H_2O$ (0.05% HCl) and the appropriate product fractions are lyophilized to provide the title compound (0.27 g, 0.56 mmol) as a white amorphous solid.

$^1$H NMR (DMSO-$d_6$, 300 MHz) δ9.10 (bs, 2H), 8.77 (bs, 2H), 8.55 (d, 1H), 7.63 (dd, 1H), 7.61 (d, 1H), 7.43 (d, 1H), 7.35 (dd, 2H), 7.19 (d, 1H), 7.01 (d, 1H), 4.33 (AB, 2H), 4.20 (m, 1H), 3.25 (m, 2H), 2.20 (m, 1H), 1.77 (m, 1H). FAB MS, $[M+H]^+$=448. Elemental analysis calculated with 0.70 mol $H_2O$ cal. C=42.96%, H=4.62%, N=13.18%, found: C=42.96%, H=3.58%, N=12.80%.

The molecules described herein inhibit blood coagulation by virtue of their ability to inhibit the penultimate enzyme in the coagulation cascade, controlling the activity of Factor Xa. Both the activity of free Factor Xa and Factor Xa assembled in the prothrombinase complex (Factor Xa, Factor Va, calcium and phospholipid) are inhibited by compounds of formula 1. The inhibition of the Factor Xa activity is obtained by direct complex formation between the inhibitor and the enzyme and is therefore independent of the plasma co-factor antithrombin III. Effective inhibition of the Factor Xa activity is achieved by administering the compounds either by oral administration, continuous intravenous infusion, bolus intravenous administration or any other parenteral route such that it achieves the desired effect of preventing the activity of Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

These compounds may be used alone or in combination with other diagnostic, anticoagulant, antiplatelet or fibrinolytic agents. For example adjunctive administration of inhibitors of the activity of Factor Xa with standard heparin, low molecular weight heparin, direct thrombin inhibitors (i.e. hirudin), aspirin, fibrinogen receptor antagonists, streptokinase, urokinase and/or tissue plasminogen activator may result in greater antithrombotic or thrombolytic efficacy or efficiency. The compounds described herein may be administered to treat thrombotic complications in a variety of animals such as primates including humans. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any inhibitor of Factor Xa activity can be added to or contacted with any medium containing or suspected of containing Factor Xa and in which it is desired that blood coagulation be inhibited.

In addition to their use in anticoagulant therapy, inhibitors of Factor Xa activity may find utility in the treatment of prevention of other physiological conditions in which the generation of thrombin has been implicated as playing a pathologic role. For example, thrombin has been proposed to contribute to the morbidity and mortality of such chronic and degenerative diseases as arthritis, cancer, atherosclerosis, restenosis post coronary angioplasty and Alzheimer's disease by virtue of its ability to regulate many different cell types through specific cleavage and activation of a cell surface thrombin receptor. Inhibition of factor Xa activity will effectively block thrombin generation and therefore neutralize any pathologic effects of thrombin on various cell types.

According to a further feature of the invention there is provided a method for the treatment of a human or animal patient suffering from, or subject to, a physiological condition which can be ameliorated by the administration of an inhibitor of the Factor Xa activity, for example conditions as hereinbefore described, which comprises the administration to the patient of a therapeutically effective amount of compound of formula I or a composition containing a compound of formula I. "Effective amount" is meant to describe an amount of compound of the present invention effective in inhibiting the activity of Factor Xa and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, intravenously, subcutaneously intramuscularly, colonically, nasally, intraperitoneally, rectally or orally.

The products according to the invention may be presented informs permitting administration by the most suitable route and the invention also relates to pharmaceutical compositions containing at least one product according to the invention which are suitable for use inhuman or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day be intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

Enzyme Assays:

The ability of the compounds in the present invention to act as inhibitors of factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity (IC50). The apparent Ki values are then determined according to the Cheng-Prusoff equation (IC50= Ki[1+[S]/Km]) assuming competitive inhibition kinetics.

By way of example, 3-[3-(S)-(Benzo[b]thiophene-2-sulfonylamino)-2-oxo-pyrrolidin-1-ylmethyl]-benzamidine trifluoroacetate has a Ki value of 14 nM.

By way of example, 3-[2-Oxo-3-(S)-(5-pyridin-4-yl-thiophene-2-sulfonylamino)-pyrrolidin-1-ylmethyl]-benzamidine trifluoroacetate has a Ki value of 55 nM.

An additional in vitro assay may be used to evaluate the potency of compounds according to the invention in normal human plasma. The activated partial thromboplastin time is a plasma-based clotting assay that relies on the in situ generation of factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay:

Activated partial thromboplastin clotting times are determined in duplicate on a MLA Electra 800 instrument. A volume of 100 μl of citrated normal human pooled plasma (George King Biomedical) is added to a cuvette containing 100 μl of a compound according to the invention in Tris/NaCl buffer (pH 7.5) and placed in the instrument. Following a 3 minute warming period the instrument automatically adds 100 μl of activated cephaloplastin reagent (Actin, Dade) followed by 100 μl of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

A compound according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental In Vivo Rabbit Venous Thrombosis Model:

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis-a Comparison with Low Molecular Weight Heparin, J. Holst, B. Lindblad, D. Bergqvist, O. Nordfang, P. B. Ostergaard, J. G. L. Petersen, G. Nielsen and U. Hedner. *Thrombosis and Haemostasis,* 71, 214–219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5–2 kg are anesthetized with35 mg/kg of ketamine and 5 mg/kg xylazine in a volume of 1 ml/kg (i.m.). The right jugular vein is cannulated for infusion of anesthetic (ketamine/xylazine 17/2.5 mg/kg/hr at a rate of approximately 0.5 ml/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2–3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by typing a ligature around the vein with an 18 G needle just below the distal most clamp. This creates a region of reduced flow and partial stasis at the injury site. The isolated segment is gently rinsed with saline 2–3 times via the cannula in the internal jugular. Thereafter the isolated segment is filled with 0.5 ml of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2–3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 ml ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental In Vivo Rat Arterial Thrombosis Model:

The antithrombotic efficacy of factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. *Journal of Cardiovascular Pharmacology,* 2, 526–533 (1993); Rat Model of Arterial Thrombosis Induced by Ferric Chloride, K. D. Kurtz, B. W. Main, and G. E. Sandusky. *Thrombosis Research,* 60, 269–280 (1990); The Effect of Thrombin Inhibition in a Rat Arterial Thrombosis Model, R. J. Broersma, L. W. Kutcher and E. F. Heminger. *Thrombosis Research* 64, 405–412 (1991). This model is widely used to evaluate the antithrombotic potential of a variety of agents including heparin and the direct acting thrombin inhibitors.

Sprague Dawley rats weighing 375–450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead II is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95–1.0 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is though to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 ml of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 ml/kg). Fifteen minutes after intragastric dosing, the animal is anesthetized and instrumented as described previously. Experiments are then performed according to the protocol described above.

The present invention may be embodied in other specific forms without departing from the spirit or essential attributes thereof.

What is claimed is:

1. A compound of formula I

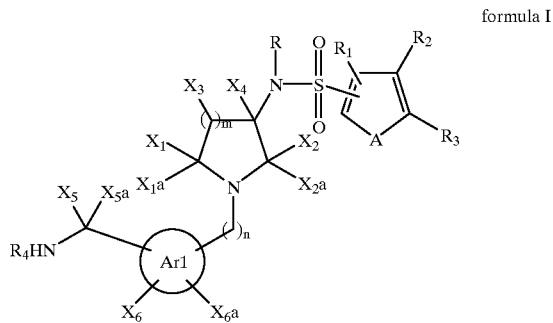

formula I wherein

is phenyl or monocyclic heteroaryl;

R is hydrogen, optionally substituted alkyl, optionally substituted aralkyl, optionally substituted heteroaralkyl, $R_6O(CH_2)_x$—, $R_6O_2C(CH_2)_x$—, $Y^1Y^2NC(O)(CH_2)_x$—, or $Y^1Y^2N(CH_2)_x$—;

$R_1$ is hydrogen, alkyl, hydroxy, alkoxy, $Y^1Y^2N$—, halogen, —$CO_2R_6$, —$C(O)NY^1Y^2$, —$(CH_2)_xOR_6$, —$(CH_2)_xNY^1Y^2$, or —CN;

$R_2$ and $R_3$ are independently selected from hydrogen, hydroxy, alkoxy, $Y^1Y^2N$—, halogen, —$CO_2R_6$, —$C(O)NY^1Y^2$, —$(CH_2)_xOR_6$, —$(CH_2)_xNY^1Y^2$, —CN, optionally substituted alkyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl or optionally substituted heteroaralkenyl, or $R_2$ and $R_3$ taken together with the carbon atoms through which they are linked form an optionally substituted 5 to 7 membered fused cycloalkyl, optionally substituted 5 to 7 membered fused heterocyclyl ring or an optionally substituted 6 membered fused aryl, or an optionally substituted 5 to 7 membered fused heteroaryl ring;

$R_4$ is hydrogen or optionally substituted lower alkyl, optionally substituted aralkyl or optionally substituted heteroaralkyl;

$X_1$ and $X_{1a}$ are independently selected from hydrogen, optionally substituted alkyl, optionally substituted aryl, optionally substituted aralkyl, optionally substituted heteroaryl or optionally substituted heteroaralkyl, or $X_1$ and $X_{1a}$ taken together form oxo;

$X_2$ and $X_{2a}$ are hydrogen, or taken together form oxo;

$X_3$ is hydrogen, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1a}$ taken together with the carbon atoms through which $X_3$ and one of $X_1$ and $X_{1a}$ are linked form a 4 to 7 membered cycloalkyl or heterocyclyl ring;

$X_4$ is hydrogen, optionally substituted alkyl or an optionally substituted aralkyl;

$X_5$ and $X_{5a}$ are hydrogen or taken together are =$NR_5$;

$R_5$ is hydrogen, $R_6O_2C$—, $R_6O$—, cyano, $R_6CO$—, optionally substituted lower alkyl, nitro or $Y^1Y^2N$—;

$Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl;

$X_6$ and $X_{6a}$ are independently hydrogen, $R_7R_8N$—, $R_9O$—, $R_7R_8NCO$—, $R_7R_8NSO_2$—, $R_7R_8NSO_2N$—, $R_7R_8SO_2O$—, $R_9CO$—, —$CO_2R_6$, —$C(O)NY^1Y^2$, —$(CH_2)_xCO_2R_6$, —$(CH_2)_xC(O)NY^1Y^2$, —$(CH_2)_xOR_6$, —$(CH_2)_xNY^1Y^2$, halo, cyano or nitro;

$R^6$ is hydrogen, optionally substituted alkyl, optionally substituted aralkyl or optionally substituted heteroaralkyl;

$R_7$ and $R_8$ are independently hydrogen or optionally substituted lower alkyl, or one of $R_7$ and $R_8$ is hydrogen and the other of $R_7$ and $R_8$ is $R_{10}(O)CCH_2$— or lower acyl;

$R_9$ is hydrogen, optionally substituted lower alkyl, optionally substituted lower acyl or $R_{10}(O)CCH_2$—;

$R_{10}$ is hydrogen, optionally substituted lower alkyl, optionally substituted alkoxy or hydroxy;

A is S or —CH=CH—; provided that (A) when A is —CH=CH—, then $R_2$ is hydrogen and $R_3$ is an optionally substituted heteroaryl ring or an optionally substituted 6 membered aryl ring, and (B) when A is S, then (1) $R_2$ and $R_3$ taken together with the carbon atoms through which $R_2$ and $R_3$ are linked form an optionally substituted 5 or 6 membered heteroaryl ring or an optionally substituted 6 membered aryl ring or (2) $R_2$ is hydrogen and $R_3$ is an optionally substituted heteroaryl ring or an optionally substituted 6 membered aryl ring;

m is 0, 1, 2 or 3;

n is 0, 1, 2 or 3; and x is 1, 2, 3, 4, or 5, or a pharmaceutically acceptable salt thereof, an N-oxide thereof, a hydrate thereof or a solvate thereof.

2. A compound of claim 1 wherein n=1 and m=1.

3. A compound of claim 1 wherein $X_2$ and $X_{2a}$ taken together are oxo.

4. A compound of claim 1 wherein $X_1$, $X_{1a}$, $X_4$ are hydrogen, and $X_3$ is hydrogen or alkyl.

5. A compound of claim 1 wherein $X_5$ and $X_{5a}$ taken together are $=NR_5$ wherein $R_5$ is $R_6O_2C—$.

6. A compound of claim 1 wherein $X_5$ and $X_{5a}$ taken together are $=NR_5$ wherein $R_5$ is $—OH$.

7. A compound of claim 1 wherein $X_5$ and $X_{5a}$ taken together are $=NR_5$ wherein $R_5$ is H.

8. A compound of claim 1 wherein

is phenyl and the carbon substituted with $X_5$, $X_{5a}$ and $R_4HN—$ is attached meta relative to the attachment of the $—(CH)_nN—$ moiety to the phenyl.

9. A compound of claim 1 wherein

is thienyl and the carbon substituted with $X_5$, $X_{5a}$ and $R_4HN—$ is attached in the 2 position relative to the sulfur of the thienyl and the attachment of the $—(CH)_nN—$ moiety is to the 4 position of the thienyl.

10. A compound of claim 1 wherein R is hydrogen, methyl, aralkyl, heteroaralkyl, $HO_2CCH_2—$, $H_2NC(O)CH_2—$, or $R_6HNC(O)CH_2—$.

11. A compound of claim 1 wherein $R_1$ is hydrogen, alkyl, or halogen.

12. A compound of claim 1 wherein

is phenyl and one of $X_6$ and $X_{6a}$ is amino or hydroxy in a para position relative to the

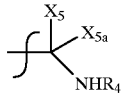

moiety.

13. A compound of claim 1 wherein $X_6$ and $X_{6a}$ are hydrogen.

14. A compound of claim 1 wherein A is S.

15. A compound selected from the group consisting of
4-Hydroxy-3-[3-(S)-(7-chloro-thieno[2,3-c]pyridine-2-sulfonylamino)-2-oxo-pyrrolidin-1-ylmethyl]-benzamidine trifluoroacetate;
4-Hydroxy-3-[3-(S)-(thieno[2,3-c]pyridine-2-sulfonylamino)-2-oxo-pyrrolidin-1-ylmethyl]-benzamidine bistrifluoroacetate;
4-Hydroxy-3-[3-(S)-(thieno[3,2-c]pyridine-2-sulfonylamino)-2-oxo-pyrrolidin-1-ylmethyl]-benzamidine trifluoroacetate;
4-[3-(6-Fluorobenzo[b]thiophene-2-sulfonylamino)-2-oxo-pyrrolidin-1-ylmethyl]-thiophene-2-carboxamidine hydrochloride;
4-{3-(S)-[(3-Aminopropyl)-(6-fluorobenzo[b]thiophene-2-sulfonylamino)-2-oxo-pyrrolidin-1-ylmethyl}-thiophene-2-carboxamidine bistrifluoroacetate;
[[1-(5-Carbamimidoyl-thiophen-3-ylmethyl-2-oxo-pyrrolidin-3-yl]-(6-fluorobenzo[b thiophen-2-sulfonyl)-amino]-acetic acid trifluoroacetate;
[Imino-(4-{3-[(7-methoxynaphthalene-2-sulfonyl)-pyridin-2-ylmethyl-amino]-2-oxo-pyrrolidin-1-ylmethyl}-thiophen-2-yl)-methyl]-carbamic acid ethyl ester;
4-Amino-3-{3-(S)-[(7-methoxy-naphthalene-2-sulfonyl)-pyridine-2-ylmethyl-amino]-2-oxo-pyrrolidin-1-ylmethyl}-benzamidine trifluoroacetate;
2-[[1-(2-Amino-5-carbamimidoyl-benzyl)-2-oxo-pyrrolidin-3-(S)-yl}-(7-methoxy-naphthalene-2-sulfonyl)-amino]-acetamide trifluoroacetate;
[Imino-(3-{3-[(7-methoxy-naphthalene-2-sulfonyl)-methylamino]-2-oxo-3-(S)-pyrrolidin-1-ylmethyl}-4-amino-phenyl)-methyl]carbamic acid ethyl ester;
4-Hydroxy-3-{3-(S)-[5-(1-Hydroxy-pyridin-4-yl)-thiophene-2-sulfonyl amino]-2-oxo-pyrrolidin-1-ylmethyl}-benzamidine trifluoroacetate;
4-Amino-3-[3-(S)-(5-chloro-thieno[3,2-b]pyridine-2-sulfonylamino)-2-oxo-pyrrolidin-1-ylmethyl]-hydroxybenzamidine trifluoroacetate;
4-Amino-3-[3-(S)-(5-methoxy-thieno[3,2-b]pyridine-2-sulfonylamino)-2-oxo-pyrrolidin-1-ylmethyl]-benzamidine bistrifluoroacetate;
3-[3-(S)-(5-Isoxazol-3-yl-thiophene-2-sulfonylamino)-2-oxo-pyrrolidin-1-ylmethyl]-benzamidine trifluoroacetate;
4-Amino-3-[3-(S)-(5-isoxazol-3-yl-thiophene-2-sulfonylamino)-2-oxo-pyrrolidin-1-ylmethyl]-benzamidine trifluoroacetate;
4-Hydroxy-3-[3-(S)-(5-isoxazol-3-yl-thiophene-2-sulfonylamino)-2-oxo-pyrrolidin-1-ylmethyl}-benzamidine trifluoroacetate;
3-(S)-[3-([2,2']-Bithiophenyl-5-sulfonylamino)-2-oxo-pyrrolidin-1-ylmethyl]-benzamidine trifluoroacetate;
4-Amino-3-[3-(S)-([2,2']-bithiophenyl-5-sulfonylamino)-2-oxo-pyrrolidin-1-ylmethyl]-benzamidine trifluoroacetate;
4-Amino-3-[3-(S)-(5'-chloro-[2,2']-bithiophenyl-5-sulfonylamino)-2-oxo-pyrrolidin-1-ylmethyl]-benzamidine trifluoroacetate;
4-Hydroxy-3-[3-(S)-(5'-chloro-[2,2']-bithiophenyl-5-sulfonylamino)-2-oxo-pyrrolidin-1-ylmethyl}-benzamidine hydrochloride;
4-Hydroxy-3-[3-(S)-(5'-chloro-[2,2']-bithiophenyl-5-sulfonylamino)-2-oxo-pyrrolidin-1-ylmethyl]-hydroxybenzamidine; and
4-[3-(S)-(6-Fluoro-benzo[b]thiophene-2-sulfonylamino)-2-oxo-pyrrolidin-1-ylmethyl]-pyridine-2-carboxamidine hydrochloride.

16. A compound according to claim 15 which is 4-Hydroxy-3-[3-(S)-(7-chloro-thieno[2,3-c]pyridine-2-sulfonylamino)-2-oxo-pyrrolidin-1-ylmethyl]-benzamidine trifluoroacetate.

17. A compound according to claim 15 which is 4-Hydroxy-3-[3-(S)-(thieno[2,3-c]pyridine-2-sulfonylamino)-2-oxo-pyrrolidin-1-ylmethyl]-benzamidine bistrifluoroacetate.

18. A compound according to claim 15 which is 4-Hydroxy-3-[3-(S)-(thieno[3,2-c]pyridine-2-sulfonylamino)-2-oxo-pyrrolidin-1-ylmethyl]-benzamidine trifluoroacetate.

19. A compound according to claim 15 which is 4-Hydroxy-3-{3-(S)-[5-(1-Hydroxy-pyridin-4-yl)-thiophene-2-sulfonyl amino]-2-oxo-pyrrolidin-1-ylmethyl}-benzamidine trifluoroacetate.

20. A compound according to claim 15 which is 4-Amino-3-[3-(S)-(5-methoxy-thieno[3,2-b]pyridine-2-sulfonylamino)-2-oxo-pyrrolidin-1-ylmethyl]-benzamidine bistrifluoroacetate.

21. A compound according to claim 15 which is 4-Amino-3-[3-(S)-(5-isoxazol-3-yl-thiophene-2-sulfonylamino)-2-oxo-pyrrolidin-1-ylmethyl]-benzamidine trifluoroacetate.

22. A compound according to claim 15 which is 4-Hydroxy-3-[3-(S)-(5-isoxazol-3-yl-thiophene-2-sulfonylamino)-2-oxo-pyrrolidin-1-ylmethyl]-benzamidine trifluoroacetate.

23. A compound according to claim 15 which is 4-Amino-3-[3-(S)-([2,2']-bithiophenyl-5-sulfonylamino)-2-oxo-pyrrolidin-1-ylmethyl]-benzamidine trifluoroacetate.

24. A compound according to claim 15 which is 4-Amino-3-[3-(S)-(5'-chloro-[2,2']-bithiophenyl-5-sulfonylamino)-2-oxo-pyrrolidin-1-ylmethyl]-benzamidine trifluoroacetate.

25. A compound according to claim 15 which is 4-Hydroxy-3-[3-(S)-(5'-chloro-[2,2']-bithiophenyl-5-sulfonylamino)-2-oxo-pyrrolidin-1-ylmethyl]-benzamidine hydrochloride.

26. A pharmaceutical composition comprising a therapeutically effective amount of a compound according to claim 1 and a pharmaceutically acceptable carrier.

27. A method for treating a patient suffering from a physiological disorder capable of being modulated by inhibiting an activity of Factor Xa comprising administering to the patient a therapeutically effective amount of a compound according to claim 1.

28. A method according to claim 27 wherein the physiological disorder is a disorder of venous vasculature, a disorder of arterial vasculature, abnormal thrombus formation, acute myocardial infarction, unstable angina, thromboembolism, acute vessel closure associated with thrombolytic therapy, percutaneous transluminal coronary angioplasty, transient ischemic attacks, stroke, intermittent claudication or bypass grafting of the coronary or peripheral arteries, vessel luminal narrowing, restenosis post coronary or venous angioplasty, one involving maintenance of vascular access patency in long-term hemodialysis patients, pathologic thrombus formation occurring in the veins of the lower extremities following abdominal, knee and hip surgery, a disorder causing risk of pulmonary thromboembolism, or disseminated systemic intravascular coagulopathy occurring in vascular systems during septic shock, certain viral infections or cancer.

29. A method according to claim 27 wherein the physiological disorder is abnormal thrombus formation, acute myocardial infarction, unstable angina, thromboembolism, acute vessel closure associated with thrombolytic therapy, transient ischemic attacks, intermittent claudication or bypass grafting of the coronary or peripheral arteries, restenosis post coronary or venous angioplasty, pathologic thrombus formation occurring in the veins of the lower extremities following abdominal, knee and hip surgery or a disorder causing risk of pulmonary thromboembolism.

30. A method according to claim 27 wherein the physiological disorder is stroke, vessel luminal narrowing, one involving maintenance of vascular access patency in long-term hemodialysis patients, or disseminated systemic intravascular coagulopathy occurring in vascular systems during septic shock, certain viral infections or cancer.

* * * * *